(12) United States Patent
MacAtangay et al.

(10) Patent No.: US 8,641,753 B2
(45) Date of Patent: Feb. 4, 2014

(54) PREFORM FOR AND AN ENDOLUMINAL PROSTHESIS

(75) Inventors: Edwin E. MacAtangay, Bloomington, IN (US); Mark R. Frye, Bloomington, IN (US); Jeffry S. Melsheimer, Springville, IN (US); Jacqueline Farag, Bloomington, IN (US)

(73) Assignee: Cook Medical Technologies LLC, Bloomington, IN (US)

(\*) Notice: Subject to any disclaimer, the term of this patent is extended or adjusted under 35 U.S.C. 154(b) by 610 days.

(21) Appl. No.: 12/695,693

(22) Filed: Jan. 28, 2010

(65) Prior Publication Data

US 2010/0198333 A1 Aug. 5, 2010

Related U.S. Application Data

(60) Provisional application No. 61/148,945, filed on Jan. 31, 2009, provisional application No. 61/148,942, filed on Jan. 31, 2009.

(51) Int. Cl.
*A61F 2/06* (2013.01)

(52) U.S. Cl.
USPC .......................................... 623/1.13; 623/1.15

(58) Field of Classification Search
USPC ...................... 623/1.11, 1.13, 1.15, 1.22, 1.23
See application file for complete search history.

(56) References Cited

U.S. PATENT DOCUMENTS

| | | | |
|---|---|---|---|
| 4,561,439 A | 12/1985 | Bishop et al. | |
| 4,886,062 A | 12/1989 | Wiktor | |
| 5,226,913 A | 7/1993 | Pinchuk | |
| 5,269,751 A | 12/1993 | Kaliman et al. | |
| 5,282,824 A | 2/1994 | Gianturco | |
| 5,314,472 A | 5/1994 | Fontaine | |
| 5,316,023 A | 5/1994 | Palmaz et al. | |
| 5,360,443 A | 11/1994 | Barone et al. | |
| 5,370,653 A | 12/1994 | Cragg | |
| 5,370,683 A * | 12/1994 | Fontaine | 623/1.22 |
| 5,376,100 A | 12/1994 | Lefebvre | |

(Continued)

FOREIGN PATENT DOCUMENTS

| | | |
|---|---|---|
| WO | WO 91/12779 A1 | 9/1991 |
| WO | 99/37242 | 7/1999 |

(Continued)

OTHER PUBLICATIONS

International Search Report and Written Opinion of the International Searching Authority for International Application No. PCT/US2009/005005, dated Nov. 16, 2009, 10 pages.

(Continued)

*Primary Examiner* — S. Thomas Hughes
*Assistant Examiner* — Katherine M Shi
(74) *Attorney, Agent, or Firm* — Brinks Gilson & Lione

(57) ABSTRACT

An endoluminal prosthesis may include a tubular graft extending in a longitudinal direction, where the graft has an inner surface forming a lumen extending a length of the graft. An elongate member may be attached to the graft in a circumferentially and longitudinally extending manner such that the elongate member forms a series of longitudinally spaced apart turns, each turn extending substantially around a circumference of the graft. The elongate member may torsion the graft in at least the circumferential direction and cause the graft to form circumferentially and longitudinally extending folds in the portions of the graft disposed between longitudinally adjacent turns of the elongate member.

19 Claims, 48 Drawing Sheets

(56) References Cited

U.S. PATENT DOCUMENTS

| | | |
|---|---|---|
| 5,443,498 A | 8/1995 | Fontaine |
| 5,476,506 A | 12/1995 | Lunn |
| 5,507,767 A | 4/1996 | Maeda et al. |
| 5,527,354 A | 6/1996 | Fontaine et al. |
| 5,554,182 A | 9/1996 | Dinh et al. |
| 5,591,195 A | 1/1997 | Taheri et al. |
| D390,957 S | 2/1998 | Fontaine |
| 5,782,904 A | 7/1998 | White et al. |
| 5,800,456 A | 9/1998 | Maeda et al. |
| 5,865,723 A | 2/1999 | Love |
| 5,968,057 A | 10/1999 | Taheri |
| 5,984,965 A | 11/1999 | Knapp et al. |
| 6,019,779 A | 2/2000 | Thorud et al. |
| 6,042,605 A | 3/2000 | Martin et al. |
| 6,077,296 A | 6/2000 | Shokoohi et al. |
| 6,090,128 A | 7/2000 | Douglas |
| 6,137,060 A | 10/2000 | Avellanet |
| 6,156,062 A | 12/2000 | McGuiness |
| 6,156,063 A | 12/2000 | Douglas |
| 6,159,239 A | 12/2000 | Greenhalgh |
| 6,187,036 B1 | 2/2001 | Shaolian et al. |
| 6,191,365 B1 | 2/2001 | Avellanet |
| 6,197,049 B1 | 3/2001 | Shaolian et al. |
| 6,210,422 B1 | 4/2001 | Douglas |
| 6,261,316 B1 | 7/2001 | Shaolian et al. |
| 6,270,524 B1 | 8/2001 | Kim |
| 6,278,057 B1 | 8/2001 | Avellanet |
| 6,319,277 B1 | 11/2001 | Rudnick et al. |
| 6,331,188 B1 | 12/2001 | Lau et al. |
| 6,331,190 B1 | 12/2001 | Shokoohi et al. |
| 6,338,739 B1 | 1/2002 | Datta et al. |
| 6,361,637 B2 | 3/2002 | Martin et al. |
| 6,364,904 B1 | 4/2002 | Smith |
| 6,440,161 B1 | 8/2002 | Madrid et al. |
| 6,454,775 B1 | 9/2002 | Demarais et al. |
| 6,491,619 B1 | 12/2002 | Trauthen et al. |
| 6,500,202 B1 | 12/2002 | Shaolian et al. |
| 6,508,835 B1 | 1/2003 | Shaolian et al. |
| 6,517,570 B1 | 2/2003 | Lau et al. |
| 6,517,572 B2 | 2/2003 | Kugler et al. |
| 6,520,986 B2 | 2/2003 | Martin et al. |
| 6,530,935 B2 | 3/2003 | Wensel et al. |
| 6,551,350 B1 | 4/2003 | Thornton et al. |
| 6,565,596 B1 | 5/2003 | White et al. |
| 6,635,080 B1 | 10/2003 | Lauterjung et al. |
| 6,652,548 B2 | 11/2003 | Evans et al. |
| 6,660,030 B2 | 12/2003 | Shaolian et al. |
| 6,663,665 B2 | 12/2003 | Shaolian et al. |
| D484,979 S | 1/2004 | Fontaine |
| 6,685,618 B2 | 2/2004 | Tam et al. |
| 6,685,696 B2 | 2/2004 | Fleischhacker et al. |
| 6,685,722 B1 | 2/2004 | Rosenbluth et al. |
| 6,685,736 B1 | 2/2004 | White et al. |
| 6,689,157 B2 | 2/2004 | Madrid et al. |
| 6,692,509 B2 | 2/2004 | Wensel et al. |
| 6,699,170 B1 | 3/2004 | Crocker et al. |
| 6,733,523 B2 | 5/2004 | Shaolian et al. |
| 6,773,457 B2 | 8/2004 | Ivancev et al. |
| 6,866,680 B2 | 3/2005 | Yassour et al. |
| 6,923,828 B1 | 8/2005 | Wiktor |
| 6,926,725 B2 | 8/2005 | Cooke et al. |
| 6,929,709 B2 | 8/2005 | Smith |
| 6,951,572 B1 | 10/2005 | Douglas |
| 6,953,475 B2 | 10/2005 | Shaolian et al. |
| 6,974,471 B2 | 12/2005 | Van Schie et al. |
| 6,974,473 B2 | 12/2005 | Barclay et al. |
| 6,986,784 B1 | 1/2006 | Weiser et al. |
| 7,018,401 B1 | 3/2006 | Hyodoh et al. |
| 7,037,316 B2 | 5/2006 | McGuckin, Jr. et al. |
| 7,044,905 B2 | 5/2006 | Vidlund et al. |
| 7,060,092 B2 | 6/2006 | Kuribayashi et al. |
| 7,318,835 B2 | 1/2008 | Berra |
| 2001/0007954 A1 | 7/2001 | Shaolian et al. |
| 2002/0013617 A1* | 1/2002 | Matsutani et al. ........... 623/1.15 |
| 2002/0156523 A1 | 10/2002 | Lau et al. |
| 2002/0165603 A1 | 11/2002 | Thornton et al. |
| 2003/0088305 A1 | 5/2003 | Van Schie et al. |
| 2003/0130721 A1 | 7/2003 | Martin et al. |
| 2003/0149475 A1 | 8/2003 | Hyodoh et al. |
| 2004/0024443 A1 | 2/2004 | Dwyer et al. |
| 2004/0044401 A1 | 3/2004 | Bales et al. |
| 2004/0093072 A1* | 5/2004 | Pappas et al. ................. 623/1.15 |
| 2004/0116960 A1 | 6/2004 | Demond et al. |
| 2004/0117003 A1 | 6/2004 | Ouriel et al. |
| 2005/0049574 A1 | 3/2005 | Petrick et al. |
| 2005/0075715 A1 | 4/2005 | Borges et al. |
| 2005/0085894 A1 | 4/2005 | Kershner |
| 2005/0137677 A1 | 6/2005 | Rush |
| 2005/0137680 A1 | 6/2005 | Ortiz et al. |
| 2005/0154448 A1 | 7/2005 | Cully et al. |
| 2005/0177246 A1 | 8/2005 | Datta et al. |
| 2006/0004436 A1* | 1/2006 | Amarant et al. ............. 623/1.15 |
| 2006/0030926 A1 | 2/2006 | Berra |
| 2006/0142841 A1 | 6/2006 | Khosravi et al. |
| 2006/0265052 A1* | 11/2006 | You .............................. 623/1.22 |
| 2006/0293744 A1 | 12/2006 | Peckham et al. |
| 2007/0067024 A1 | 3/2007 | White et al. |
| 2007/0112412 A1 | 5/2007 | Shokoohi et al. |
| 2007/0198079 A1 | 8/2007 | Casey, II et al. |
| 2007/0207186 A1 | 9/2007 | Scanlon et al. |
| 2007/0215268 A1 | 9/2007 | Pingleton et al. |
| 2007/0299497 A1 | 12/2007 | Shaolian et al. |
| 2008/0082154 A1 | 4/2008 | Tseng et al. |
| 2008/0082158 A1 | 4/2008 | Tseng et al. |
| 2008/0082159 A1 | 4/2008 | Tseng et al. |
| 2008/0114445 A1 | 5/2008 | Melsheimer et al. |
| 2008/0147172 A1 | 6/2008 | White et al. |
| 2008/0195191 A1 | 8/2008 | Luo et al. |
| 2008/0228262 A1 | 9/2008 | Goldmann et al. |
| 2008/0262594 A1 | 10/2008 | Morris |
| 2008/0319529 A1 | 12/2008 | Krivoruchko et al. |
| 2008/0319535 A1* | 12/2008 | Craven et al. ................ 623/1.22 |
| 2009/0030499 A1 | 1/2009 | Bebb et al. |
| 2011/0009951 A1 | 1/2011 | Bogert |

FOREIGN PATENT DOCUMENTS

| | | | |
|---|---|---|---|
| WO | WO 99/44536 A1 | | 9/1999 |
| WO | WO 00/28922 | * | 5/2000 |
| WO | 01/52770 | | 7/2001 |
| WO | WO 03/057079 A1 | | 7/2003 |
| WO | 2009/058369 | | 5/2009 |

OTHER PUBLICATIONS

International Preliminary Report on Patentability, PCT/US2010/022515, filed Jan. 29, 2010.

\* cited by examiner

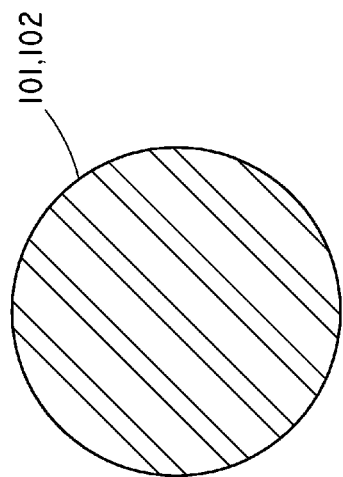
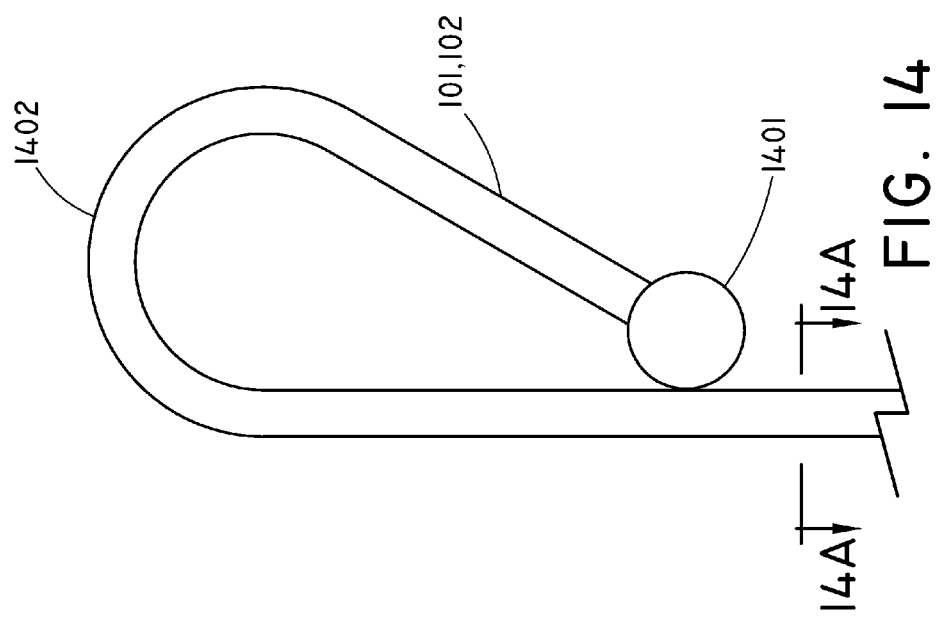

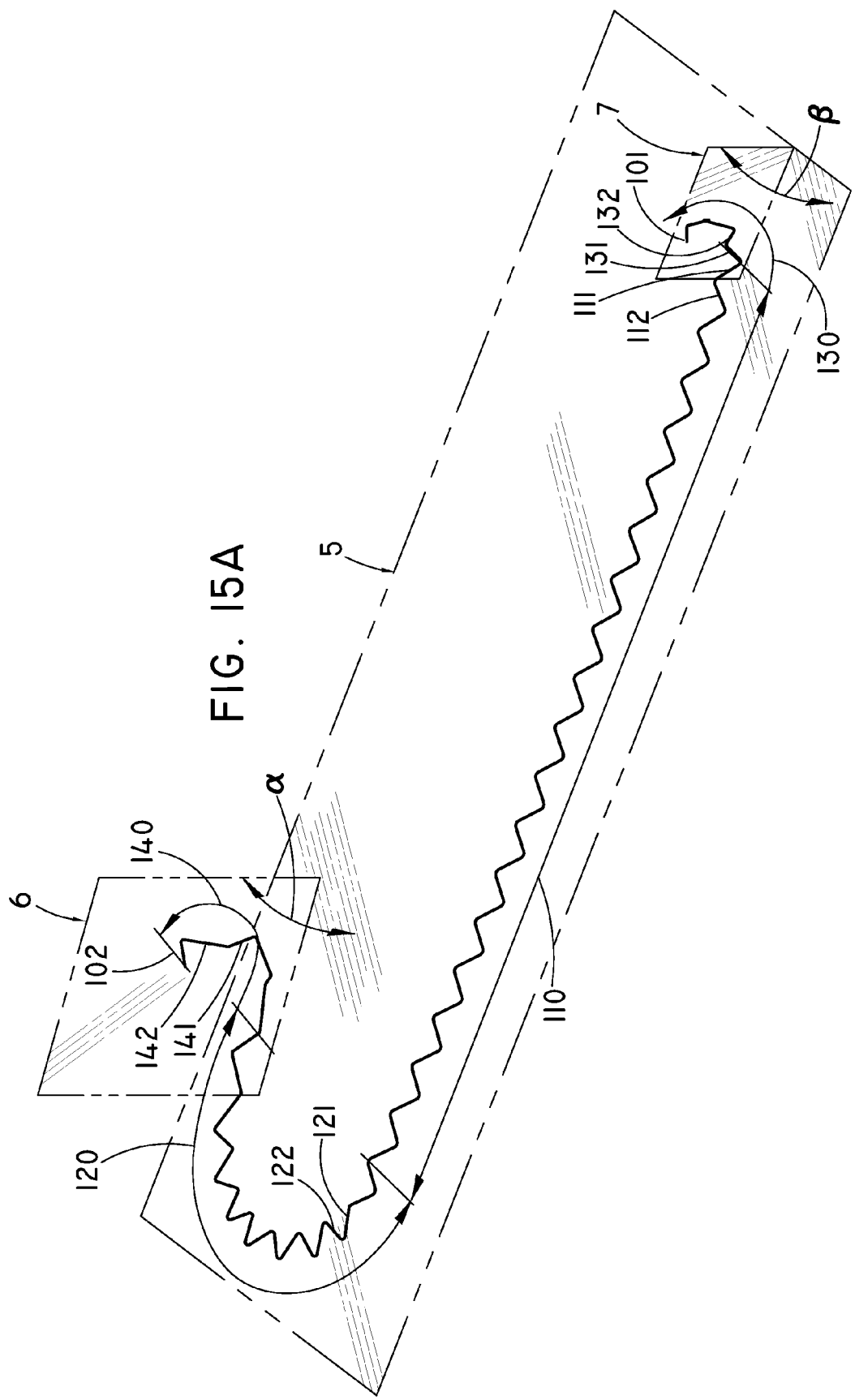

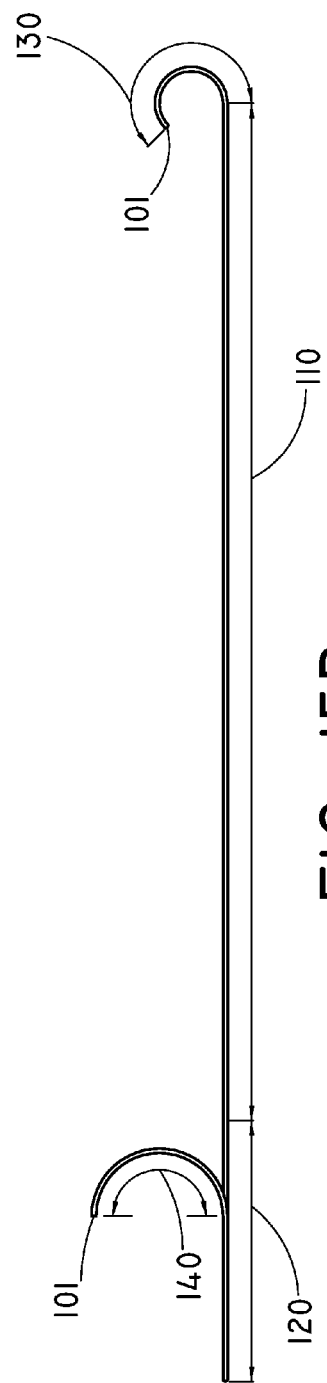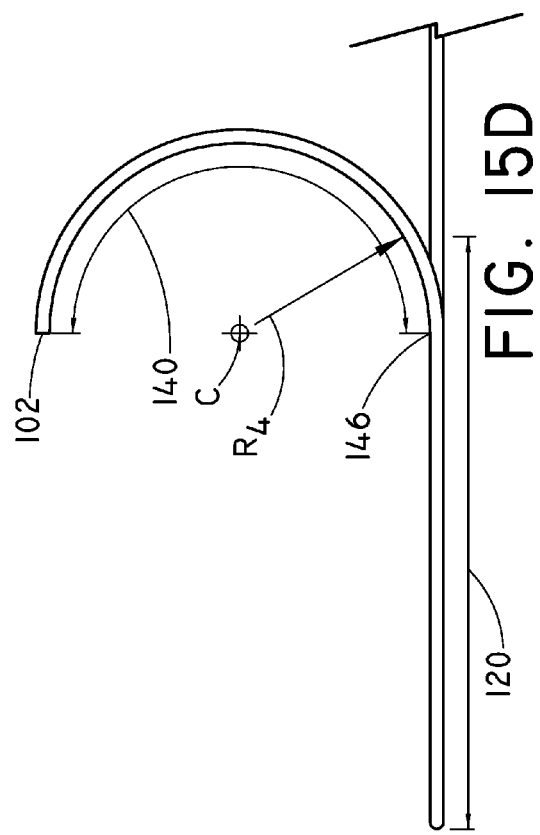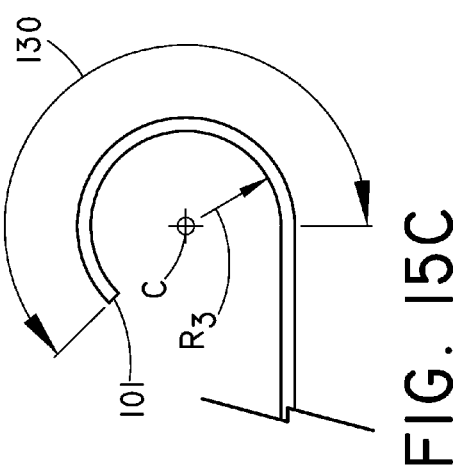

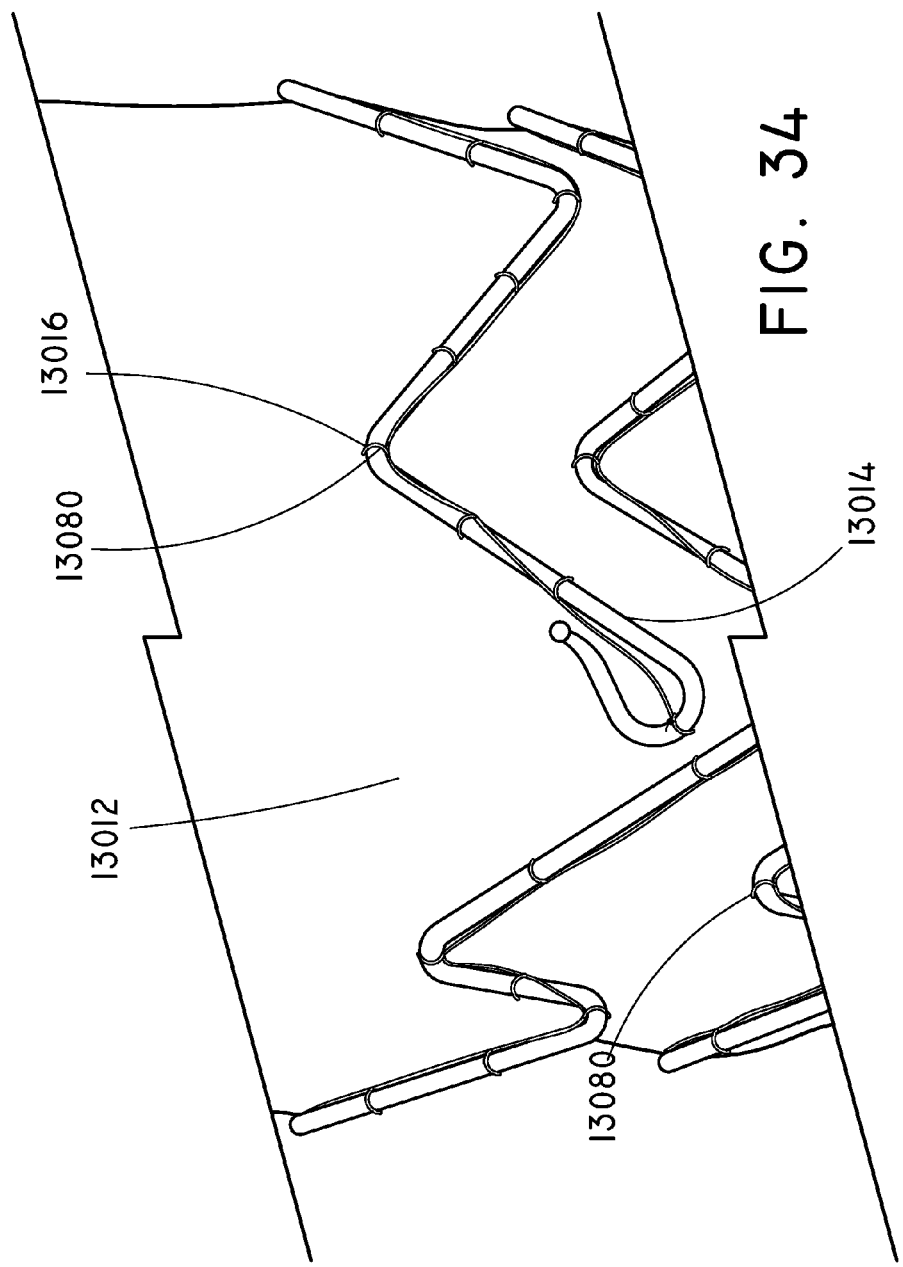

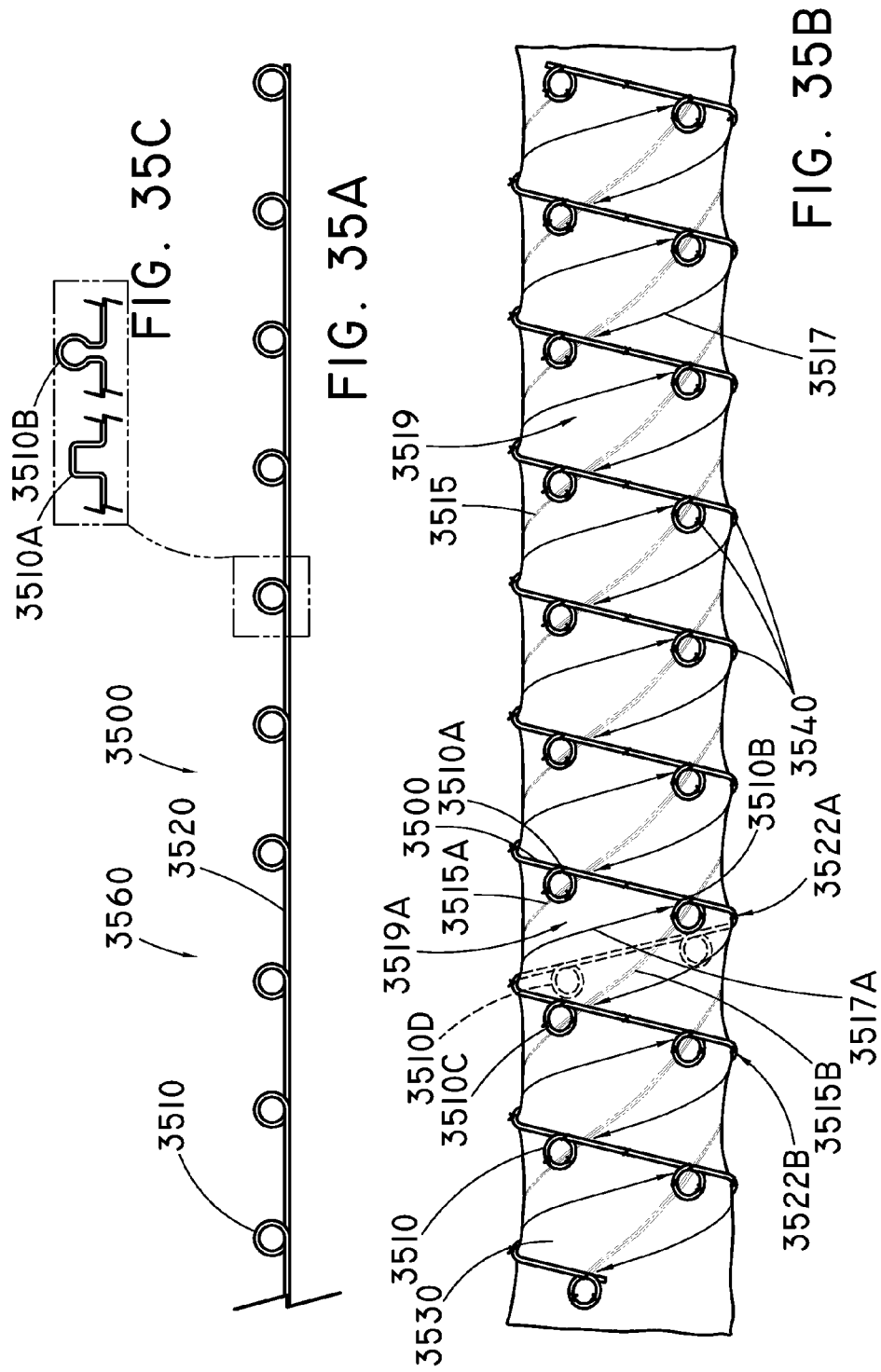

PREFORM FOR AND AN ENDOLUMINAL PROSTHESIS

RELATED APPLICATIONS

The present application claims priority to U.S. Provisional Patent Application Ser. No. 61/148,942 and 61/148,945 filed Jan. 31, 2009, the entirety of which is hereby incorporated by reference.

BACKGROUND

This invention relates generally to medical devices and particularly to medical devices that are implantable within the human or animal body for the repair of damaged vessels, ducts or other physiological passageways and cavities.

The physiological passageways and cavities of human and animal bodies, for example, blood vessels and ducts, occasionally weaken or even rupture. One common surgical intervention for weakened, aneurysmal or ruptured passageways or ducts involves the use of an endoluminal prosthesis to provide some or all of the functionality of the original, healthy passageway or duct and/or preserve any remaining vascular integrity by replacing a length of the existing passageway or duct wall that spans the site of failure or defect. Endoluminal prostheses may be of a unitary construction or may be comprised of multiple prosthetic modules.

SUMMARY

Endoluminal prostheses and preforms of medical devices are described which may allow for increased flexibility while maintaining the integrity of an inner lumen thereof in tortuous anatomy. The invention may include any of the following aspects in various combinations, and may also include any other aspect described below in the written description or in the attached drawings.

In one aspect, an endoluminal prosthesis may include a tubular graft extending in a longitudinal direction with the graft having an inner surface forming a lumen extending a length of the graft. The device may also include an elongate member attached to the graft in a circumferentially and longitudinally extending manner such that the elongate member has a series of longitudinally spaced apart turns, each turn extending substantially around a circumference of the graft. The elongate member is attached to and twists/torques/torsions the graft in at least the circumferential direction, such that the graft has circumferentially and longitudinally extending folds in the portions of the graft disposed between longitudinally adjacent turns of the elongate member.

In another aspect, a preform of a medical device may include an elongate member comprising a plurality of bends, with each bend connecting a pair of first and second struts at an angle. Each of the first struts may extend between adjacent bends in a first direction and each of the second struts may extend between adjacent bends in a second direction, with the second direction being different than the first direction. A first section of the elongate member may have first and second ends, wherein a length of the first struts is shorter than a length of the second struts, and the angle between pairs of first and second struts in the relaxed state is progressively larger for each successive bend moving in a direction from the first end toward the second end.

In another aspect, a method of making an endoluminal prosthesis may include: positioning the elongate member longitudinally and circumferentially about an outer surface of the graft to form a plurality of torqued turns; and attaching the elongate member to the graft such that the elongate member torsions the graft in at least the circumferential direction, and causes the graft to form circumferentially and longitudinally extending folds in the portions of the graft disposed between longitudinally adjacent turns of the elongate member.

In yet another aspect, a method of treating a diseased body lumen may include: providing an endoluminal prosthesis comprising a tubular graft extending in a longitudinal direction, where the graft has an inner surface forming a lumen extending a length of the graft; and an elongate member attached to the graft in a circumferentially and longitudinally extending manner and having a series of longitudinally spaced apart turns, with each turn extending substantially around a circumference of the graft, wherein the elongate member is attached to and torsions the graft in at least the circumferential direction, with the graft having circumferentially and longitudinally extending folds in the portions of the graft disposed between longitudinally adjacent turns of the elongate member, wherein the endoluminal prosthesis is movable between a first condition in which the endoluminal prosthesis is substantially straight to a second condition in which the endoluminal prosthesis is curved to approximate the curved shape of a body lumen, with the endoluminal prosthesis having an interior radius and an exterior radius in the second condition, the inner radius being less than the outer radius, and wherein, when the endoluminal prosthesis is in the first condition, the lumen has a substantially circular open cross sectional area, and wherein, when the graft is in the second condition the portion of the graft disposed about at least the interior radius at least partially compresses, thereby creating a plurality of discrete, localized folds in the graft that substantially maintain the patency of the lumen; advancing the endoluminal prosthesis into the body lumen; and implanting the endoluminal prosthesis in the body lumen.

The foregoing paragraphs have been provided by way of general introduction, and are not intended to limit the scope of the following claims. The presently preferred embodiments, together with further advantages, will be best understood by reference to the following detailed description taken in conjunction with the accompanying drawings.

BRIEF DESCRIPTION OF THE DRAWINGS

The endoluminal prostheses and preforms of medical devices according to embodiments of the present invention may be better understood with reference to the following drawings and description, provided by way of example only. The components in the figures are not necessarily to scale, emphasis instead being placed upon illustrating the principles of the disclosure. Moreover, in the figures, like referenced numerals refer to like elements.

FIG. 14 is a close-up view of an end of an elongate member.

FIG. 14A is a cross section of the end of the elongate member of FIG. 14.

FIGS. 15A and B are orthogonal views of the preform of FIG. 1B having portions formed in a plane and end portions that curve away from the plane.

FIGS. 15C and D are close-up end views of the curved end portions of FIGS. 15A and B.

FIG. 34 illustrates a final endoluminal prosthesis after the attachment of the elongate member longitudinally and circumferentially about the surface of the graft;

FIG. 35A illustrates another embodiment of a preform; and

FIG. 35B illustrates an endoluminal prosthesis using the preform of FIG. 35A.

FIG. 35C illustrates alternative embodiments of attachment members for the preform of FIG. 35A.

DETAILED DESCRIPTION OF THE DRAWINGS AND THE PRESENTLY PREFERRED EMBODIMENTS

Figure 1A:
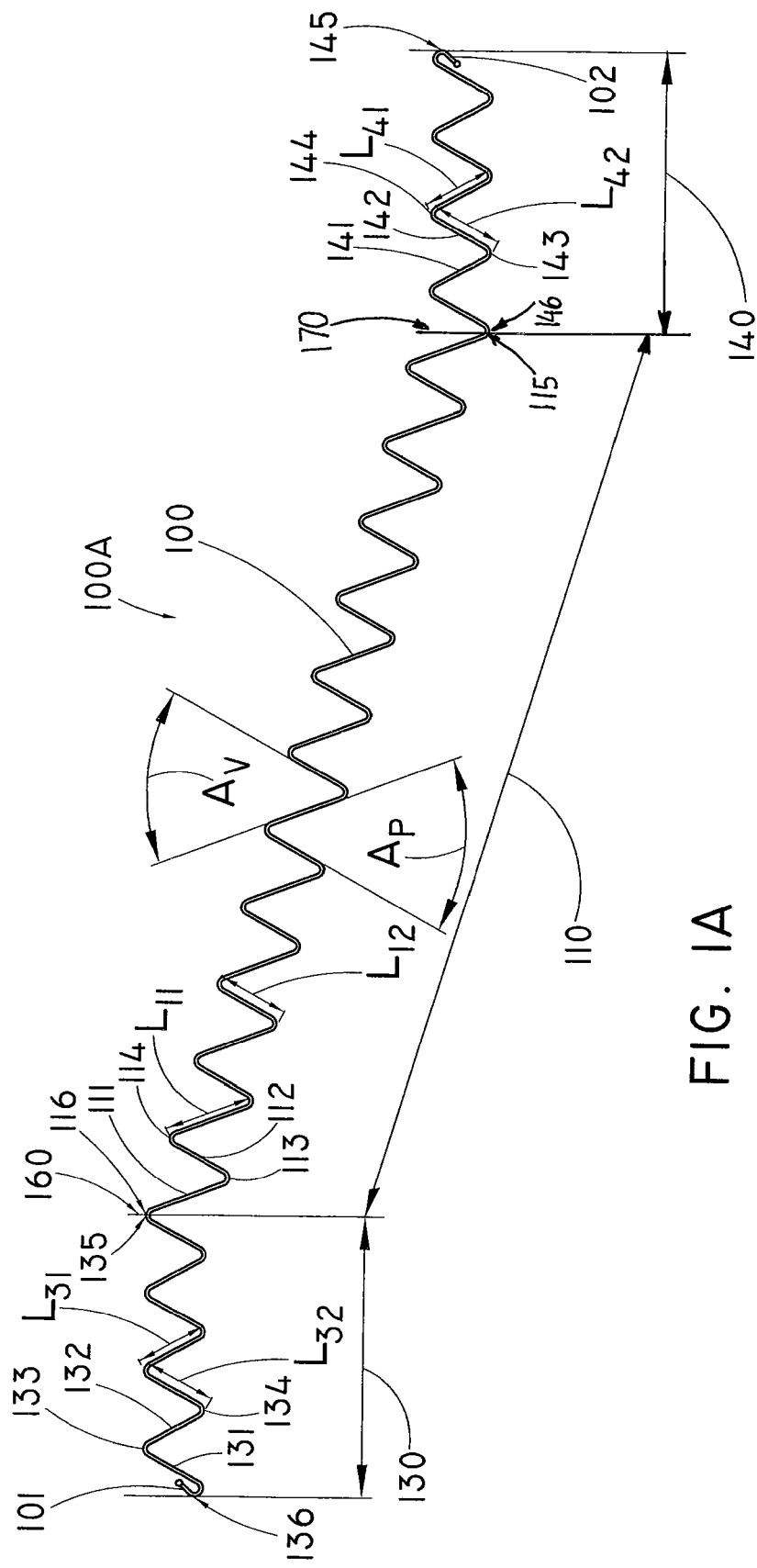
FIGS. 1(A-E) are top elevation views of preforms of medical devices.

Unless defined otherwise, all technical and scientific terms used herein have the same meaning as commonly understood to one of ordinary skill in the art to which this invention belongs.

The term "prosthesis" means any device for insertion or implantation into or replacement for a body part or function of that body part. It may also mean a device that enhances or adds functionality to a physiological system. The term prosthesis may include, for example and without limitation, a stent, stent-graft, filter, valve, balloon, embolization coil, and the like.

The term "tubular" refers to the general shape of an endoluminal device which allows the module to carry fluid along a distance or fit within a tubular structure such as an artery. Tubular prosthetic devices include single, branched, and bifurcated devices. Tubular may refer to any shape including, but not limited to, tapered, cylindrical, curvilinear, or any combination thereof. A tubular device may have a cross-sectional shape that is, circular, substantially circular or the like. However, it should be understood that the cross-sectional shape is not limited thereto, and other shapes, such as, for example, hexagonal, pentagonal, octagonal, or the like are contemplated.

The term "endoluminal" refers to or describes the internal or inside of a lumen, duct, and other passageways or cavities located in a human or other animal body. A lumen or a body passageway may be an existing lumen or a lumen created by surgical intervention. As used in this specification, the terms "lumen" or "body passageway," and "vessel" are intended to have a broad meaning and encompass any duct (e.g., natural or iatrogenic) or cavity within the human body and may include without limitation, blood vessels, respiratory ducts, gastrointestinal ducts, such as the biliary duct, intestines, the esophagus, the pericardial cavity, the thoracic cavity, the pericadial cavity, and the like. Accordingly, the terms "endoluminal device" or "endoluminal prosthesis" describe devices that can be placed inside or moved through any such lumen or duct.

The term "graft" or "graft material" describes an object, device, or structure that is joined to or that is capable of being joined to or implanted in or against a body part to enhance, repair, or replace a portion or a function of that body part. A graft by itself or with the addition of other elements, such as structural components, may comprise an endoluminal prosthesis. The graft may be comprised of a single material, a blend of materials, a weave, a laminate, or a composite of two or more materials. The graft may be constructed from natural or organic materials, for example and without limitation, a biological scaffold or bioremodelable material, such as small intestine submucosa ("SIS"), which is commercially available by Cook Biotech, West Lafayette, Ind. The graft may also be constructed from a synthetic, for example and without limitation, a polymer. The graft may be formed from a single layer or multiple layers of material. In embodiments employing a plurality of layers of material, the layers may remain separate, or may be attached to each other through a secondary process such as sintering, curing, adhesives, and sutures or the like.

The terms "patient," "subject," and "recipient" as used in this application may refer to any animal, particularly humans.

The term "helical" as used in this specification refers to any shape extending in a direction having both longitudinal and circumferential components, for example, a three-dimensional form or shape. Thus the term encompasses circular helixes, general helixes, cylindrical helixes, conic helixes, and the like. The helical shape may twist uniformly about a central axis, or may be asymmetrical. A helix may refer to a three-dimensional shape, commonly understood to be a spiral.

The term "preform" as used in the specification refers to an object or component that has been subjected to preliminary shaping before undergoing complete or final shaping.

"Longitudinally" refers to a direction, position or length substantially parallel with a longitudinal axis of a reference, and is the length-wise component of the helical orientation.

"Circumferentially" refers to a direction, position, or length that encircles a longitudinal axis of reference. The term "circumferential" is not restricted to a full 360° circumferential turn or to a constant radius.

Turning to the Figures, FIGS. 1A-D illustrate preforms of a medical device. As shown in FIGS. 1A-D, preforms 100A-D include an elongate member 100 extending between a first end 101 and a second end 102. The ends 101, 102 of the elongate member 100 may have a rounded atraumatic end. For example and without limitation, as shown in FIG. 14, the ends 101, 102 may terminate at an atraumatic ball 1401 or may have a hook-shaped bend 1402 terminating in an atraumatic ball 1401.

FIG. 1A illustrates an elongate member 100 including a uniform section 110, and end sections 130, 140. The uniform section 110 includes a first end 116 and a second end 115, as well as a plurality of first struts 112 and second struts 111. The first struts 112 have a length $L_{12}$ and the second struts have a length $L_{11}$. Each of the first struts 112 may have substantially the same length $L_{12}$ and each of the second struts substantially the same length $L_{11}$. In some embodiments, the length of the first struts $L_{12}$ may be longer than the length of the second struts $L_{11}$. In other embodiments, $L_{12}$ may be shorter than $L_{11}$.

Each of the plurality of first struts 112 and second struts 111 are connected in pairs at an angle through either peak bends 113 or valley bends 114. Each pair of first and second struts is comprised of a single first strut 112 and a single second strut 111 that are disposed adjacent each other and directly connected by either a peak bend 113 or a valley bend 114. Note that whether a bend is a "peak bend" or a "valley bend" is a matter of perspective, thus the terms "peak bend" and "valley bend" are not intended to be limited by orientation. Rather, "peak bends" denotes bends connecting a single pair of adjacent first and second struts 112, 111 at an angle $A_p$, while "valley bends" denote bends connecting a single pair of adjacent first and second struts 112, 111 at an angle $A_v$. In the embodiment shown in FIG. 1A, the first struts 112 and second struts 111 of the uniform section 110 are angled from each other at substantially the same angle $A_p$ at the peak bends 113, and the first and second struts 112, 111 at the valley bends 114 are angled from each other at substantially the same angle $A_v$. The angles $A_p$ at the peak bends 113 may be the same or different from angles $A_v$ at the valley bends 114. The angles $A_p$, $A_v$ may between about 20 and about 120 degrees, and in some embodiments may be between about 45 and about 90 degrees. The radius of curvature for the bends (peak and valley) may be about 0.019 inches (about 0.48 millimeters).

Each of the first and second struts 112, 111 may be connected to a peak bend 113 at one end and a valley bend 114 at the other end, such that the peak bends 113 and valley bends 114 and first and second struts 112, 111 form an undulating, zigzag pattern of alternating upwardly and downwardly oriented V-shaped sections. Note that while the peak and valley bends 113, 114 have been described as connecting the first and second struts 112, 111 in a "V-shape," other shapes are contemplated, for example and without limitation, "U-shape," sinusoidal shapes, curvilinear shapes, or the like. Moreover, while the first and second struts 112, 111 are depicted in the Figures as being straight, linear members, it should be understood that the struts may have a curved or otherwise non-straight line shape extending between adjacent peak and valley bends 113, 114.

The end sections 130, 140 are comprised of a plurality of first struts 131, 141 having lengths $L_{31}$ and $L_{41}$, respectively, and second struts 132, 142 having lengths $L_{32}$ and $L_{42}$, respectively. The end sections 130, 140 have first ends 136, 146 and second ends 135, 145, respectively. The end sections 130, 140 are connected at angles $A_p$, $A_v$ by peak bends 133, 143 and valley bends 134, 144. A second end 135 of the end section 130 is attached to the first end 116 of the uniform section 110, while a first end 146 of the end section 140 is attached to the second end 115 of the uniform section 110. Each of the first and second struts 131, 132 of the end section 130 may have substantially the same length, and the first and second struts 141, 142 of the end section 140 may have substantially the same length. That is, the length $L_{31}$ of each of the first struts 131 of the end section 130 may be substantially the same as the length $L_{32}$ of each of the second struts 132, and the length $L_{41}$ of each of the first struts 141 of the end section 140 may be substantially the same as the length $L_{42}$ of each of the second struts 142. The length $L_{31}$ and $L_{32}$ of the first and second struts 131, 132 of the end section 130 may be the same or different from the lengths $L_{41}$, $L_{42}$ of the first and second struts 141, 142 of the end section 140. Each pair the first and second struts 132, 131 of the end section 130 may be angled away from each other at the peak bends 133 at substantially the same angle $A_p$, and each pair of first and second struts 132, 131 may be connected at the valley bends 134 at the same angle $A_v$. The angles $A_p$ at the peak bends 133 may be the same or different from the angles $A_v$ at the valley bends 134.

Similarly, each pair of first and second struts 141, 142 for the end section 140 may be connected at peak bends 143 and angled away from each other at substantially the same angle $A_p$, while each pair of first and second struts 141, 142 may be connected at the valley bends 144 at substantially the same angle $A_v$. The angles $A_p$ at the peak bends 143 may be the same or different from the angles $A_v$ at the valley bends 144. In one embodiment the angles $A_p$ at peak bends 133 of end section 130 are substantially the same and the angles $A_v$ at valley bends 134 are substantially the same, and the angles $A_p$ at peak bends 143 of end section 140 are substantially the same and the angles $A_v$ at valley bends 144 are substantially the same.

Figure 1B:
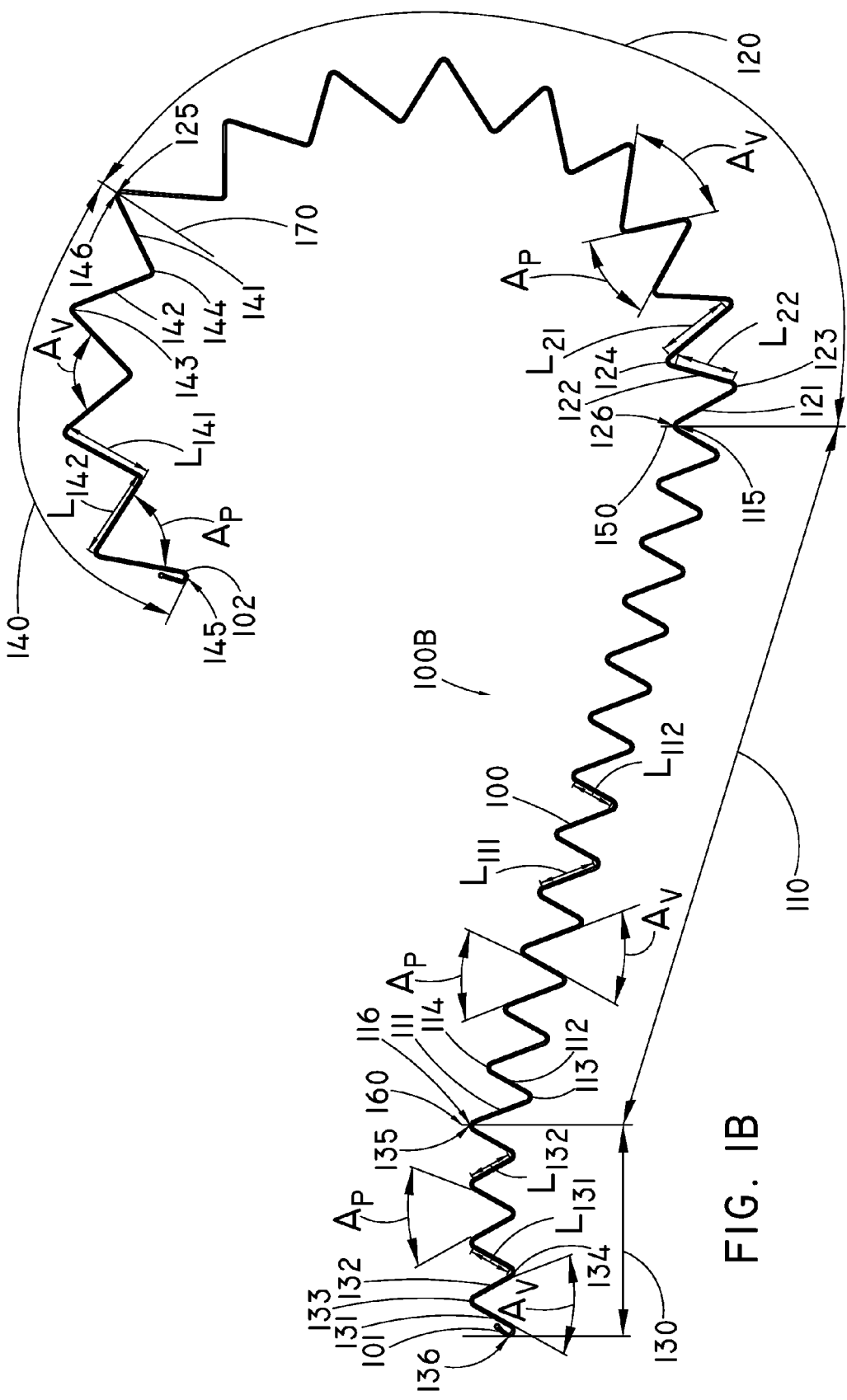

FIG. 1B illustrates a preform 100B comprising an elongate member 100 including a uniform portion 110, a curved portion 120, and end portions 130, 140. The uniform portion 110 and the end portion 130 are substantially the same as those of FIG. 1A, and will therefore not be described again.

As shown in FIG. 1B, the curved section 120 includes a plurality of first struts 121 having a length $L_{21}$ and a plurality of second struts 122 having a length $L_{22}$. Each of the plurality of first struts 121 and second struts 122 are connected in pairs at angles $A_p$, $A_v$ through either peak bends 123 or valley bends 124. Each pair of first and second struts 121, 122 are comprised of a single first strut 121 and a single second strut 122 disposed adjacent each other. The single first strut 121 and the single second strut 122 are directly connected by a bend. Each pair of first and second struts 121, 122 may be connected at one end to a peak bend 123 and at the other end to a valley bend 124, such that the peak bends 123 and valley bends 124 and plurality of first and second struts 121, 122 form an alternating pattern having an undulating, zigzag shape. In the embodiment shown in FIG. 1B, the length $L_{22}$ of the second struts 122 is less than the length $L_{21}$ of the first struts 121 in each pair of first and second struts 122, 121. Additionally, the length $L_{21}$, $L_{22}$ of the first and second struts 121, 122 increases moving in a direction from the first end 126 to the second end 125 along the curved section 120. The lengths $L_{22}$ and $L_{21}$ may increase for each successive pair of first and second struts 121, 122 moving in the direction from the first end 126 to the second end 125 of the curved section 120. In one embodiment the ratio between the length of the first and second struts $L_{21}$ and $L_{22}$ is substantially the same for each pair of first and second struts 121, 122. In another embodiment, the lengths $L_{21}$ and $L_{22}$ of each successive pair of first and second struts 121, 122 may be increased by a progressively smaller amount moving in the direction from the first end 126 toward the second end 125.

The angles $A_p$ at each of the peak bends 123 and the angles $A_v$ at each of the valley bends 124 may also increase moving in the direction from the first end 126 toward the second end 125 of the curved section 120. In one embodiment, the angles $A_p$, $A_v$ between pairs of first and second struts 121, 122 increases at each successive peak and valley bend 123, 124 moving in the direction from the first end 126 toward the second end 125 of the curved section 120. The angles $A_p$, $A_v$ between first and second struts 121, 122 at the peak and valley bends 123, 124 are between about 20 and about 120 degrees, and may be between about 45 and about 90 degrees. The radius of curvature for the bends (peak and valley) may be about 0.019 inches (about 0.48 millimeters).

Like end section 140 of FIG. 1A, end section 140 of FIG. 1B includes first and second struts 141, 142 having lengths $L_{41}$ and $L_{42}$, respectively, with the first and second struts 141, 142 being connected by peak and valley bends 143, 144. In one embodiment, the lengths $L_{42}$ and $L_{41}$ may be substantially the same, the angles $A_p$, $A_v$ between pairs of first and second struts 141, 142 at each of the valley bends 144 may be substantially the same, and the angles $A_p$ between first and second struts 141, 142 at each of the peak bends 143 may be substantially the same. However, unlike section 140 of FIG. 1A, the first and second struts 141, 142 are longer than the first and second struts 131, 132 of the end section 130, and the angles $A_v$ at the valley bends 144 are larger than the angles $A_p$ at the peak bends 143, thereby producing a substantially uniform and slightly curved shape along the length of the end section 140.

As with the uniform section 110 described above in connection with FIG. 1A, it should be understood that the peak and valley bends 123, 124, 143, 144 of the curved section 120 and the end section 140 may form a "V-shape," "U-shape," sinusoidal shape, curvilinear shape, or the like. Moreover, it should be understood that the first and second struts 121, 122, 141, 142 may have a curved, or otherwise non-straight line shape extending between adjacent peak and valley bends 123, 124, 143, 144.

Figure 1C:
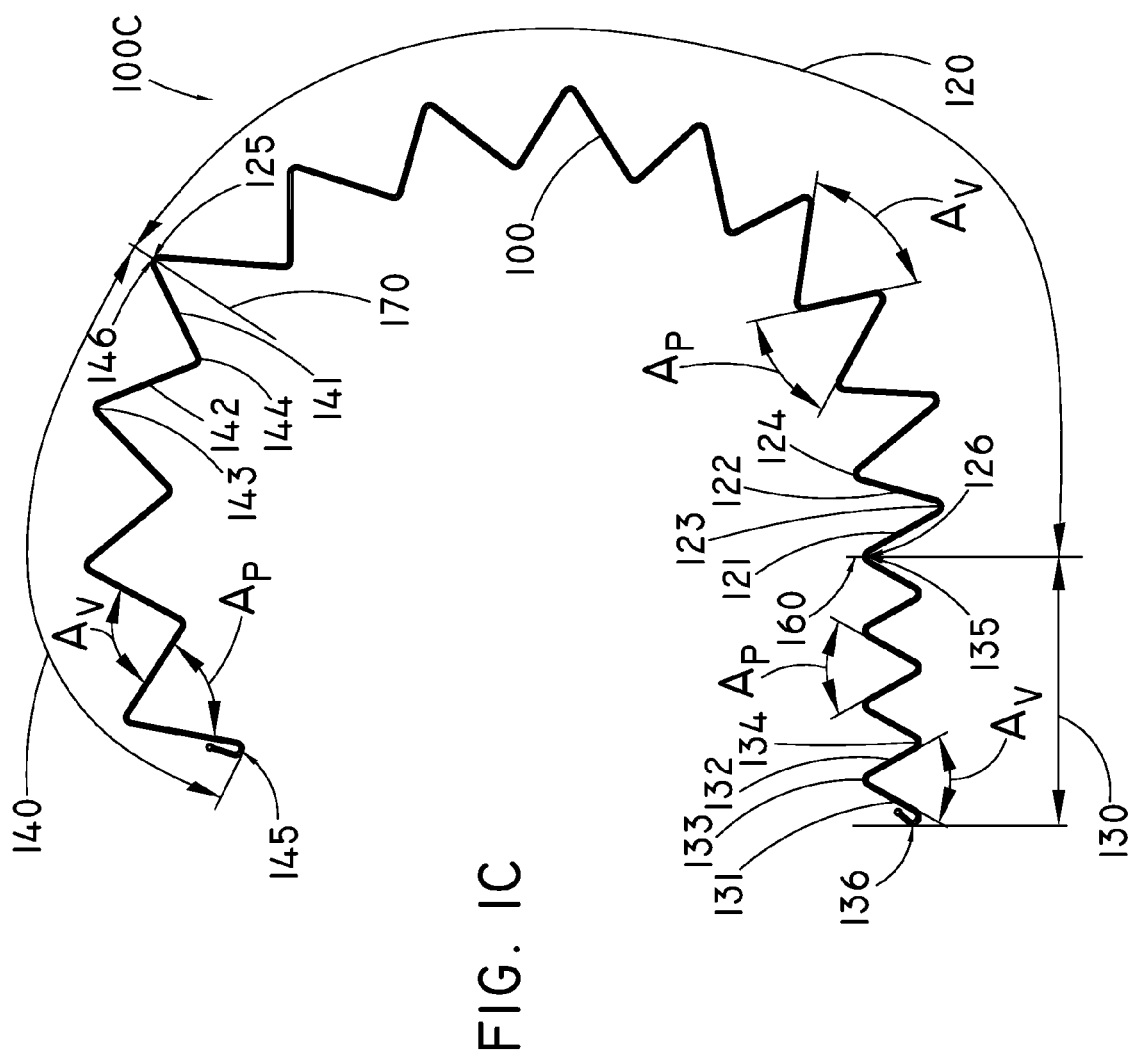

FIG. 1C illustrates a preform 100C including an elongate member including a curved section 120 and end portions 130 and 140 that are substantially the same as curved section 120 of FIG. 1B. Accordingly, the first and second struts 121, 131, 141, 122, 132, 142 and peak and valley bends 123, 133, 143, 124, 134, 144 and the relationships therebetween are substantially the same as those described above in connection with FIG. 1B.

Figure 1D:
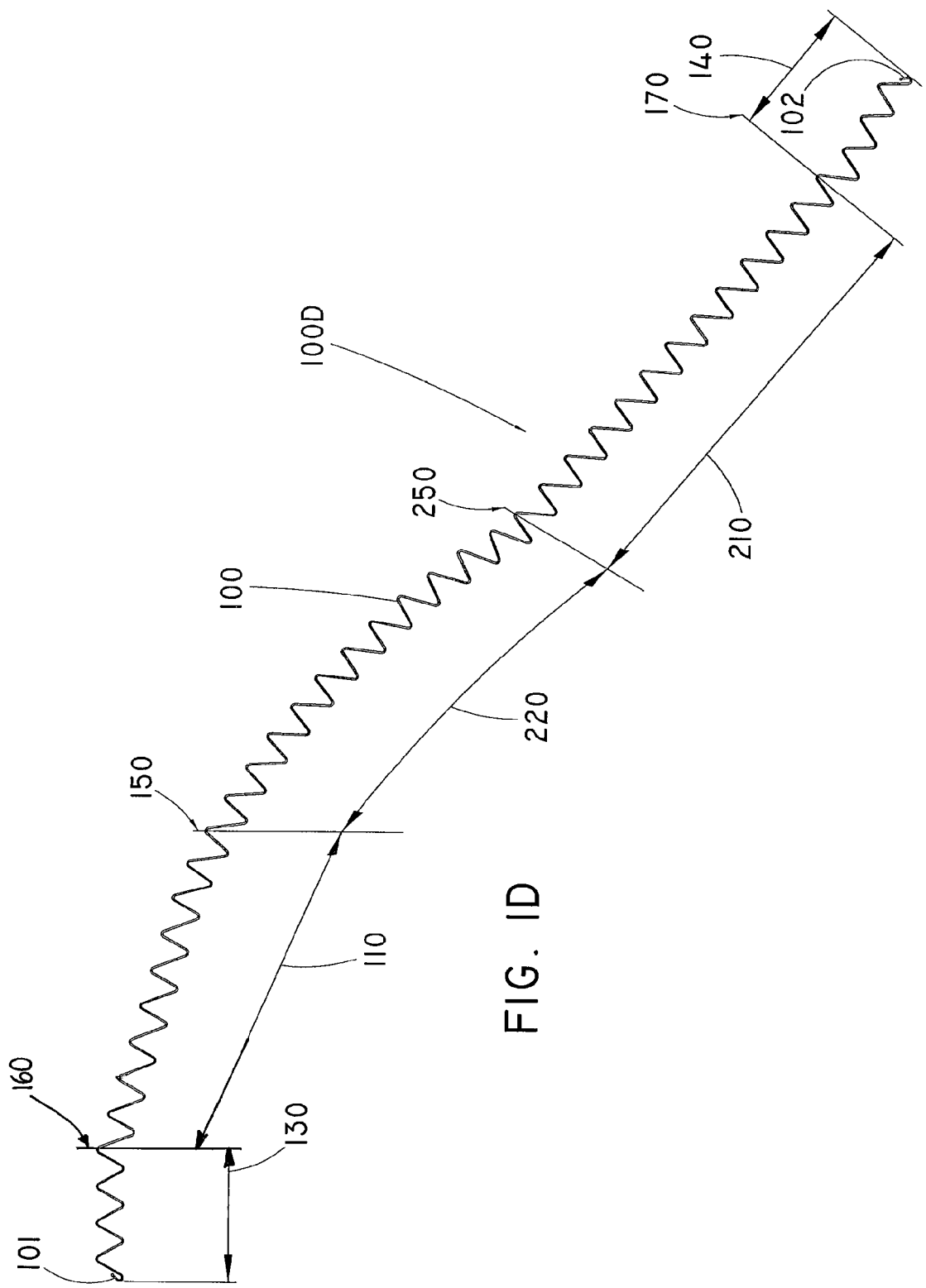
Figure 1E:
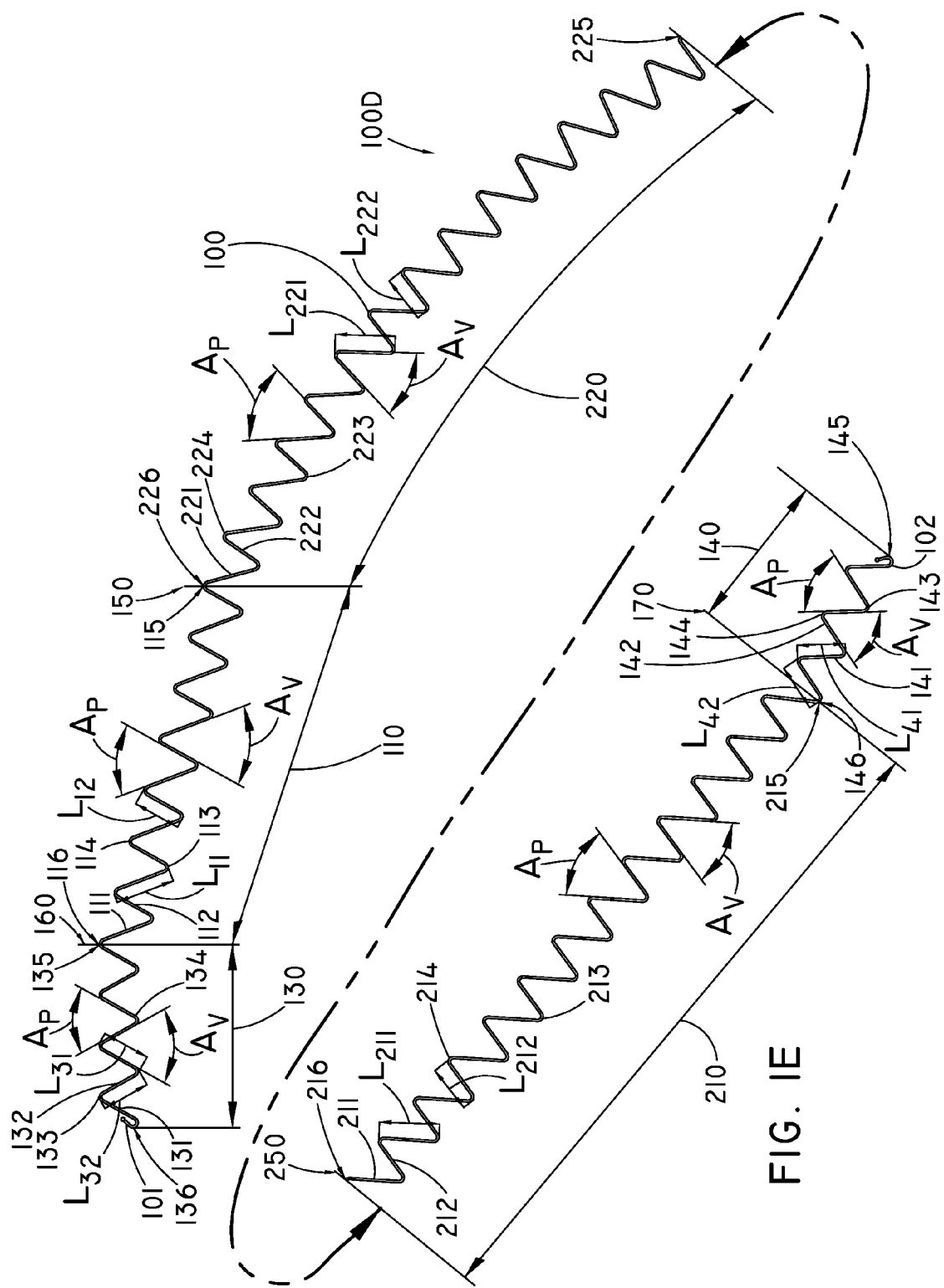

FIGS. 1D and 1E illustrate a preform 100D including an elongate member 100 having a first uniform section 110, an inverse-curved section 220, a second uniform section 210, and end portions 130, 140. As shown in FIG. 1E, the uniform sections 110, 210 include first ends 116, 216 and second ends 115, 215, as well as a plurality of first struts 111, 211 and second struts 112, 212. As with the uniform section 110 described in embodiments above, the first uniform section 110 includes a plurality of first struts 111 having a length $L_{11}$ and a plurality of second struts 112 having a length $L_{12}$. Each of the plurality of first struts 112 and second struts 111 are connected at angles $A_p$, $A_v$ through either peak bends 113 or valley bends 114 in pairs, with each pair comprised of a single first strut 111 and a single second strut 112 disposed adjacent each other. The single first strut 111 and the single second strut 112 are directly connected by a bend. The lengths $L_{11}$ and $L_{11}$ of the first and second struts 111, 112 may be substantially the same. The first struts 112 and second struts 111 may be angled from each other at substantially the same angle $A_p$ at the peak bends 113, and the first and second struts 112, 111 at the valley bends 114 may be angled from each other at substantially the same angle $A_v$. The angles $A_p$ at the peak bends 113 may be the same or different from the angles $A_v$ at the valley bends 114.

The second uniform section 210 includes a plurality of first struts 211 having a length $L_{211}$ and a plurality of second struts 212 having a length $L_{212}$. Each of the plurality of first struts 211 and second struts 212 are connected at angles $A_p$, $A_v$ through either peak bends 213 or valley bends 214 in pairs, with each pair comprised of a single first strut 211 and a single second strut 212 disposed adjacent each other. The single first strut 211 and the single second strut 212 may be directly connected by a bend. The lengths $L_{212}$ and $L_{211}$ of the first and second struts 211, 212 may be substantially the same and the first and second struts 211, 212 may be angled from each other at substantially the same angle $A_p$ at the peak bends 213. The first and second struts 211, 212 at the valley bends 214 may be angled from each other at substantially the same angle $A_v$. The angles $A_p$ at the peak bends 213 may be the same or different from the angles $A_v$ at the valley bends 214. In one embodiment the lengths $L_{11}$ and $L_{12}$ of the first and second struts of the first uniform section 110 may be greater than the lengths $L_{211}$ and $L_{212}$ of the first and second struts of the second uniform section 210. The angles $A_p$, $A_v$ at the peak bends 113 and the valley bends 114 of the first uniform section 110 may also be greater than the angles $A_p$, $A_v$ at the peak bends 213 and the valley bends 214 of the second uniform section 210.

The inverse-curved section 220 is substantially similar to the curved section 220 of FIG. 1B, however, the relationships between the angles $A_p$, $A_v$ at the peak and valley bends 223, 224 and the strut lengths $L_{222}$ and $L_{221}$ of the first and second struts 222, 221 along the length of the inverse-curved section 220 are reversed. Specifically, the lengths $L_{222}$, $L_{221}$ of the first and second struts 222, 221 may decrease moving in a direction from the first end 226 to the second end 225 along the inverse-curved section 220. In another embodiment, the lengths $L_{222}$ and $L_{221}$ may decrease for each successive pair of first and second struts 222, 221 moving in the direction from the first end 226 to the second end 225. In yet another embodiment, the lengths $L_{222}$ and $L_{221}$ of each successive pair of first and second struts 222, 221 may decrease by a progressively smaller amount moving in the direction from the first end 226 toward the second end 225.

The angles $A_p$ at each of the peak bends 223 and the angles $A_v$ at each of the valley bends 224 may decrease moving in the direction from the first end 226 toward the second end 225 of the inverse-curved section 220. In one embodiment, the angles $A_p$, $A_v$ between pairs of first and second struts 222, 221 may decrease at each successive peak and valley bend 223, 224 moving in the direction from the first end 226 toward the second end 225 of the curved section 220.

Like the end sections 130, 140 of FIG. 1A, the end sections 130, 140 of FIGS. 1D and 1E include first struts 131, 141 and second struts, 132, 142 having lengths $L_{31}$, $L_{41}$ and $L_{33}$, $L_{42}$, respectively, with the first struts 131, 141 and the second struts 132, 142 being connected by peak bends 133, 143 and valley bends 134, 144, respectively. The lengths $L_{32}$ and $L_{31}$ of end section 130 may be substantially the same, the angles $A_v$ between pairs of first and second struts 131, 132 at each of the valley bends 134 may be substantially the same, and the angles $A_p$ between first and second struts 131, 132 at each of the peak bends may be substantially the same. Additionally, the lengths $L_{42}$ and $L_{41}$ of end section 140 may be substantially the same, the angles $A_v$ between pairs of first and second struts 142, 141 at each of the valley bends 144 may be substantially the same, and the angles $A_p$ between first and second struts 142, 141 at each of the peak bends 143 may be substantially the same. The first and second struts 131, 132 of the end section 130 may be longer than the first and second struts 141, 142 of the end section 140. The angles $A_p$, $A_v$ between the first struts 111, 211, 221, 131, 141 and the second struts 112, 212, 222, 132, 142 at the peak bends 113, 223, 213, 133, 143 and valley bends 114, 224, 214, 134, 144, respectively, are between about 20 and about 120 degrees, and may be between about 45 and about 90 degrees. The radius of curvature for the bends (peak and valley) may be about 0.019 inches (about 0.48 millimeters).

As with the sections of the elongate member 100 described above in connection with FIGS. 1A-C, it should be understood that the peak and valley bends 113, 114, 133, 134, 223, 224, 143, 144 may have a "V-shape," "U-shape," sinusoidal shape, curvilinear shape, or the like. Moreover, it should be understood that the first struts 111, 211, 221, 131, 141 and second struts 112, 212, 222, 132, 142 may have a curved, or otherwise non-straight line shape extending between adjacent peak bends 113, 133, 213, 223, 143 and valley bends 114, 134, 214, 224, 144.

In each of the embodiments described above, the elongate member 100 may be made from a single continuous wire such that each of the sections shown in FIGS. 1A-1E are directly and continuously connected to form a single, unitary, monolithic structure. In such embodiments, the intersection, or transition/connection points 150, 160, 170, and 250 between sections of the preform 100 are transition bends that connect struts of adjacent sections. However, it should be understood that the elongate member 100 may be formed by connecting individual, separate sections that may be formed from the same or dissimilar materials, by soldering, welding, mechanical couplers, adhesives, or the like. In other embodiments, additional sections may be present between any of the sections described above.

Figure 20A:
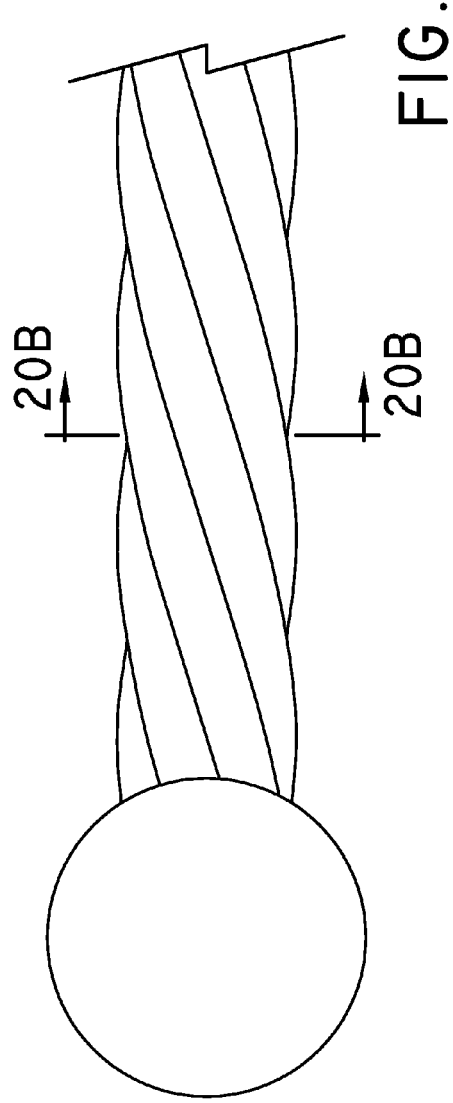
FIGS. 20A-B illustrate an alternative embodiment of the elongate member.
Figure 20B:
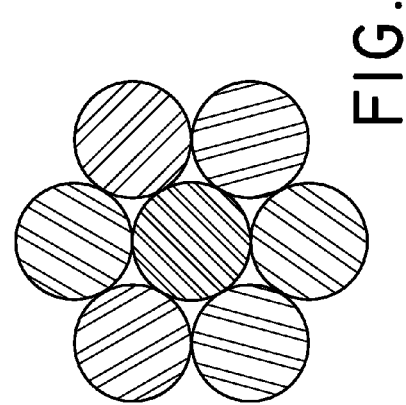

The elongate member 100 may be made from materials including polymers and metallic materials. Exemplary metallic materials include stainless steel, silver, platinum, palladium, gold, titanium, tantalum, iridium, tungsten, cobalt, chromium, cobalt-chromium alloy 1058, cobalt-based 35N alloy, nickel-based alloy 625, a molybdenum alloy, a molybdenum alloy including about 0.4% to about 0.8% of lanthanum oxide ($Li_2O_3$), and nickel-titanium alloys, such as Nitinol, or other suitable materials. The wire may have a diameter from about 0.007 to about 0.021 inches (about 0.18 millimeters to about 0.53 millimeters). In one embodiment, the elongate member is formed from a 0.014 inch (0.36 millimeters) diameter Nitinol wire. In an alternative embodiment shown in FIGS. 20A and 20B, the elongate member may be made from a plurality of filaments 2000, as described in co-pending U.S. Pat. App. No. 61/094,627, which is assigned to Cook Inc., the assignee of the present application, the entirety of which is hereby incorporated by reference.

In one embodiment of each of the preforms 100A-D, all, or substantially all, of the elements of the elongate member, including the first struts 111, 121, 131, 141, 221 the second struts 112, 122 132, 142, 222 the peak bends 113, 123, 133, 143, 223 and the valley bends 114, 124, 134, 144, 224 are formed in the same plane, thereby producing substantially mono-planar, flat preforms of a medical device.

In another embodiment shown in FIGS. 15A-D, the first struts 112, the second struts 111, the peak bends 113, and the valley bends 114 of the uniform section 110, are formed in the same plane 5, and at least end portions of the end sections 130, 140 curve away from the plane. Specifically, at least the peak bends 133, 143, valley bends 134, 144, and first and second struts 131, 141, 132, 142 of the end sections 130, 140 that are disposed near the first end 136 or the second end 145, respectively, may be curved away from the plane. At least some of the peak bends 133, valley bends 134, and first and second struts 131, 132 of the end section 130 may be curved in a generally cylindrical or conical shape having a radius $R_3$ that approximates, or is substantially the same as a radius of a portion of the three-dimensional graft member to which the end section 130 of the elongate member may be attached. Similarly, at least some of the peak bends 143, valley bends 144, and first and second struts 141, 142 of the end section 140 may be curved in a generally cylindrical or conical shape having a radius $R_4$ that approximates, or is substantially the same as, a radius of a portion of the three-dimensional graft member to which the end section 130 of the elongate member may be attached. Because the end sections 130, 140 are curved to approximate the three-dimensional shape of the graft, when the preform is attached to the graft it does not deform or compress the graft, thereby allowing the graft to maintain its desired shape. However, it should be understood that the embodiment is not limited thereto. For example, the end portions may curve away from the plane in any predetermined shape. Moreover, embodiments in which all the first and second struts 132, 142, 131, 141 and peak and valley bends 133, 143, 134, 144 curve away from the plane are also contemplated.

As illustrated in FIG. 15A, the end portion of the end section 130 may be formed in a single plane 7 that is oriented at an angle $\beta$ from the plane 5. Similarly, the end portion of the end section 140 may be formed in a single plane 6 that is oriented at an angle $\alpha$ from the plane 5. The angles $\alpha$ and $\beta$ may be the same or different, and may be less than, greater than, or equal to 90 degrees. While the embodiment shown in FIGS. 15A-D illustrates the preform 100A of FIG. 1A having end portions of the end sections 130, 140 that curve away from the plane, it should be understood the end sections 130, 140 of any of the embodiments of preforms disclosed herein may have similar curved end portions tailored to approximate the radius of the portion of the three-dimensional graft member to which the end sections 130, 140 are to be attached.

Figure 2:
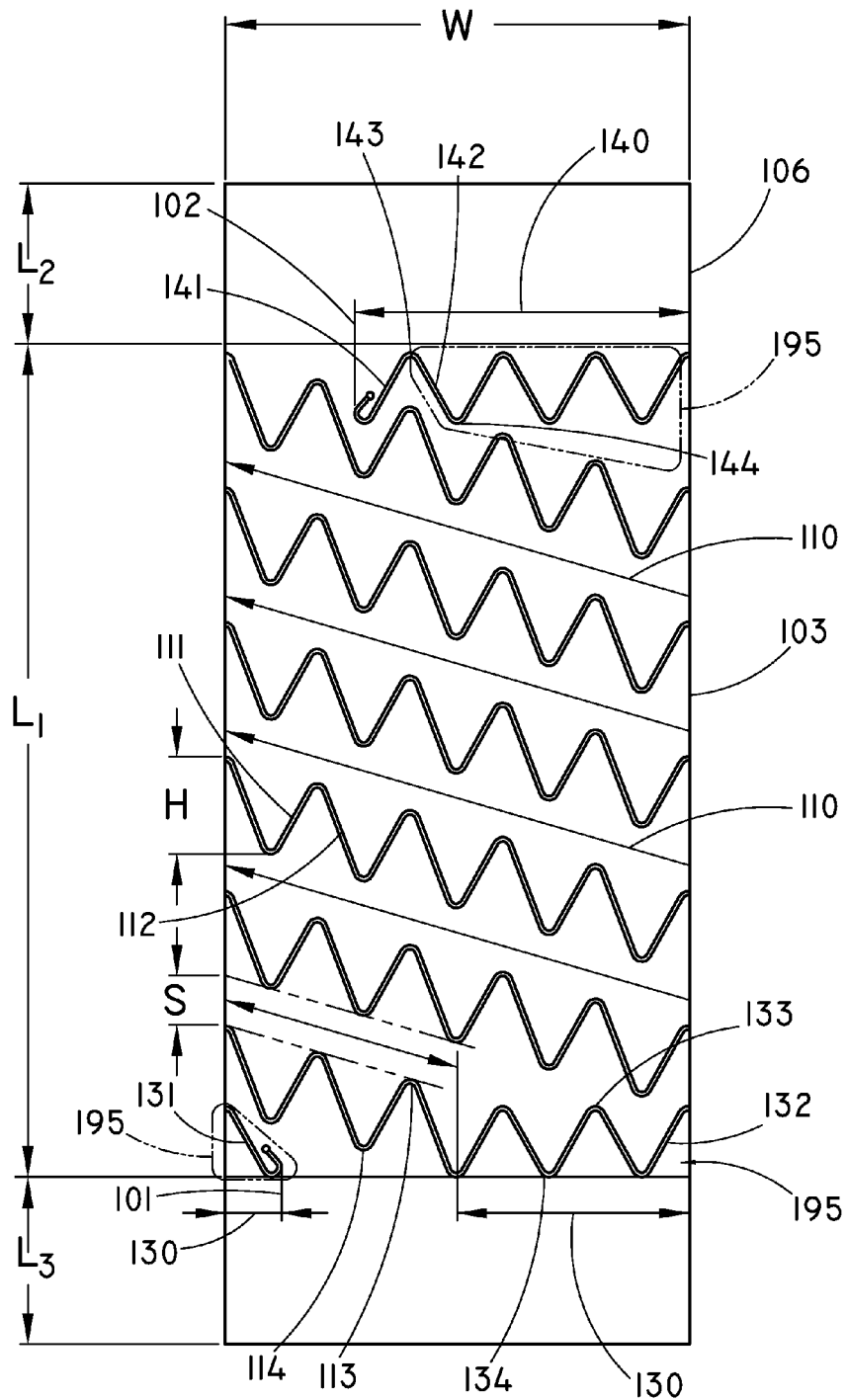
FIG. 2 is a design layout of the preform of FIG. 1A.

FIG. 2 illustrates a two-dimensional layout of a cylindrical graft material to which the preform 100A is to be attached. The two-dimensional layout represents a cylindrical graft that has been "sliced" longitudinally and rolled flat to form a generally quadrilateral shape. The two-dimensional graft layout may be used to determine the lengths of the first and second struts 111, 112, 131, 132, 141, 142 and angles $A_p$, $A_v$ of peak bends 113, 133, 143 and the valley bends 114, 134, 144 of the uniform section 110 and the end sections 130, 140 of the elongate member 100. The flattened graft layout has a width W that is defined by the equation W=πD, where D is the desired diameter of the graft when it is rolled into its cylindrical, three-dimensional form. The two-dimensional graft layout may be divided longitudinally into three portions: a straight portion 103 having a length $L_1$, where the straight portion 103 corresponds to a cylindrical portion of the graft in three-dimensional form around which the preform 100A is wrapped and attached; a first interface/sealing portion 106 having a length $L_2$, where the first interface sealing portion 106 corresponds to a first interface/sealing portion of the graft in three-dimensional form to which a first sealing stent is to be attached; and a second interface/sealing portion 105 having a length $L_3$, where the second interface/sealing portion 105 corresponds to a second interface/sealing portion 105 of the graft in three-dimensional form to which a second sealing stent is to be attached. However, it should be understood that the first and second interface/sealing portions 106, 105 may or may not be included depending on the desired application for the graft. The ends 101, 102 may angle toward a longitudinally adjacent peak bend 113 to prevent the ends 101, 102 from creating a structure that is potentially traumatic to the graft or a body vessel.

Initially, the number of peak bends 113 desired to span the width W of the straight portion 103 of the two-dimensional graft layout for each turn or row of the uniform section 110 of the preform 100A is determined. This number of peak bends 113 corresponds to the number of peak bends 113 that will be present for each turn or row of the preform 100A when the elongate member 100 is wrapped in a helical shape around the three-dimensional graft, which in this example has a substantially cylindrical shape. As used in this specification, the term "turn," "row," "helical turn," and "helical row" denote a series of connected struts and bends that span a total of 360 degrees around the circumference of the graft in its three-dimensional shape.

The number of desired peak bends 113 may be determined based on a desired radial support force to be provided by the preform 100A when it is wrapped in the helical shape and attached to the graft member. The number of peak bends 113 in each helical turn may be between about two and about nine bends depending on a number of different construction variables, including the size of the graft, etc. In one embodiment, the number of peak bends 113 in each helical turn may be between about 4 and about 6 bends, and may be five bends, as shown in the embodiment of FIG. 2.

Next, a desired spacing S between each helical turn of the elongate member 100 and a height H of each turn is determined based on a number of different construction variables. The height H may be between about four millimeters to about twelve millimeters, and the spacing S may be between about zero to about eight millimeters. In one embodiment, the spacing between turns S is about four millimeters, and the height of the turns H is about eight millimeters.

Once the number of peak bends 113, the height of the turns H, and the spacing between turns S have been determined, the peak bends 113 are placed horizontally across the width W of the two-dimensional graft layout at equal distances from each other such that the lateral spacing between peak bends 113 is determined by the relationship $W/n_p$, where W is the width of the two-dimensional graft and $n_p$ is the desired number of peak bends 113 in each helical turn. The peak bends 113 of each turn may be spaced such that they are laterally aligned with peak bends 113 of longitudinally adjacent turns/rows on the two-dimensional graft layout. This lateral alignment on the two-dimensional graft results in circumferential alignment of the peak bends 113 when the preform 100A is wrapped in a helical shape around, and attached to the three-dimensional graft.

The vertical placement of the peak bends 113 may be determined based on the combination of the height H, the spacing between turns S, and the pitch of the turns of the elongate member 100. As discussed above in connection with FIGS. 1A-D, each peak bend 113 and each valley bend 114 have an angle $A_p$ or $A_v$ that is between about 20 and about 120 degrees, and that may be between about 45 and about 90 degrees. The length $L_{12}$ of the first struts and the length $L_{11}$ of the second struts may be determined based on the desired height of the turns H and the angle $A_p$ of the peak bends 113 such that the first and second struts 111, 112 between the peak bends 113, which are disposed at the top of each helical turn, join at the valley bends 114 disposed at the bottom of each helical turn.

The angles $A_p$ of the peak bends 133, 143 of the end sections 130, 140 may be substantially the same as the angles $A_p$ of the peak bends 113, thereby allowing the peak bends 133, 143 to substantially laterally align with the peak bends 113 of longitudinally adjacent turns in the two dimensional graft layout, and to substantially circumferentially align with longitudinally adjacent turns in the three-dimensional graft when the end sections 130, 140 are wrapped in a cylindrical shape. The number of peak bends 133, 143 in the end sections 130, 140 may be less than the number of peak bends 113 in each turn of the elongate member 100 in the uniform section 110, thereby allowing the peak and valley bends 133, 143, 134, 144 and the first and second struts 131, 141, 132, 142 of the end sections 130, 140 to fill gaps 195 created by the helical layout of the turns of the uniform section 110 that are disposed at the upper and lower end portions of the straight portion 103. The lengths $L_{31}$, $L_{41}$ and $L_{32}$, $L_{42}$ of the first and second struts 112, 111 may be determined based on the angle $A_p$ of the peak bends 113, and the height H of the turns/rows of sections 130, 140 may be substantially the same as the height H of the turns of the uniform section 110. However, it should be understood that in other embodiments, the height H of the turns/rows of sections 130, 140 may be greater or less than the height H of the turns/rows of the uniform section 110.

Figure 3:
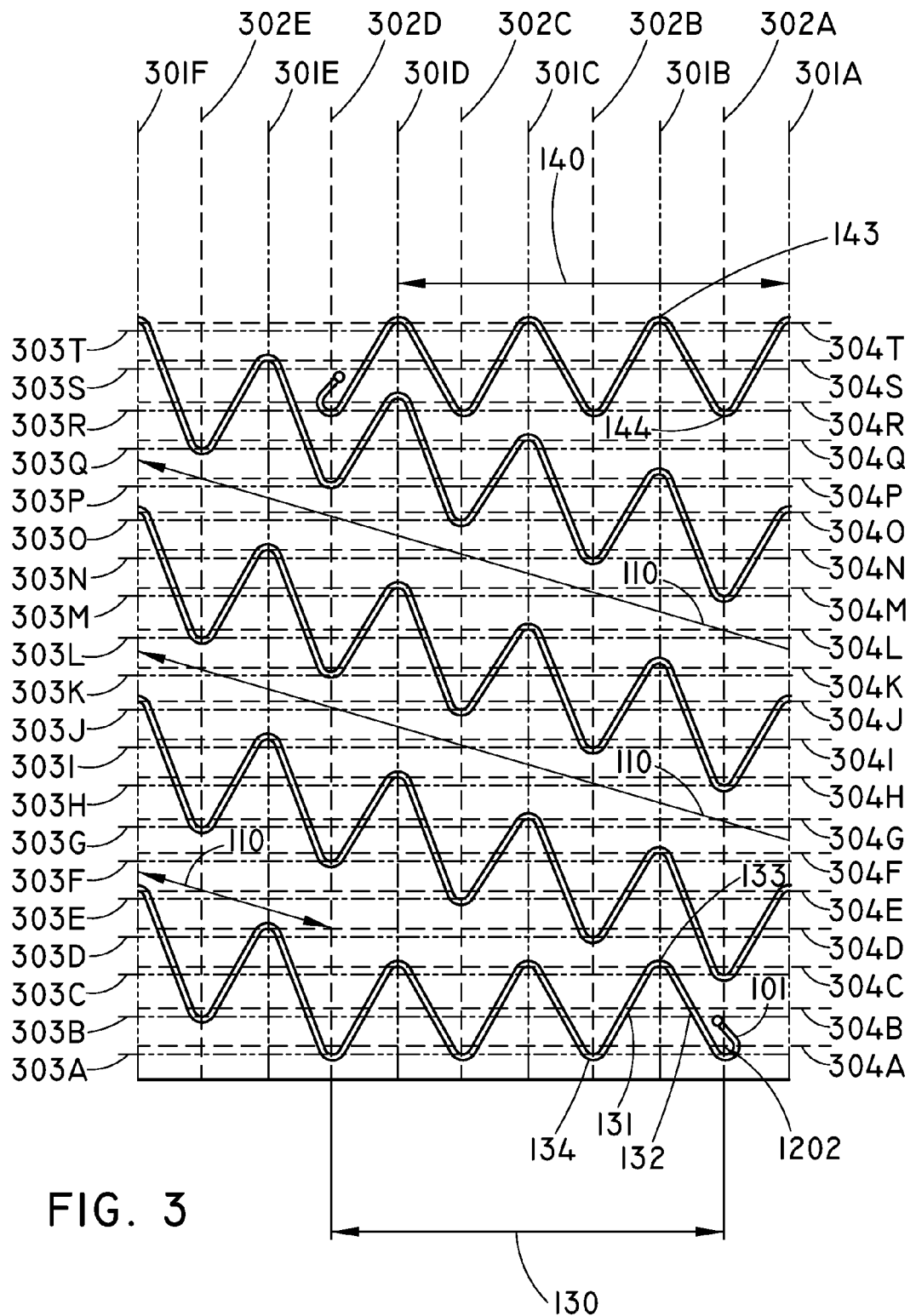
FIG. 3 is a detailed view of the design layout of FIG. 2.

FIG. 3 illustrates a detailed two-dimensional graft layout of the straight portion 103 used to determine the placement of the peak and valley bends 113, 133, 143, 114, 134, 144 of the uniform section 110 and end sections 140. As shown in FIG. 3, the straight portion 103 is divided into equally spaced horizontal alignment lines for peak bends 303A-T and valley bends 304A-T, as well as equally spaced vertical alignment lines for peak bends 301A-F and valley bends 302A-E. Initially, the center of the radius of the bend 1202 of the first end 101 of the elongate member 100 is placed at the intersection of valley bend alignment lines 302A and 304A. Next, the center of the radius for the first peak bend 133 of the end section 130 is placed at the intersection of peak bend alignment lines 303C and 301B, and each of the subsequent peaks bends 133 are placed at intersections between the vertical alignment lines 301C and 301D with horizontal alignment line 303C. The center of the radius for subsequent valley bends 134 are then placed at the intersection of valley bend alignment lines 304A and vertical alignment lines 302B-D.

Next, a center of the radius of each peak bend 113 of the straight section 103 is placed by moving up one horizontal alignment line 303 and moving to the left one vertical alignment line 301 from the previous peak bend 113. For example, the first peak bend 113 of the uniform section 110 is placed at the intersection between horizontal alignment line 303D and vertical alignment line 301E, and the second peak bend 113 is placed at the intersection between horizontal alignment line 303E and vertical alignment line 301F, and so on, moving in the direction from the first end 116 toward the second end 115 of the uniform section 110. Similarly, the center of the radius for each valley bend 114 is placed in the same manner moving up one horizontal alignment line 304 and to the left one vertical alignment line 302.

Next, a center of the radius of each peak bend 143 of the end section 140 is placed at intersections between the vertical alignment lines 301A-D and the horizontal alignment line 303V, while the center of the radius of each valley bend 144 is placed at intersections between the vertical alignment lines 302A-D and the horizontal alignment line 304T. Note that while the alignment/placement of the peak and valley bends has been described above with regard to the center of the radius of the peak and valley bends it is not limited thereto, and the peak and valley bends may be aligned based on the outer or inner edges of the actual bends themselves. Additionally, while the placement of the peak bends 113 and the valley bends 114 has been described above as being placed from right to left moving across the straight portion 103, it should be understood that the peak and valley bends 113, 114 may also be placed moving from left to right.

Once all the struts and bends of the elongate member 100 have been drawn on the two-dimensional graft layout, the struts and bends of each individual turn of the elongate member drawn on the two-dimensional graft layout are connected together moving in a direction from the first end 101 to the second end 102, resulting in the preform 100A of FIG. 1A.

Figure 4:
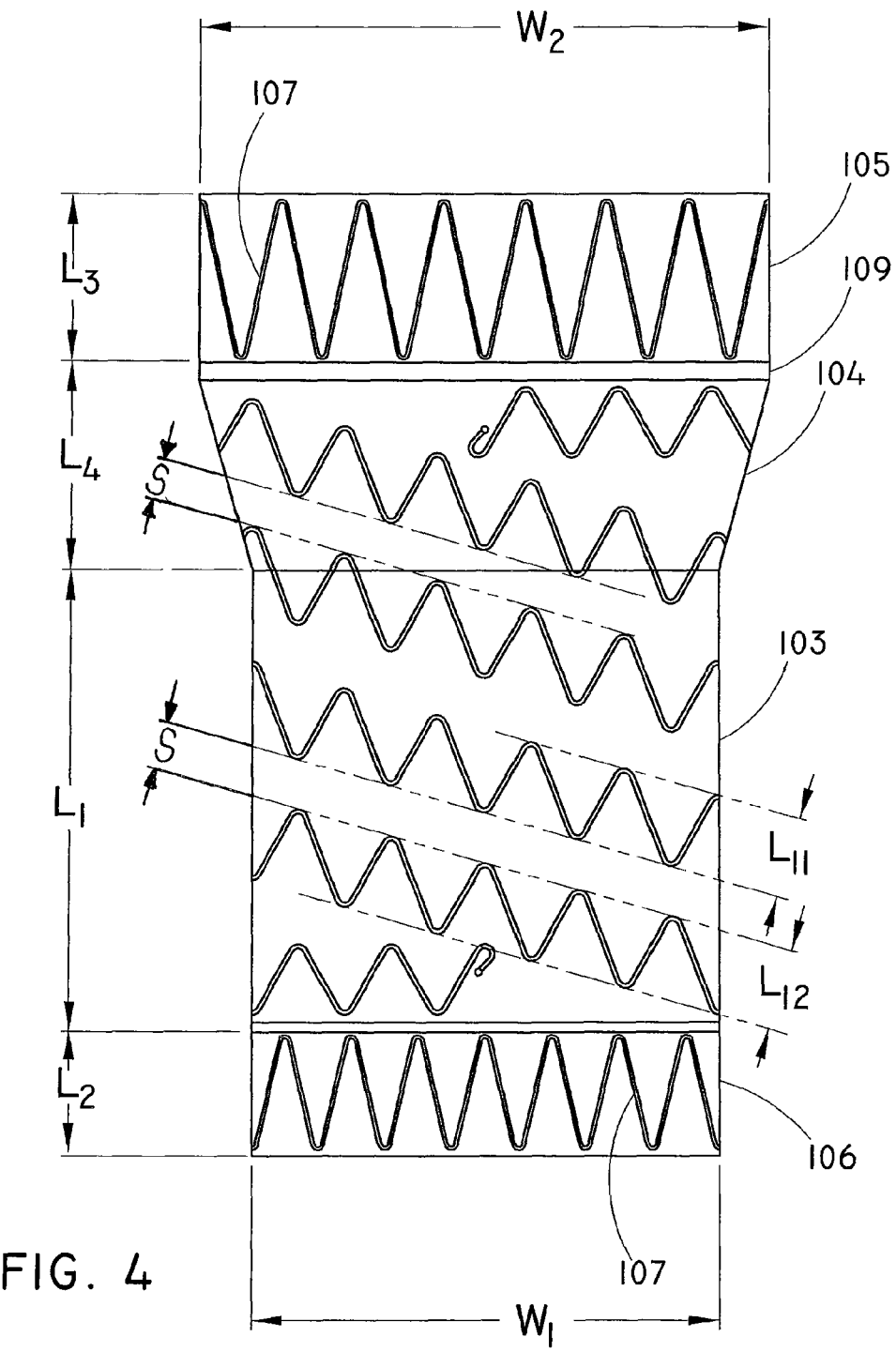
FIG. 4 is a design layout of the preform of FIG. 1B.
Figure 7:
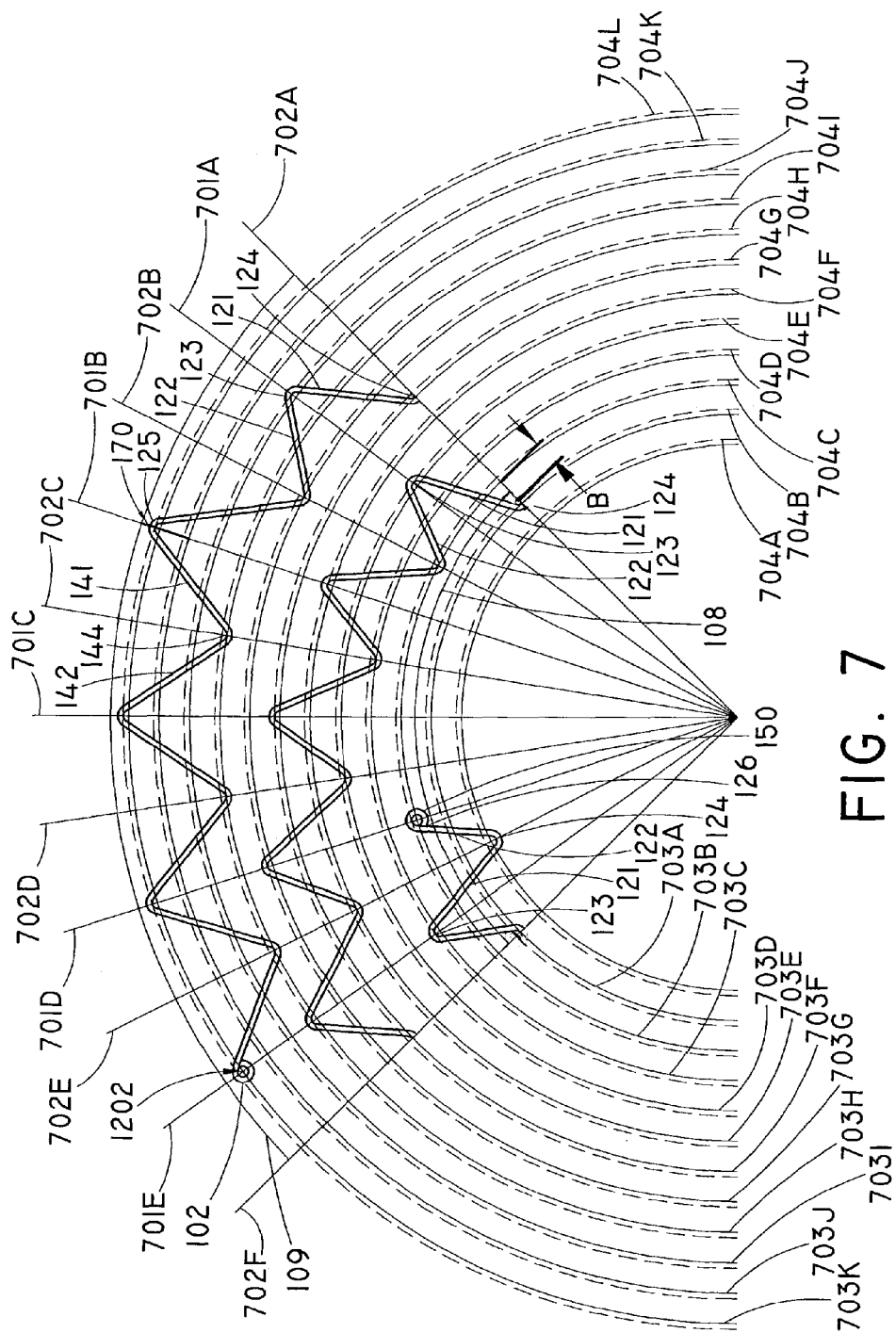
FIG. 7 is a detailed view of the design layout of the tapered, substantially conical portion of the graft member of FIG. 4 in a flat layout.

FIG. 4 illustrates a two-dimensional layout of a graft having a cylindrical shape corresponding to the straight portion 103, the interface/sealing portions 105 and 106, and a conical, tapered shape corresponding to the tapered portion 104, to which the preform 100B is to be attached. As with the two-dimensional layout of FIG. 2, the two-dimensional graft layout of FIG. 4 has been "sliced" longitudinally and rolled out to form the depicted shape. Note that the sliced and rolled out two-dimensional shape of the tapered portion 104 is shown as a trapezoidal shape in FIG. 4, however, because the tapered portion of the graft is conical, the laterally extending border of its two-dimensional shape are actually curved/arced, as shown in FIG. 7.

The two-dimensional graft layout is used to determine the lengths $L_{11}$, $L_{12}$, $L_{21}$, $L_{22}$, $L_{31}$, $L_{32}$, $L_{41}$, $L_{42}$ of the first and second struts 111, 112, 121, 122, 131, 132, 141, 142 and angles $A_p$, $A_v$ of peak bends 113, 123, 133, 143 and the valley bends 114, 124, 134, 144 of the uniform section 110, the curved section 120, and the end sections 130, 140 of the elongate member 100, respectively. The straight portion 103 and the second interface sealing portion 105 have a width $W_1$ that is defined by the equation $W_1=\pi D$, where D is the desired diameter of the straight and second interface sealing portions 103, 105 when the graft is rolled into its cylindrical, three-dimensional form.

Figure 6:
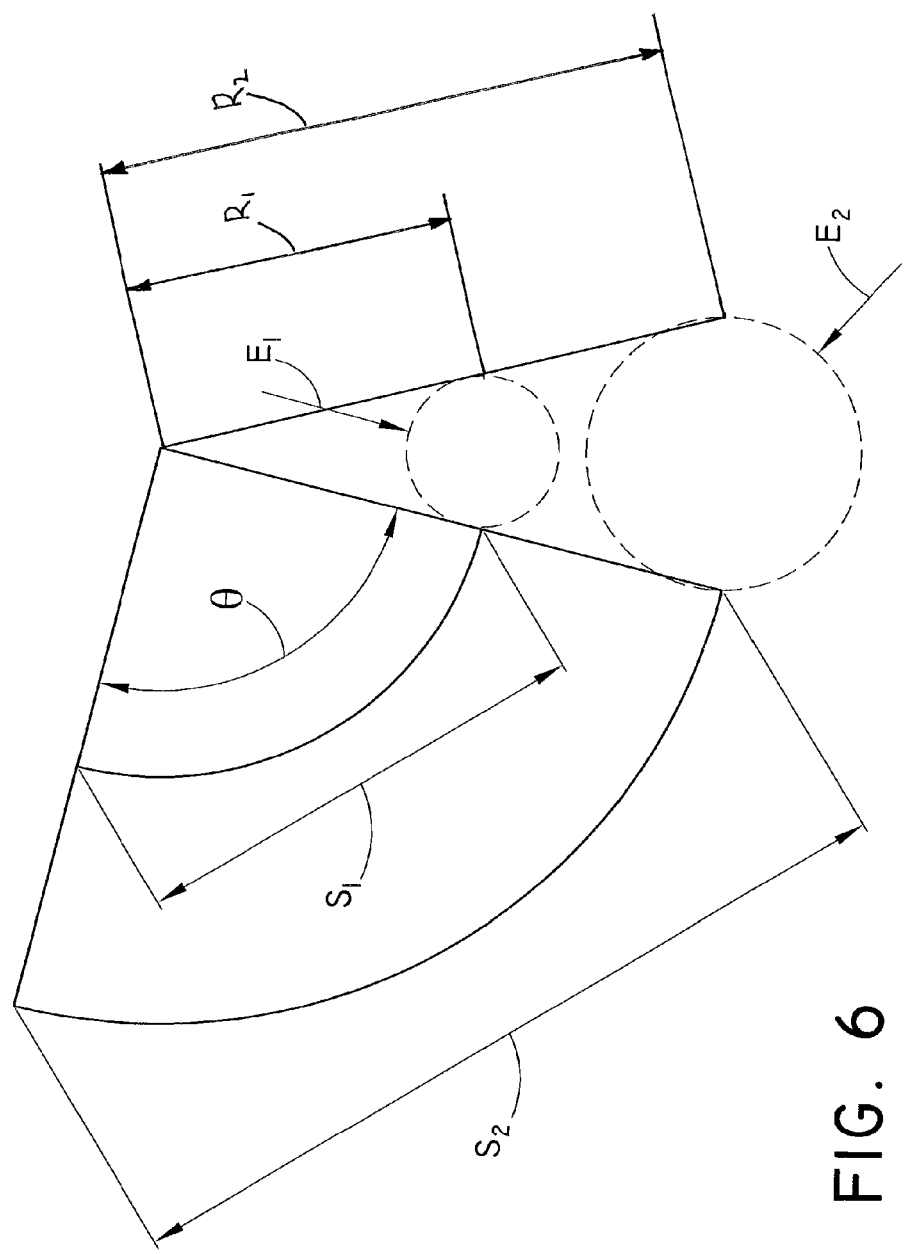
FIG. 6 is a detailed view of a portion of the design layout of FIG. 4 that corresponds to a tapered, substantially conical portion of the graft member of FIG. 4 in a flat layout.

As shown in FIG. 6, an arc length $S_1$ of the tapered portion 104 at the transition line 108 between the straight portion 103 and the tapered portion 104 is equal to the width $W_1$. The arc length $S_2$ at the transition line 109 between the second interface/sealing portion 105 and the tapered portion 104 is equal to the width $W_2$ of the second interface/sealing portion 105 (i.e. the desired circumference of the second interface/sealing portion 105 in its three-dimensional form). The angle θ, which defines the arc lengths $S_1$ and $S_2$ is calculated using the formula $\theta=S_1/R_1$, where $S_1$ is the arc length defined above. $R_1$ is determined by measuring the distance from a vanishing point to the center of a first circle $E_1$ having a diameter that is equal to the desired diameter of the straight portion 103 of the three-dimensional graft. The vanishing point is determined by the intersection of two lines drawn tangentially to the surfaces of the first circle $E_1$ and a second circle $E_2$ having a diameter that is equal to the diameter of the second interface/sealing portion 105 of the three-dimensional graft. The second circle is separated from the first circle by the length $L_4$ of the tapered portion 104, which is equivalent to the desired length of the tapered portion of the three-dimensional graft.

Returning to FIG. 4, the straight portion 103 has a length $L_1$, the first interface/sealing portion has a length $L_2$, to which a first sealing stent 107 is to be attached, and the second sealing/interface portion has a length $L_3$, to which a second sealing stent 107 is to be attached. However, it should be understood that the first and second interface/sealing portions 106, 105 may or may not be included depending on the application of the graft.

As described above in connection with FIG. 2, the number of peak bends 113, 123 of the straight portion 103 and the tapered portion 104 are determined based on a desired radial support force of the three-dimensional graft when the preform 100B is wrapped in the helical shape and attached thereto. The number of peak bends 113, 123 in each helical turn may be between about two and about nine bends, depending on a number of different construction variables, for example, the size of the graft, etc. The number of peak bends 113, 123 in each helical turn of the elongate member 100 may be between about four to about six, and in the embodiment of FIG. 4, the number of peak bends 113, 132 is five. The height H may be between about four millimeters to about twelve millimeters, and the spacing S may be between about zero to about eight millimeters. In one embodiment, the spacing between turns S is about four millimeters, and the height of the turns H is about eight millimeters. Note that the height H of the turns/rows of sections 120, 130, and 140 may be greater or less than the height H of the turns/rows of the uniform section 110.

Once the number of peak bends 113, 123, the height of the turns H, and the spacing between turns S have been determined, the peak bends 113, 124 are placed horizontally across the width $W_1$ and the tapered portion 104 of the two-dimensional graft layout. Note that the positions of the peak bends 113, 133 and the valley bends 114, 134 and the lengths of the first and second struts $L_{11}$ and $L_{12}$ of the straight portion 103 and the first interface/sealing portion 106 are determined using the method of intersecting vertical peak bend alignment lines 501A-F, vertical valley bend alignment lines 502A-E, horizontal peak bend alignment lines 503A-T, and horizontal valley bend alignment lines 504A-T (shown in FIG. 5) in substantially the same manner as described above in connection with FIGS. 2 and 3, and are therefore not described again.

Figure 5:
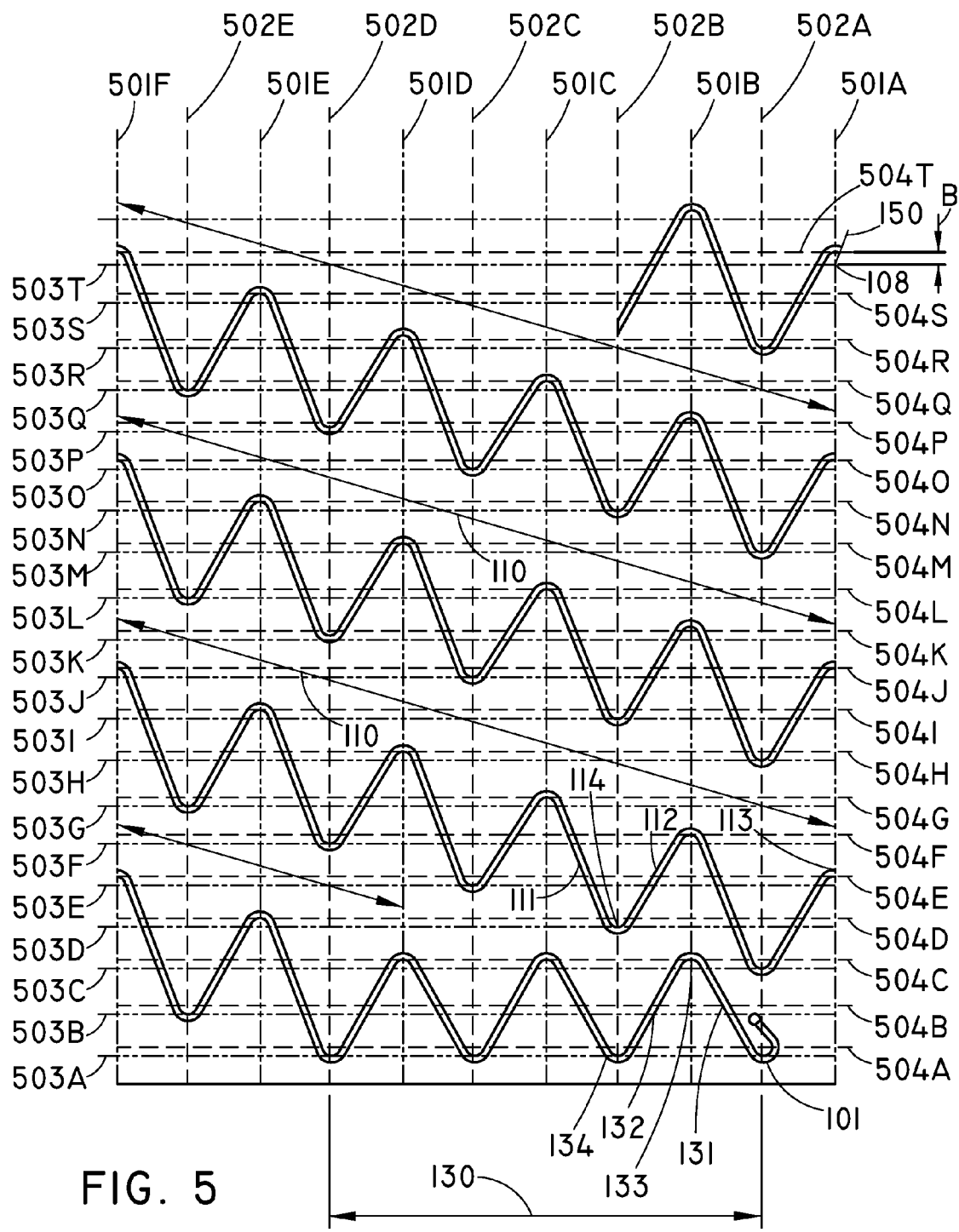
FIG. 5 is a detailed view of a portion of the design layout of FIG. 4 that corresponds to a substantially cylindrical portion of a graft member of FIG. 4 in a flat layout.

The curved section 120 begins at the transition point 150 between the uniform section 110 and the curved section 120, which coincides with the first peak bend 113 of the uniform section 110 that extends beyond the transition line 108 between the straight portion 103 and the tapered portion 104, as shown in FIG. 5.

Turning to FIG. 7, as with the straight portion 103, at least the peak bends 123 of the curved portion 104 are circumferentially aligned with the peak bends 113 of the straight portion 103. In some embodiments, both the peak bends 113, 123 and the valley bends 113, 123 of the straight portion 103 and the tapered portion 104 are circumferentially aligned. In other embodiments, every other peak bend 113, 123 and/or valley bend 113, 123 is aligned. In order to achieve this alignment, initially, the tapered portion is divided into equal portions based on the number of peak and valley bends 123, 124 by radial lines originating at an intersection point between two lines that are tangent to the right and left edges of the tapered portion 104. In this case, because there are a total of 5 peak bends 123 and 5 valley bends 124, the tapered portion is divided into 10 equal portions by radial lines. These radial lines are designated as radial peak bend alignment lines 701A-E and radial valley bend alignment lines 702A-F, which are arranged in an alternating pattern, as shown in FIG. 7. Next, a distance B that extends between the transition line 108, which is disposed between the straight portion 103 and the tapered portion 104, and the center of the radius of the first peak bend 113 protruding beyond the transition line 108 into the tapered portion, is measured on the two-dimensional graft layout. Concentric alignment circles are then drawn based on the same spacing S between turns and height H of the turns for peak bends 703A-K and concentric alignment circles for valley bends 704A-L. The first concentric alignment circles for peak bends 703A and valley bends 704A are drawn above an arc disposed above the transition line/arc 108 by the distance B.

A center of the radius of the first peak bend 123 of the tapered portion 104 is placed at the intersection between radial peak bend alignment line 701D and concentric peak bend alignment circle 703B, which coincides with transition point 150 between the uniform section 110 and the curved section 120. Each of the subsequent peak bends 123 are placed in a manner similar to the placement of the peak bends 113 in the straight portion 103. That is, the peak bends 123 are placed by moving up one concentric alignment circle 703 and moving to the left one radial alignment line 701 from the previous peak bend 123, moving in the direction from the first end 126 toward the second end 125 of the curved section 120. Similarly, the center of the radius of valley bends 124 are placed by moving up one concentric valley bend alignment circle 704 and to the left one radial valley bend alignment line 702. Note that in some embodiments, that the last peak bend 123 of the curved section 120 may be placed two concentric circles above the previous peak bend 123.

Once the final peak bend of the curved section 120 has been placed at the intersection of the concentric peak bend alignment circle 703K and the radial peak bend alignment line 701B, which coincides with the transition point 170 between the curved section 120 and the end section 140, a center of the radius of the first valley bend 144 of the end section 140 is placed at the intersection between radial valley bend alignment line 702C and concentric valley bend alignment circle 7041, which is disposed one valley bend alignment circle above that of the last valley bend 124 of the curved section 120. Subsequent valley bends 144 are placed at intersections between concentric peak bend alignment circle 7041 and radial peak bend alignment lines 702D-E. The peak bends 143 are placed at intersections between the concentric peak bend alignment circle 703K and the radial peak bend alignment lines 701C-E. The center of the radius of the bend 1202 is placed at the intersection between the concentric peak bend alignment circle 703K and the radial peak bend alignment line 701E.

Note that while the alignment/placement of the peak and valley bends has been described above with regard to the center of the radius of the peak and valley bends it is not limited thereto, and the peak and valley bends may be aligned based other features of the bends, for example and without limitation, the outer or inner edges of the actual bends themselves. Also note that the height H of the turns/rows of section 120 may be the same as, or greater or less than the height H of the turns/rows of the uniform section 110.

Once the all the struts and bends of the elongate member 100 have been drawn on the two-dimensional graft layout, the struts and bends of each turn of the elongate member are connected together moving in a direction from the first end 101 to the second end 102, resulting in the preform 100B of FIG. 1B.

Note that the positions of the peak bends 123, valley bends 124, and the first and second struts 121, 122 of the curved section 120, as well as the peak bends 133, 143, valley bends 134, 144, and the first and second struts 131, 132, 141, 142 of the end sections 130, 140 for the preform 100C may be determined in the same manner as described above with regard to the curved section 120 and end sections 130, 140 of the preform 100B.

Figure 8:
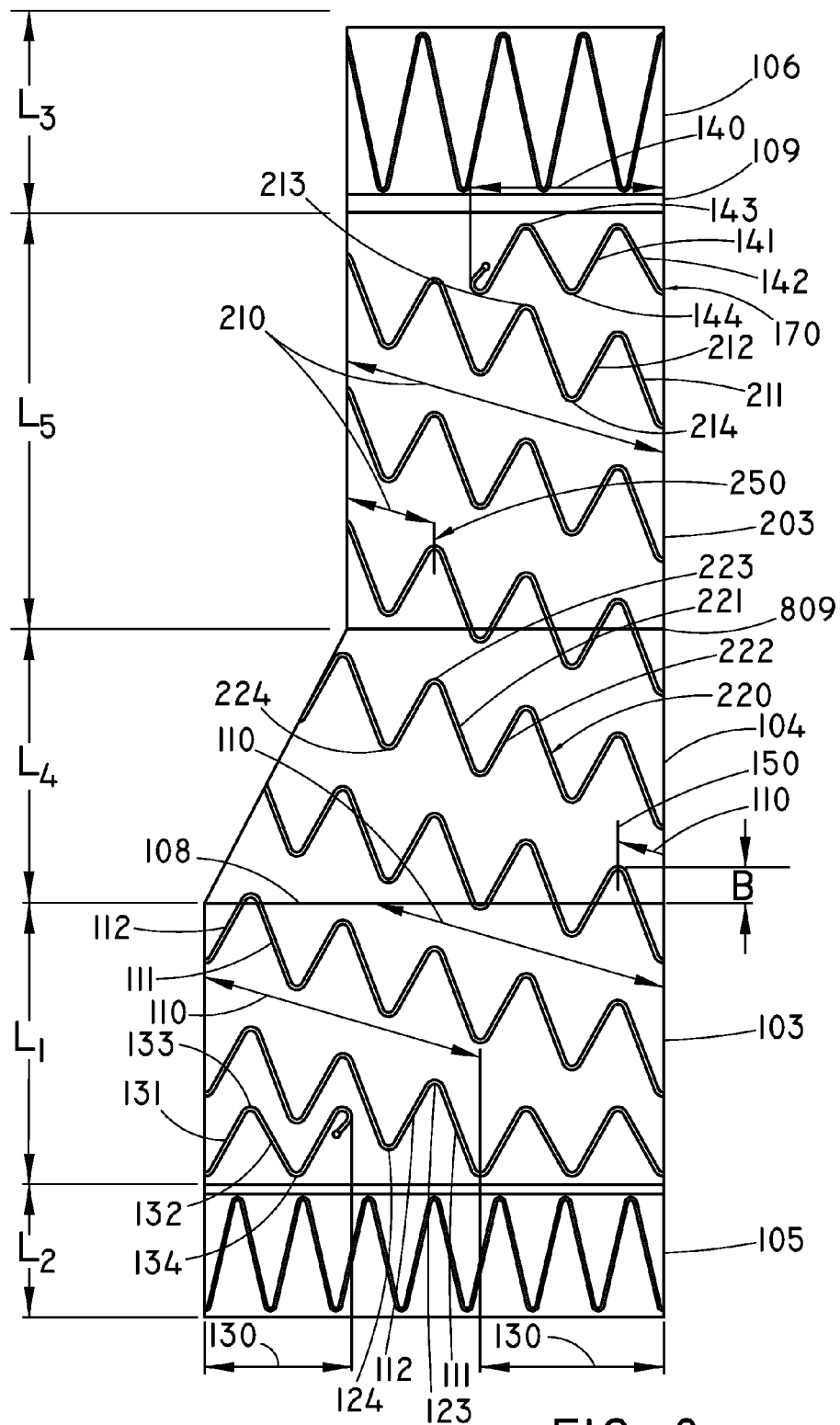
FIG. 8 is a design layout of the preform of FIGS. 1D and E.
Figure 9:
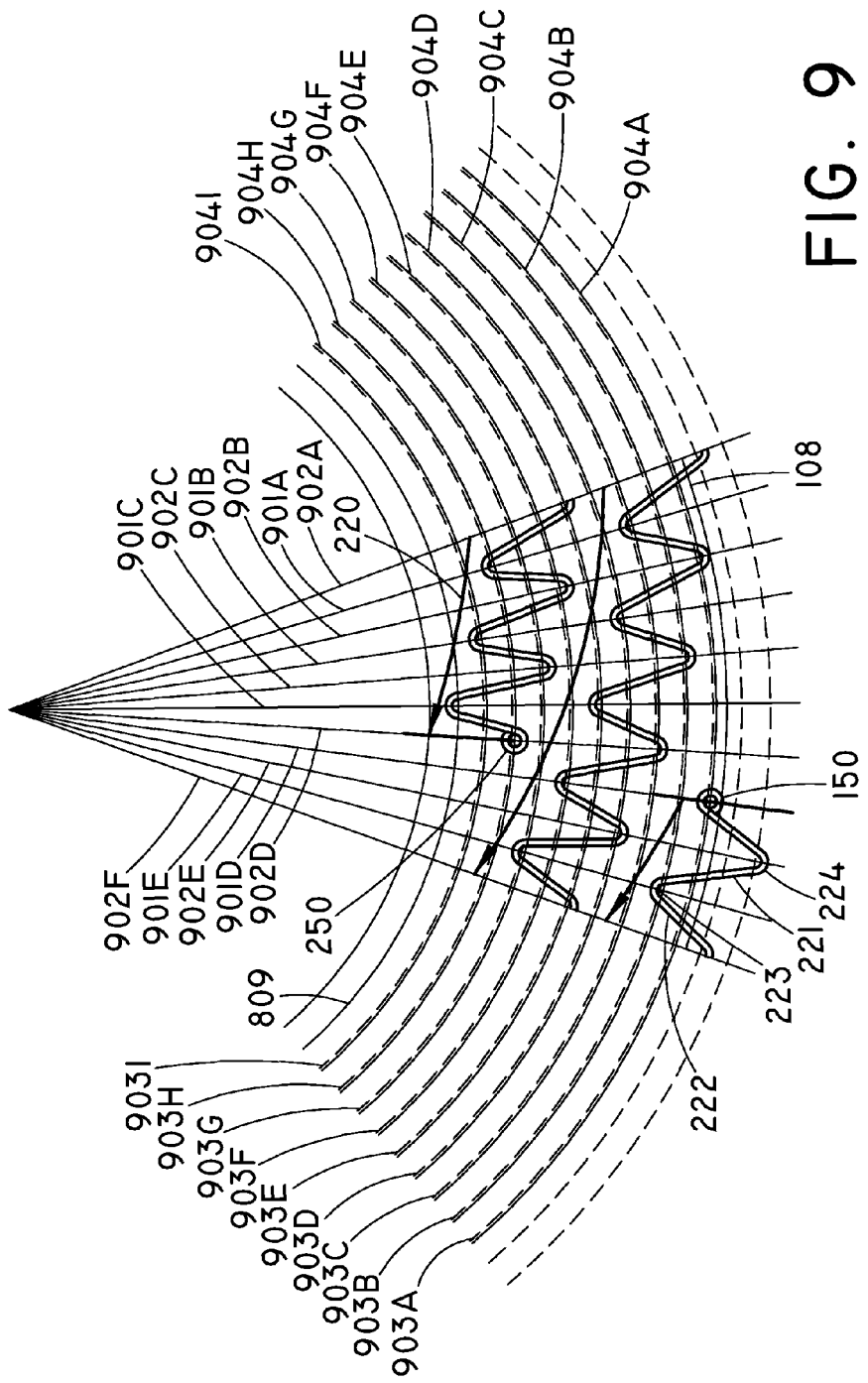
FIG. 9 is a detailed view of the design layout of the asymmetrical tapered portion of the graft member of FIG. 8 in a flat layout.

FIG. 8 illustrates a two-dimensional layout of a graft to which the preform 100D is to be attached. When in its three-dimensional shape, the graft shown in FIG. 8 may have a cylindrical shape corresponding to the first straight portion 103, the second straight portion 203 (transition line 809 represents the border between the second straight portion 203 and the second sealing portion 105), and the interface/sealing portions 105, 106, and a conical, tapered shape corresponding to the tapered portion 104 (referred to as an inverse-curved portion above in connection with FIGS. 1D and 1E). As with the two-dimensional layout of FIG. 4, the two-dimensional graft layout of FIG. 8 has been "sliced" longitudinally and rolled flat to form the depicted shape. Note that the laterally extending borders of the sliced and flattened two-dimensional shape for the tapered portion 104 are shown as being straight in FIG. 8, however, in actuality, the two-dimensional shape of these borders are curved, as shown in FIG. 9. Also, while the tapered portion 104 is shown as an asymmetrical taper for ease of manufacturing, the tapered portion 104 may be formed as a symmetrical taper, such as the tapered section 104 of FIG. 4. Regardless of whether the tapered portion 104 is asymmetrical or symmetrical, the tapered portion is assumed to be symmetrical for purposes of calculating and determining the placement and angles $A_p$, $A_v$ of the peak and valley bends 223, 224 and the lengths $L_{222}$, $L_{221}$ of the first and second struts 222, 221.

Additionally, while the tapered portion 104 of FIG. 8 is shown as narrowing between the first and second straight portions 103, 803, as opposed to widening, as shown in the tapered portion 104 of FIG. 4, the method of determining bend placement and strut length is substantially the same as that described above, and results in narrowing angles at the bends and decreasing lengths $L_{222}$, $L_{221}$ for the first and second struts 222, 221 moving from the first end 226 toward the second end 225.

Note that the positions of the peak bends 113, 213, 223, 133, 143 and the valley bends 114, 224, 224, 134, 144 and the lengths $L_{11}$, $L_{12}$, $L_{222}$, $L_{221}$, $L_{31}$, $L_{32}$, $L_{41}$, $L_{42}$ of the first and second struts of the end section 130 and first uniform section 110 corresponding to straight portion 103, the inverse-curved portion 220 corresponding to tapered portion 104, the second uniform section 210 and end section 140 corresponding to the second straight portion 803, are determined using the same method of intersecting vertical peak bend alignment lines, vertical valley bend alignment lines, horizontal peak bend alignment lines, horizontal valley bend alignment lines, concentric peak bend alignment circles 903A-K (shown in FIG. 9), concentric valley bend alignment circles 904A-K, radial peak bend alignment lines 901A-E, and radial valley bend alignment lines 902a-f described above in connection with FIGS. 4-7, and are therefore not described again.

Figure 10:
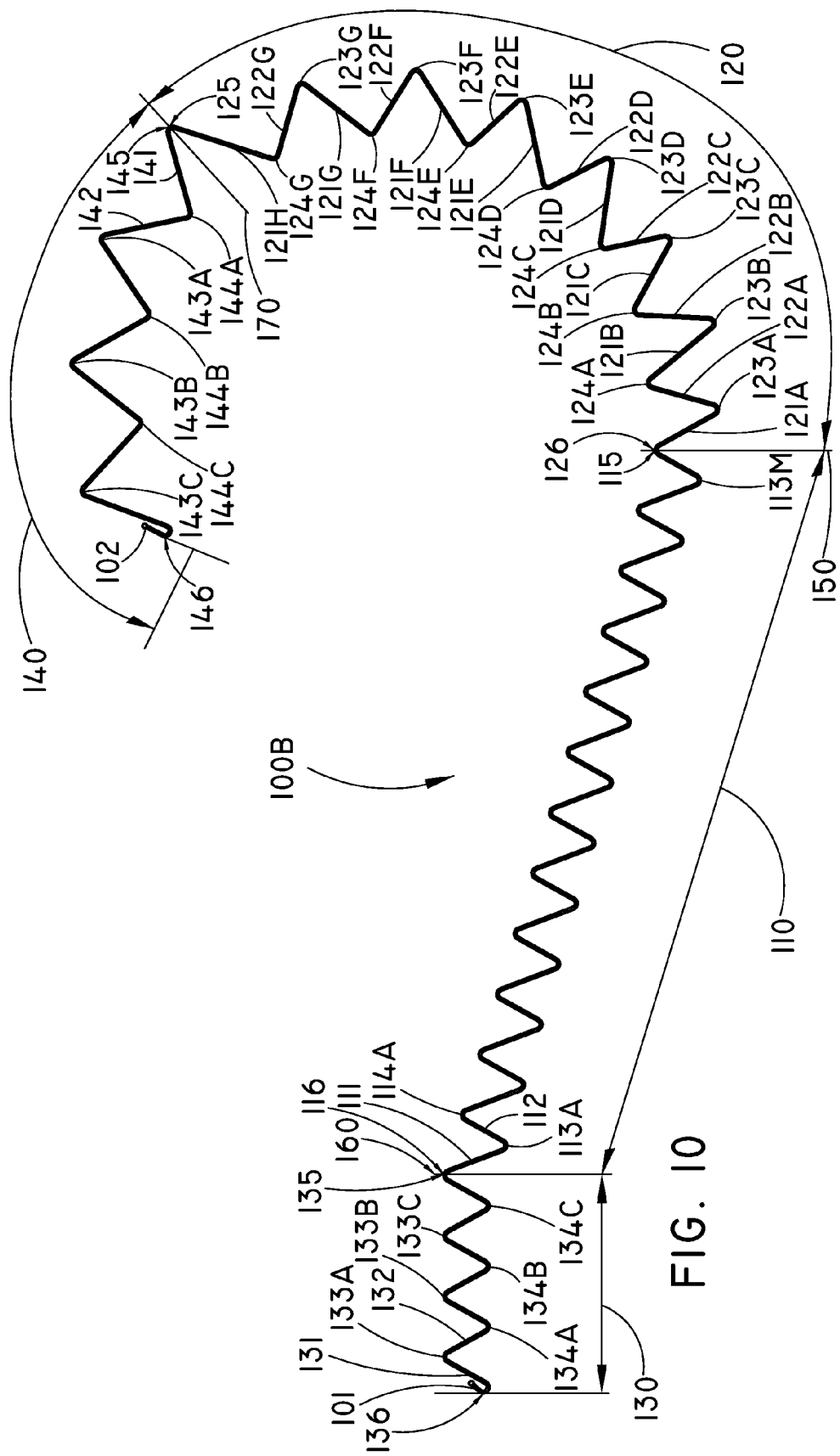
FIG. 10 is a detailed view of the preform of FIG. 1B.
Figure 11:
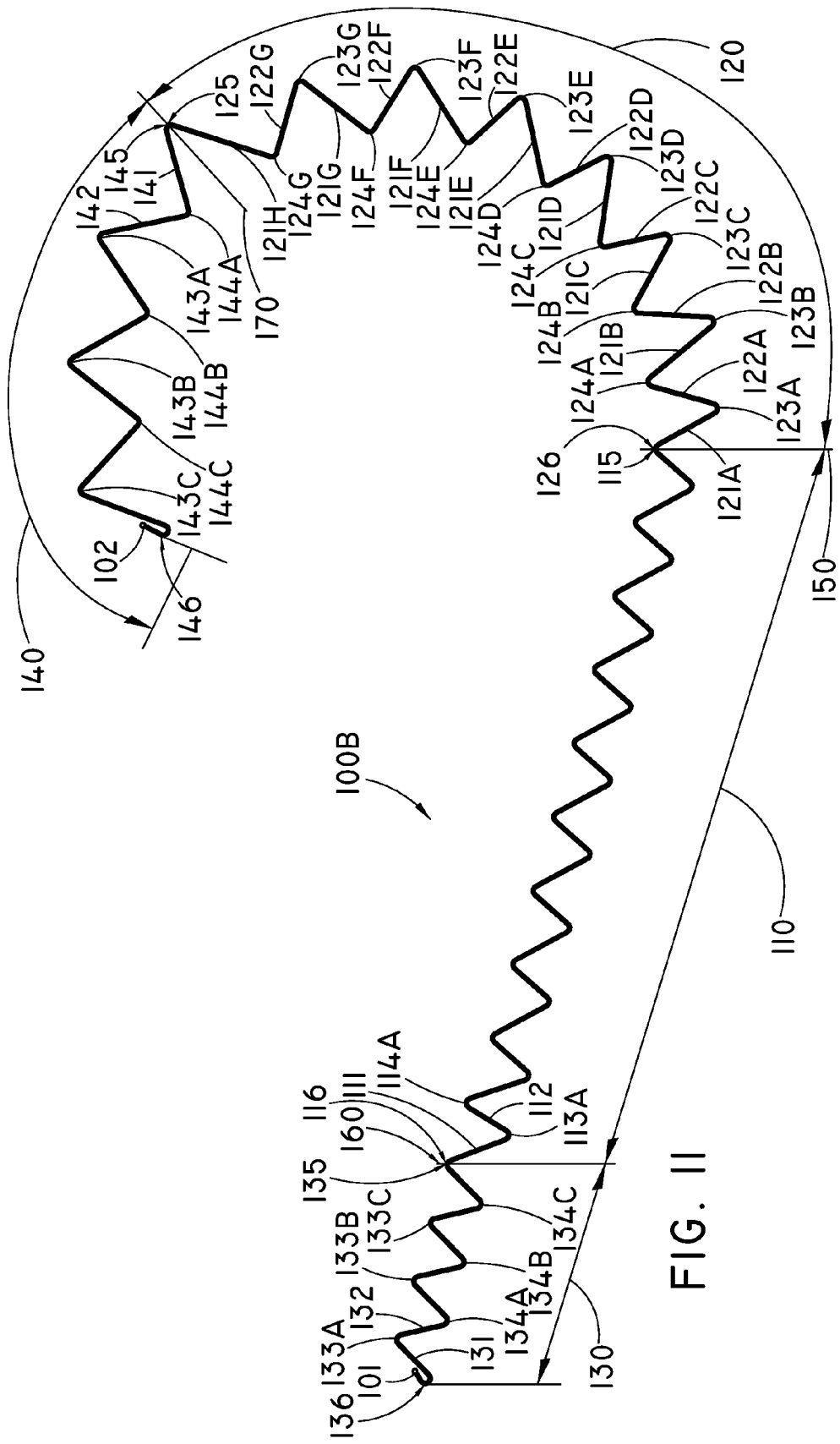
FIG. 11 is a detailed view of the preform of FIG. 1B having increased angles between strut members in a section thereof.
Figure 12:
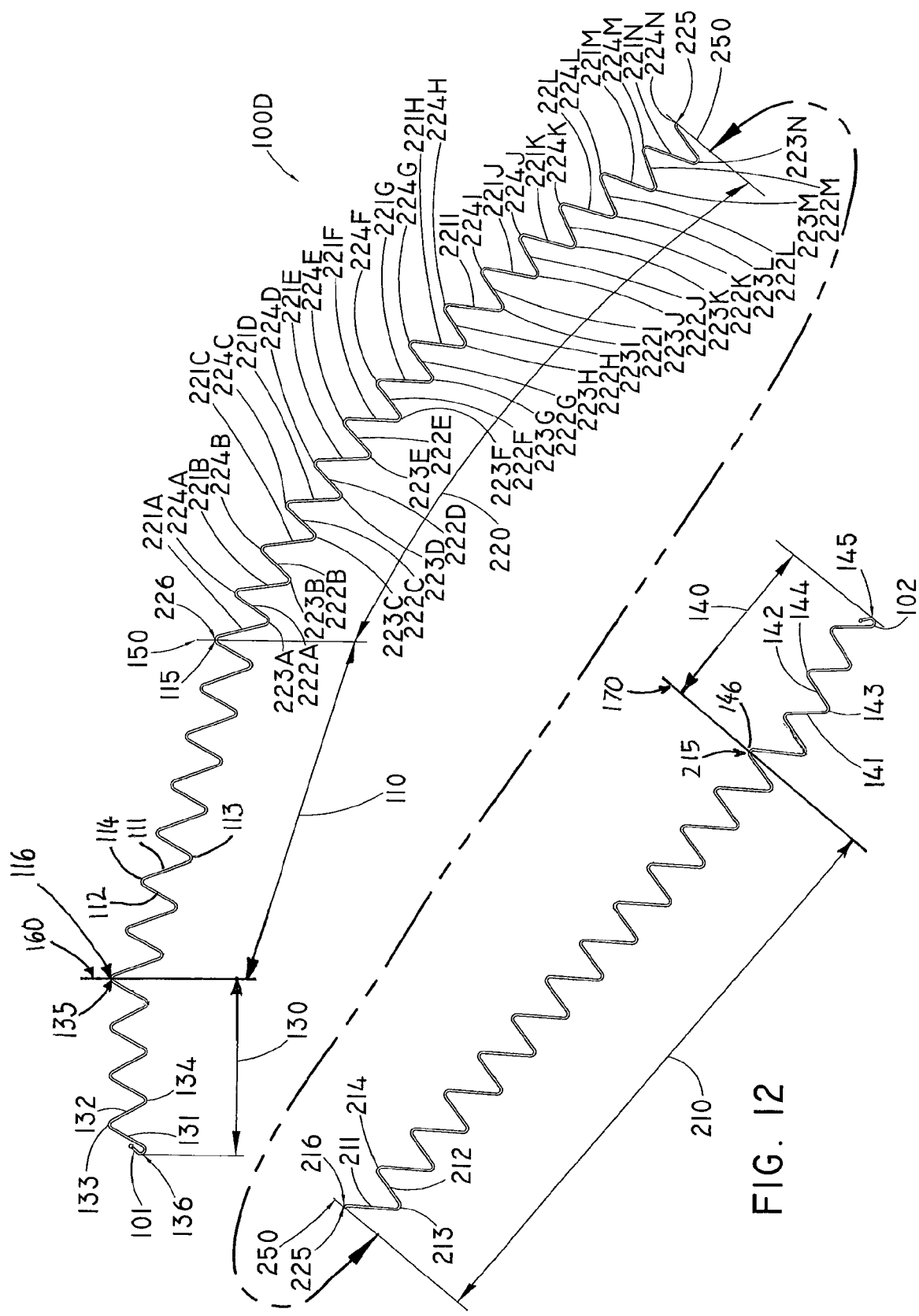
FIG. 12 is a detailed view of the preform of FIGS. 1D and E.
Figure 13:
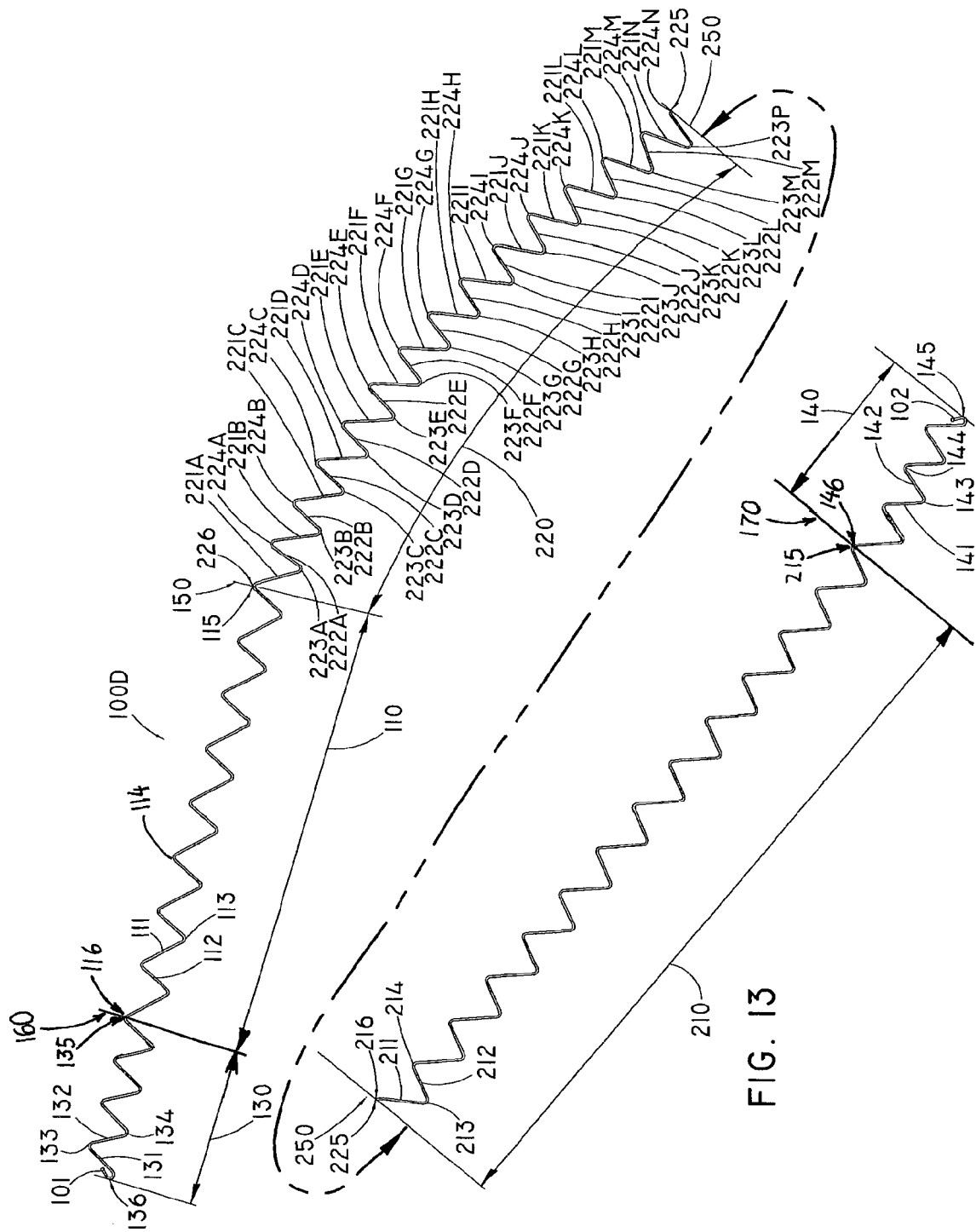
FIG. 13 is a detailed view of the preform of FIGS. 1D and E having the increased angles between strut members in a section thereof.

FIGS. 11 and 13 illustrate an embodiment of the preform 100B and the preform 100D, respectively, having increased angles $A_p$, $A_v$ at the peak and valley bends 113, 114 of the uniform sections 110 (compare the original angles at peak and valley bends 113, 114 of the uniform sections 110 shown in FIGS. 10 and 12, respectively). These increased angles in the uniform sections 110 are created by widening the angle of each peak and valley bend 113, 114 by a predetermined, fixed amount. The predetermined amount may be substantially the same for the angle $A_p$, $A_v$ at each of the peak and valley bends 113, 114, respectively. The angles $A_p$, $A_v$ may be widened by less than or equal to about 80% of the original angle, and may be widened by about 20% to about 60%. In some embodiments, the angles may be widened by about 40%. Note that the less the angles $A_p$, $A_v$ are widened, the less strain is introduced into the elongate member 100 when it is helically wrapped and compressed when attached to the graft member. Accordingly, the less the angles $A_p$, $A_v$ are widened, the greater the fatigue strength of the elongate member 100. It should be understood that while the curved sections 120, 220 and the end sections 130, 140 are not depicted as having increased/widened angles $A_p$, $A_v$ at the peak bends 123, 223, 133, 143 and valley bends 124, 224, 134, 144 they are not so limited, and the angles $A_p$, $A_v$ of the peak and valley bends of any or all of these sections may be widened according to the same or different ranges described above.

Note that in embodiments in which the angles $A_p$, $A_v$ at peak and valley bends 113, 213, 114, 214 of the uniform sections 110, 210 are widened but the angles $A_p$, $A_v$ at peak and valley bends 123, 124 of the curved section 120 or peak and valley bends 123, 124 of the inverse-curved section 220 are left unchanged, the angle $A_p$ between the first struts 122A, 222A and second struts 121A, 221A at the peak bends 123A, 223A (or in some embodiments the angle $A_v$ at the valley bends 124, 224) disposed closest to the transition point 150 is less than the angles $A_p$, $A_v$ at the peak or valley bends 113, 114 of the uniform section 110. This ensures substantial alignment of the peak bends 113, 123, 223 of the uniform section 110 and the curved section 120, or the inverse-curved section 220, through the transition between the curved portion 104 and the straight portion 103 of the graft. Note that in embodiments having widened angles $A_p$, $A_v$, the peak bends may or may not be laterally aligned on the two-dimensional graft layout or when wrapped in a three-dimensional shape, and instead the peak bends are aligned by compressing the angles $A_p$, $A_v$ when the preform is attached to the graft.

Tables 1-3 below illustrate the specific angles at peak and valley bends and strut lengths for each of the first and second struts for several of exemplary embodiments:

TABLE 1

Example of the preform 100A of FIG. 1A with standard and widened angles in section 110 Straight (D = 13 mm)

| | | | Angle (degrees) | |
|---|---|---|---|---|
| Strut No. | Strut Length | Angle No. | FIG. 1A | FIG. 1A with angles widened |
| 131 | 0.294 | | | |
| 132 | 0.294 | 133 | 58.4 | 58.4 |

TABLE 1-continued

Example of the preform 100A of FIG. 1A with standard and widened angles in section 110 Straight (D = 13 mm)

| | | | Angle (degrees) | |
|---|---|---|---|---|
| Strut No. | Strut Length | Angle No. | FIG. 1A | FIG. 1A with angles widened |
| 111 | 0.371 | 134 | 58.4 | 58.4 |
| 112 | 0.289 | 113 | 49.9 | 70.9 |
| 141 | 0.294 | 114 | 49.9 | 70.9 |
| 142 | 0.294 | 143 | 58.4 | 58.4 |
| | | 144 | 58.4 | 58.4 |

TABLE 2

Example of the preform 100B of FIG. 10 with standard angles and FIG. 11 with widened angles in section 110 Straight (D = 13 mm) and Tapered Graft (Dmax = 24 mm, Dmax = 13 mm)

| | | | Angle | Angle |
|---|---|---|---|---|
| Strut No. | Strut Length | Angle No. | FIG. 10 | FIG. 11 |
| 131 | 0.294 | | | |
| 132 | 0.294 | 133 | 58.4 | 58.4 |
| 111 | 0.371 | 134 | 58.4 | 58.4 |
| 11 | 0.294 | 113 | 49.9 | 69.7 |
| 121A | 0.368 | 114 | 49.9 | 69.7 |
| 122A | 0.294 | 123A | 25.1 | 44.8 |
| 121B | 0.368 | 124A | 55.3 | 55.3 |
| 122B | 0.294 | 123B | 42.6 | 42.6 |
| 121C | 0.364 | 124B | 64.3 | 64.3 |
| 122C | 0.299 | 123C | 49.3 | 49.3 |
| 121D | 0.381 | 124C | 69.7 | 69.7 |
| 122D | 0.321 | 123D | 54.5 | 54.5 |
| 121E | 0.390 | 124D | 74.7 | 74.7 |
| 122E | 0.333 | 123E | 59.3 | 59.3 |
| 121F | 0.390 | 124E | 79.5 | 79.5 |
| 122F | 0.333 | 123F | 63.9 | 63.9 |
| 121G | 0.400 | 124F | 83.9 | 83.9 |
| 122G | 0.345 | 123G | 68.1 | 68.1 |
| 121H | 0.409 | 124G | 88.1 | 88.1 |
| 122H | 0.357 | 123G | 72.1 | 72.1 |
| 121I | 0.492 | 124G | 85.5 | 85.5 |
| 141 | 0.430 | 123I | 59.7 | 59.7 |
| 142 | 0.430 | 144 | 85.8 | 85.8 |
| 141 | 0.430 | 145 | 67.9 | 67.9 |
| 142 | 0.430 | 144 | 85.8 | 85.8 |
| 141 | 0.430 | 145 | 67.9 | 67.9 |
| 142 | 0.430 | 144 | 85.8 | 85.8 |

TABLE 3

Example of the preform 100D of FIG. 12 with standard angles and FIG. 13 with widened angles in section 110 Preform Length As Attached to Graft = 122 mm; Sections 130 and 110 (D = 9 mm), Sections 210 and 140 (D = 13 mm), Section 220 (D = transitions from 9 mm to 13 mm)

| | | | Angle in Degrees | |
|---|---|---|---|---|
| Strut No. | Strut Length | Angle No. | FIG. 12 (As Attached) | FIG. 13 (Widened) |
| 131 | 0.294 | | | |
| 132 | 0.294 | 133 | 58.4 | 58.4 |
| 111 | 0.371 | 113 | 49.9 | 69.7 |
| 112 | 0.294 | 114 | 49.9 | 69.7 |
| 221A | 0.369 | 223A | 64.3 | 64.3 |
| 222A | 0.288 | 224A | 68.6 | 68.6 |
| 221B | 0.361 | 223B | 71.8 | 71.8 |
| 222B | 0.285 | 224B | 47.6 | 47.6 |

TABLE 3-continued

Example of the preform 100D of FIG. 12 with standard
angles and FIG. 13 with widened angles in section 110
Preform Length As Attached to Graft = 122 mm; Sections
130 and 110 (D = 9 mm), Sections 210 and 140 (D = 13 mm),
Section 220 (D = transitions from 9 mm to 13 mm)

| Strut No. | Strut Length | Angle No. | Angle in Degrees FIG. 12 (As Attached) | FIG. 13 (Widened) |
|---|---|---|---|---|
| 221C | 0.359 | 223C | 50.8 | 50.8 |
| 222C | 0.283 | 224C | 46.3 | 46.3 |
| 221D | 0.358 | 223D | 49.5 | 49.5 |
| 222D | 0.281 | 224D | 45.0 | 45.0 |
| 221E | 0.356 | 223E | 48.2 | 48.2 |
| 222E | 0.279 | 224E | 43.7 | 43.7 |
| 221F | 0.355 | 223F | 46.9 | 46.9 |
| 222F | 0.277 | 224F | 42.4 | 42.4 |
| 221G | 0.353 | 223G | 45.5 | 45.5 |
| 222G | 0.275 | 224G | 41.1 | 41.1 |
| 221H | 0.352 | 223H | 44.2 | 44.2 |
| 222H | 0.273 | 224H | 39.7 | 39.7 |
| 221I | 0.350 | 223I | 42.8 | 42.8 |
| 222I | 0.271 | 224I | 38.4 | 38.4 |
| 221J | 0.349 | 223J | 41.5 | 41.5 |
| 222J | 0.269 | 224J | 37.0 | 37.0 |
| 221K | 0.347 | 223K | 41.0 | 41.0 |
| 222K | 0.267 | 224K | 35.6 | 35.6 |
| 221L | 0.346 | 223L | 38.7 | 38.7 |
| 222L | 0.265 | 224L | 34.2 | 34.2 |
| 221M | 0.345 | 223M | 37.2 | 37.2 |
| 222M | 0.264 | 224M | 32.7 | 32.7 |
| 221N | 0.343 | 223N | 35.8 | 35.8 |
| 222N | 0.262 | 224N | 31.3 | 31.3 |
| 221O | 0.342 | 223O | 34.3 | 34.3 |
| 222O | 0.260 | 224O | 29.8 | 29.8 |
| 221P | 0.345 | 223P | 32.8 | 32.8 |
| 211 | 0.346 | 224P | 32.9 | 32.9 |
| 212 | 0.260 | 223Q | 39.8 | 39.8 |
| 141 | 0.260 | 213 | 42.6 | 42.6 |
| 142 | 0.260 | 214 | 42.6 | 42.6 |
|  |  | 143, 144 | 36.7 | 36.7 |

Figure 21A:
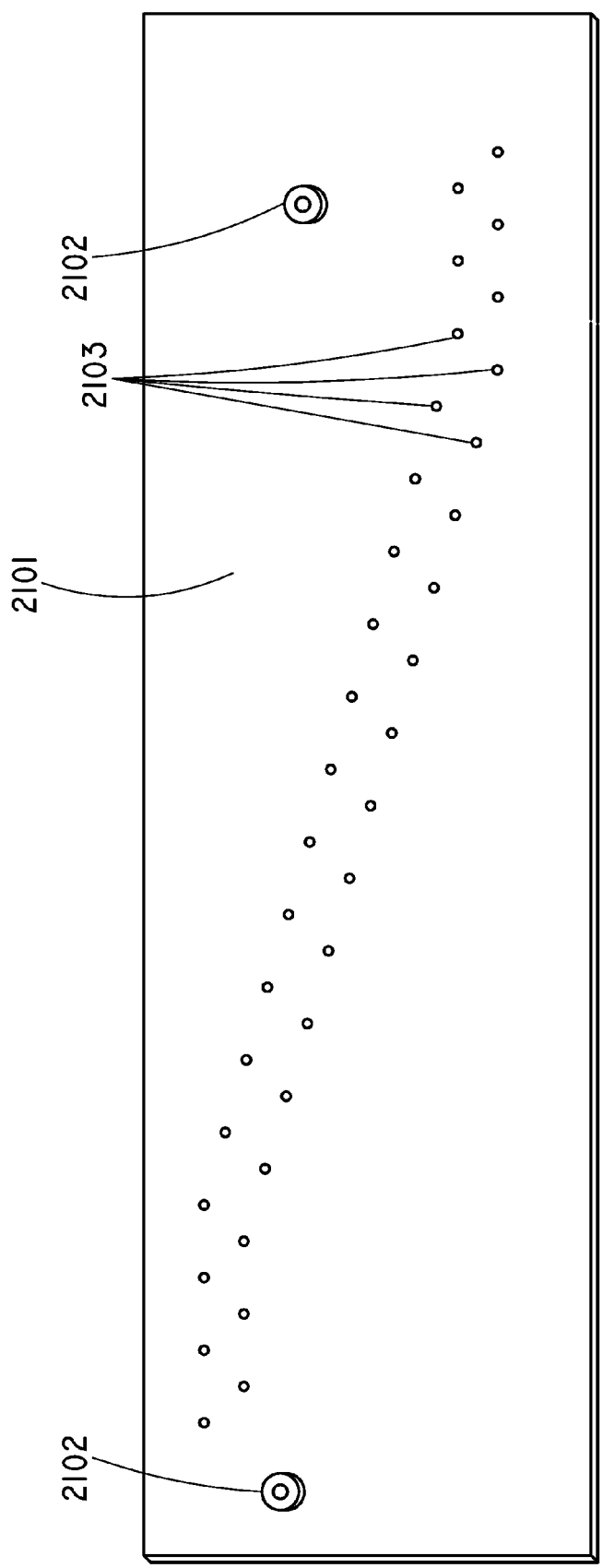
FIGS. 21A-E illustrate a step by step method of forming a preform.

A method of manufacturing the preforms 100a-d described above is shown in FIGS. 21a-e. Initially, a plurality of holes 2103 corresponding to the center of the radius of each peak and valley bend are drilled into a metallic plate 2101 according to the predetermined pattern of bends for a particular preform (FIG. 21a). The metallic plate 2101 has at least one, and preferably two fixing members 2102 for securely fixing the ends 101, 102 of the elongate member 100 under tension. The elongate member may be a wire made from an elastic or super elastic material, for example and without limitation, Nitinol. The metallic plate 2101 may be rotatably attached to a fixture such that it can be rotated to form the elongate member 100 in a desired shape.

Figure 21B:
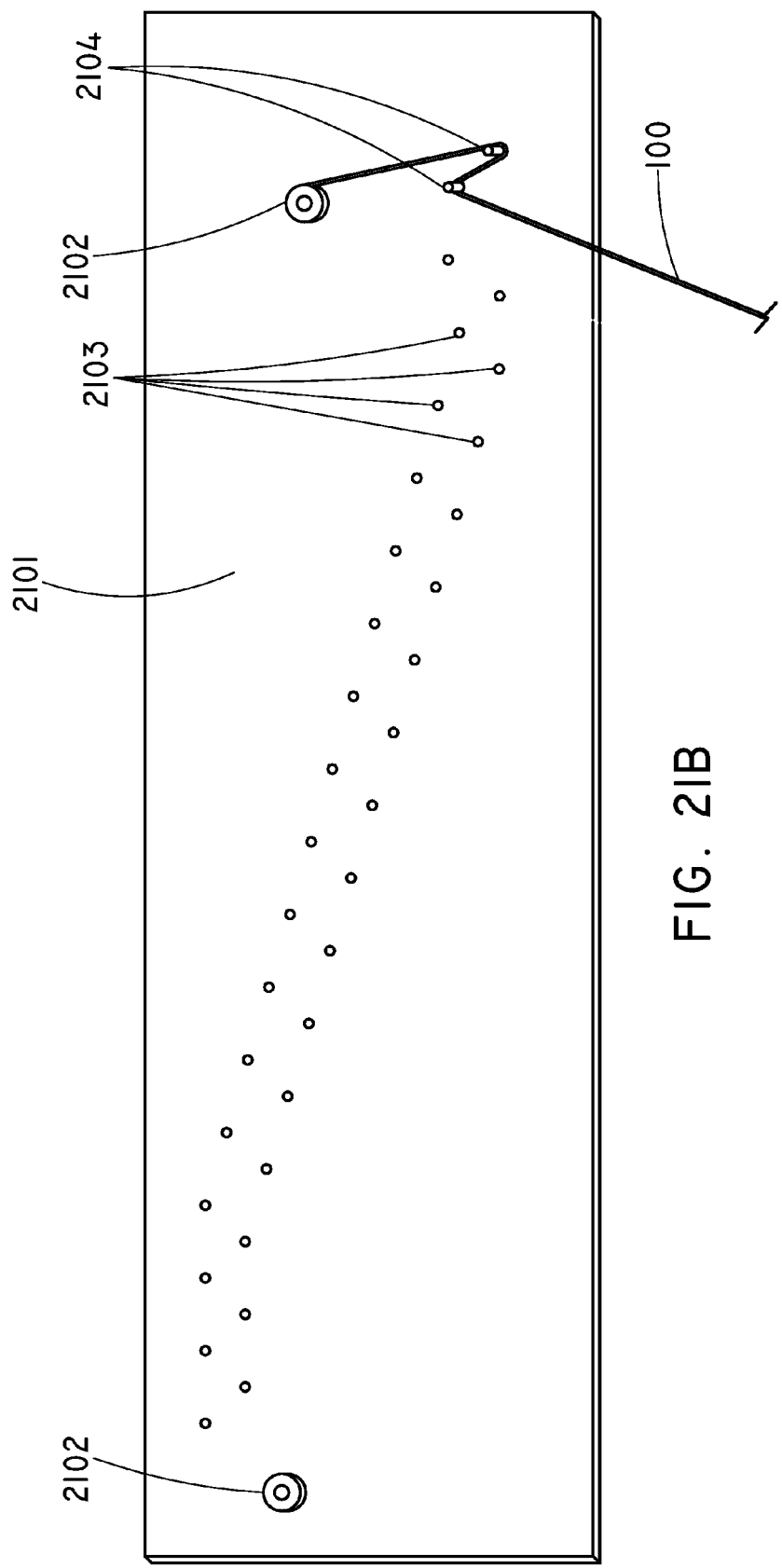
Figure 21C:
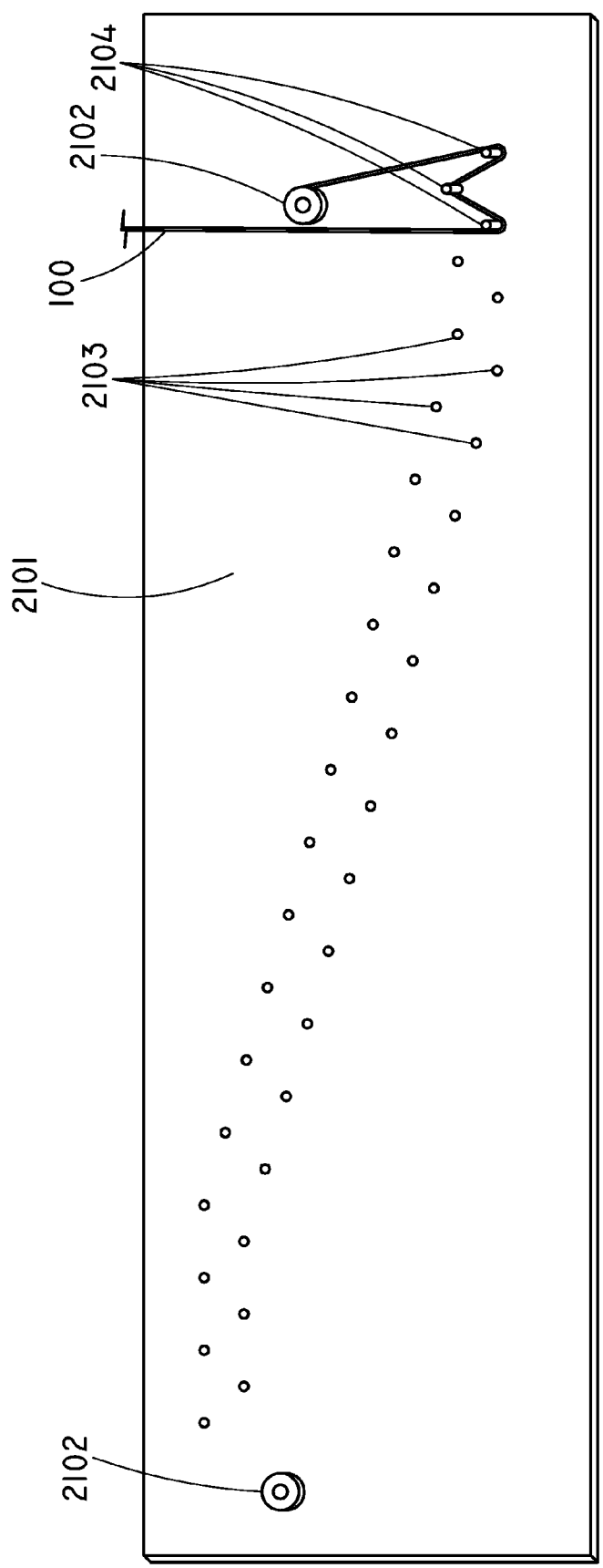
Figure 21D:
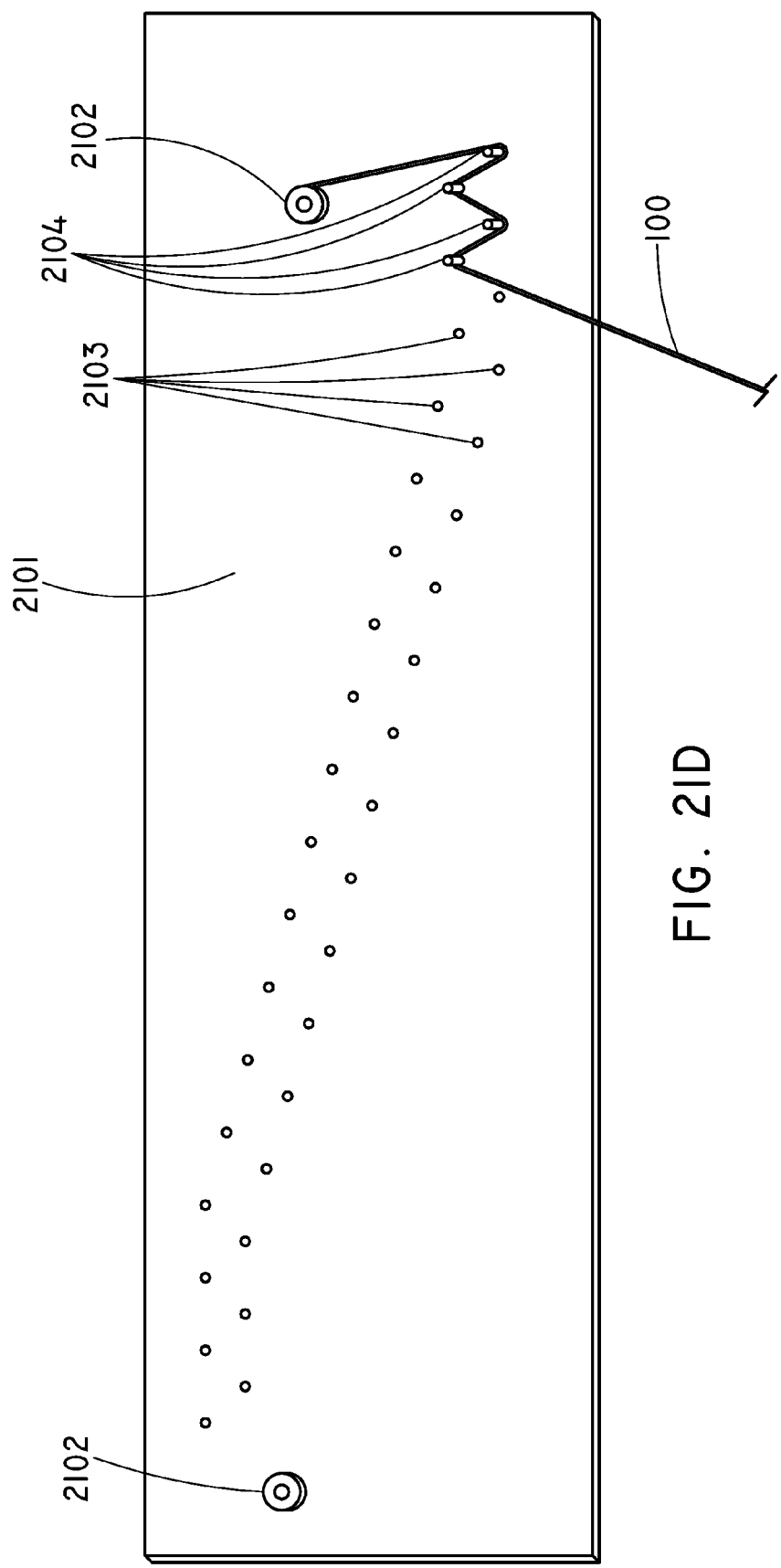
Figure 21E:
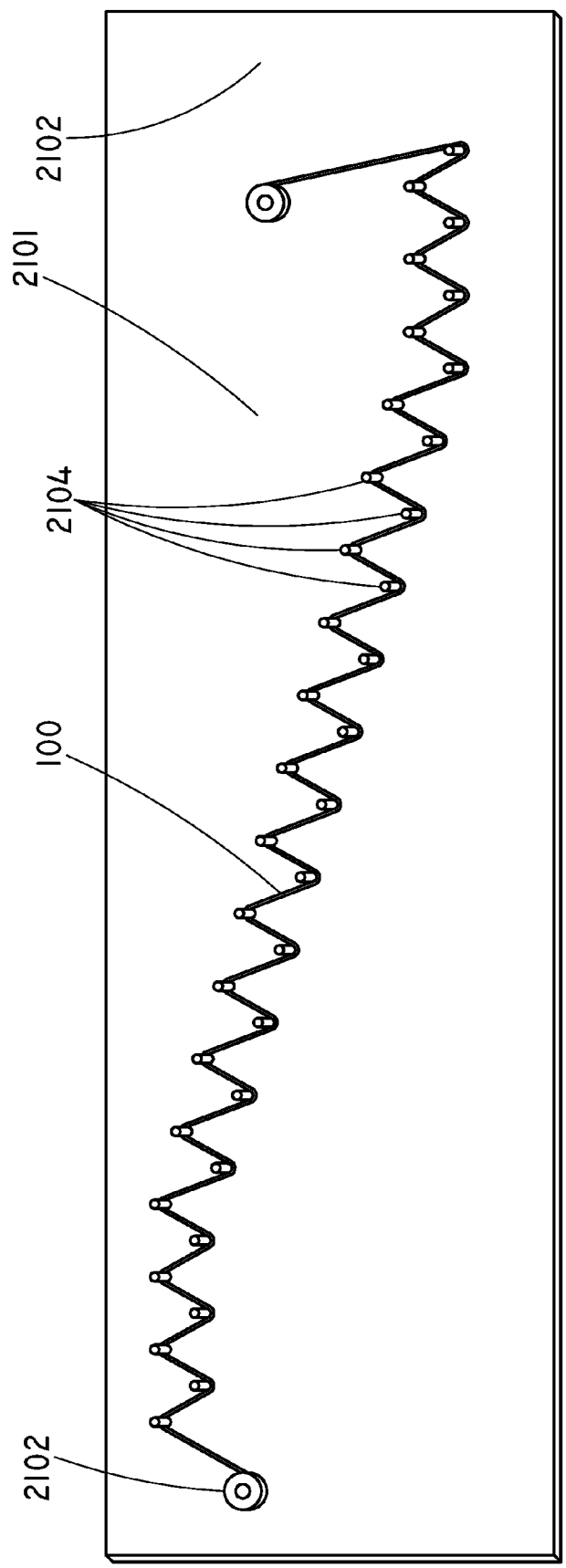

As shown in FIGS. 21B-D, one of the first or second ends 101, 102 are secured to one of the fixing members 2102, and the other end is attached to a tensioning mechanism, such as a weight. The tensioning mechanism may tension the elongate member 100 to about 8 Lbf for a 0.014 inch (0.36 millimeters) diameter Nitinol wire, or generally about 75% of the force at which plastic deformation occurs for the desired material. Next, pins 2104 are inserted into each hole 2103 one by one, and the elongate member is wrapped around each pin to produce a bend (FIGS. 21B-D). Note that the radius of curvature for each bend is essentially determined by a diameter of the pin, and as such, can be varied to produce more "U-shaped" or "V-shaped" bends by increasing or decreasing the size of the holes 2103 and the corresponding pins 2104.

Once all the pins 2104 have been inserted and the elongate member 100 has been wrapped around the pins 2104 to achieve its desired shape, a portion of the elongate member 100 disposed between the last pin 1204 and the tensioning mechanism is secured to the metallic plate 2101 by the second fixing member 2102. The elongate member is then severed at a location between the second fixing member and the tensioning mechanism, and the metallic plate 2101 and the elongate member 100 are heated to a temperature sufficient to heat-set the elongate member in its desired shape. It should be understood that the preform is not limited to the above described method of manufacture, and the shape of the preform or elongate support member may be achieved without heat-setting by, for example and without limitation, using cold working or the like of the elongate member 100, as is known in the art.

In one alternative method, the metallic plate may include cylindrical or conically shaped mandrels positioned at the portion of the plate corresponding to the end sections 130, 140 of the elongate member to produce a preform having curved end sections 130, 140, as shown in FIGS. 15A-D. Like the metallic plate 2101, holes 2103 are drilled into the mandrels and desired shape is formed as described above by successively inserting pins 1204, wrapping the elongate member 100 therearound, and then heat-setting the elongate member in its desired shape. It should be understood that other methods of forming such a shape are contemplated, for example and without limitation, cold forming or cold working of the elongate member 100.

Figure 16A:
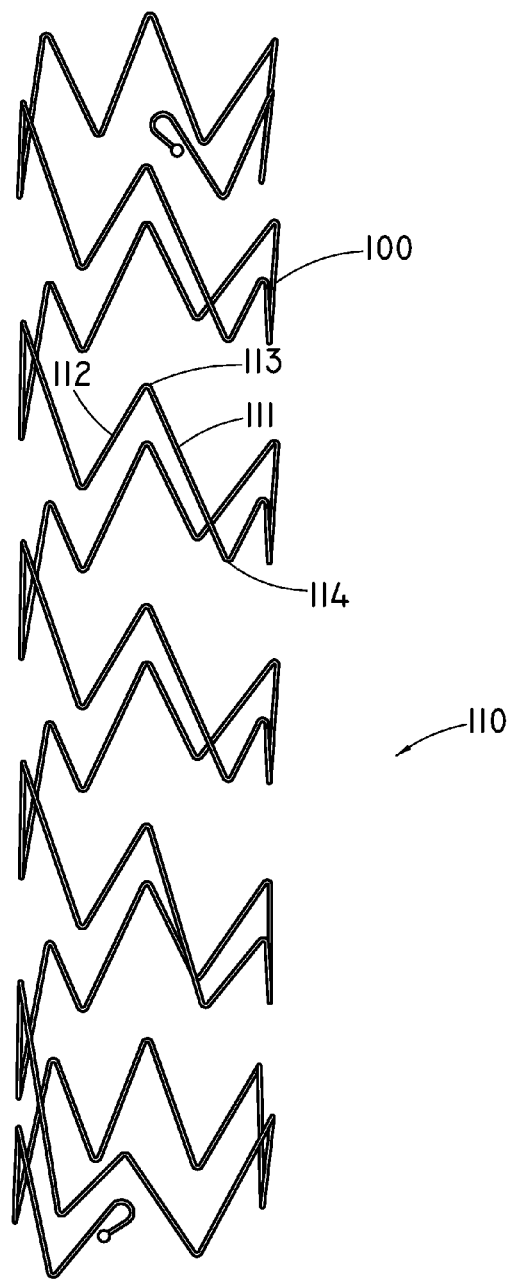
FIG. 16A is a side elevation view of the preform of FIG. 1A formed in a helical shape.
Figure 16B:
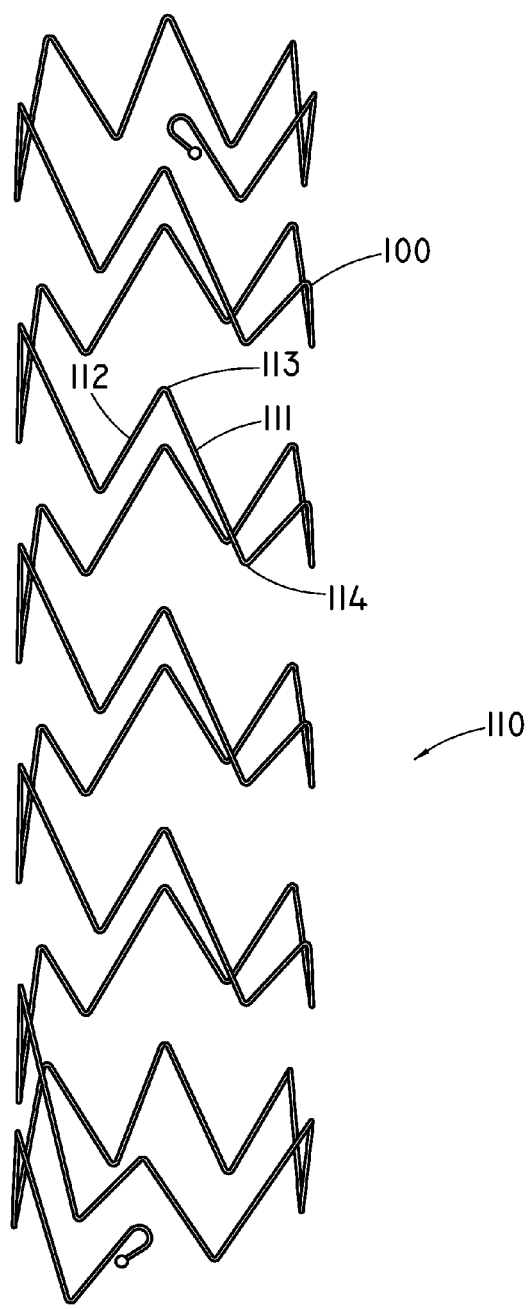
FIG. 16B is a side elevation view of the helically shaped preform of FIG. 16A having increased angles between strut members in a section thereof.

FIG. 16A illustrates the elongate member 100 of FIG. 1A preformed in a three-dimensional, helical shape having a substantially cylindrical diameter with a constant radius. As shown in FIG. 16B, in one embodiment, the cylindrical diameter of the portion of the elongate member corresponding to the uniform section 110 may be larger than that of the end sections 130, 140 to accommodate widened or enlarged angles $A_p$, $A_v$ at some or all of the peak bends 113 and valley bends 114. Alternatively, the length of the uniform section 110 may be increased to accommodate the widened angles $A_p$, $A_v$.

Figure 17A:
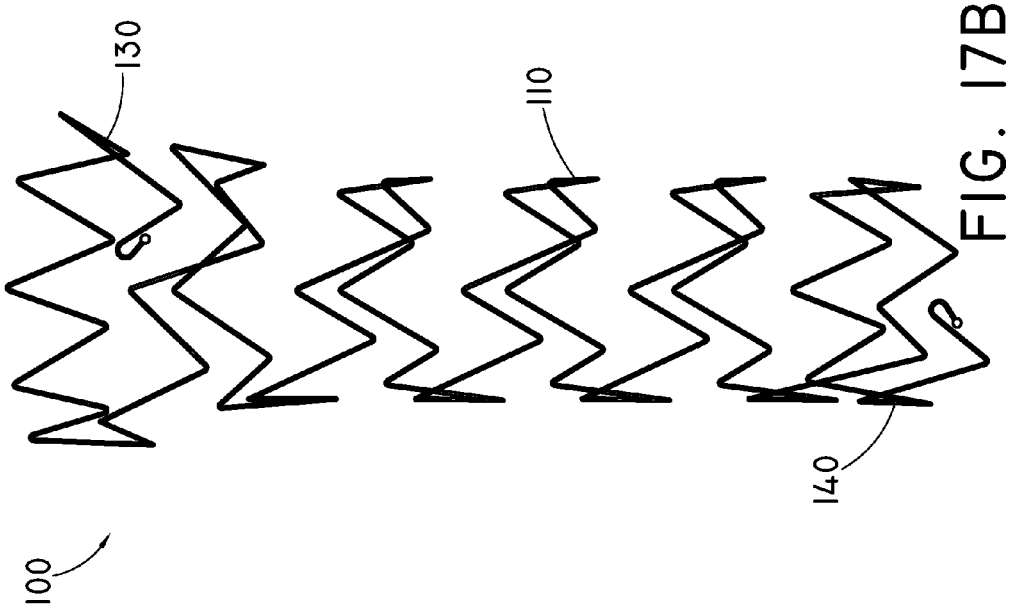
FIG. 17A is an orthogonal view of the elongate member of FIG. 1B formed in a helical shape.
Figure 17B:
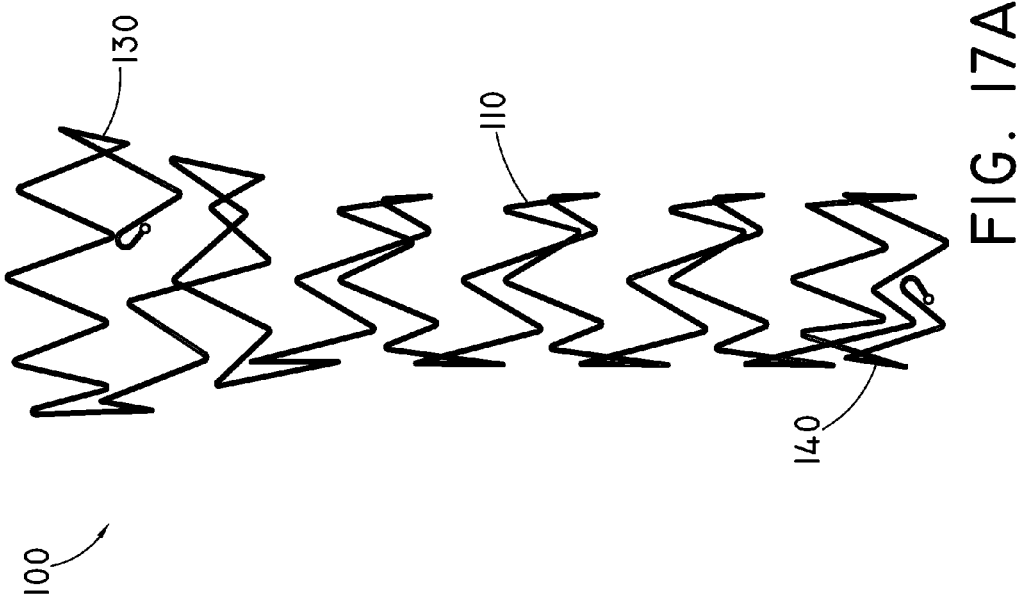
FIG. 17B is an orthogonal view of the helically shaped elongate member of FIG. 17A having increased angles between strut members in a section thereof.

FIG. 17A illustrates the elongate member 100 of FIG. 1B preformed in a three-dimensional, helical form. The helical form may include a first portion having a substantially cylindrical shape and a constant radius, which corresponds to the uniform section 110 and the end section 130. The helical form may also have a conic helical shape corresponding to the curved section 120. As shown in FIGS. 17A and 17B, the conic helical shape may progressively extend radially outward from the diameter of the first substantially cylindrical portion to a diameter of a second substantially cylindrical portion corresponding to the end section 140. The radius of the second cylindrical portion may be larger than the radius of the first cylindrical portion.

As shown in FIG. 17B, in one embodiment, the cylindrical diameter of the first substantially cylindrical portion of the elongate member corresponding to the uniform section 110 may have a diameter that is larger than that of the end section 130 to accommodate widened or enlarged angles $A_p$, $A_v$ at some or all of the peak bends 113 and valley bends 114. Alternatively, the length of the uniform section 110 may be increased to accommodate the widened angles.

Figure 18A:
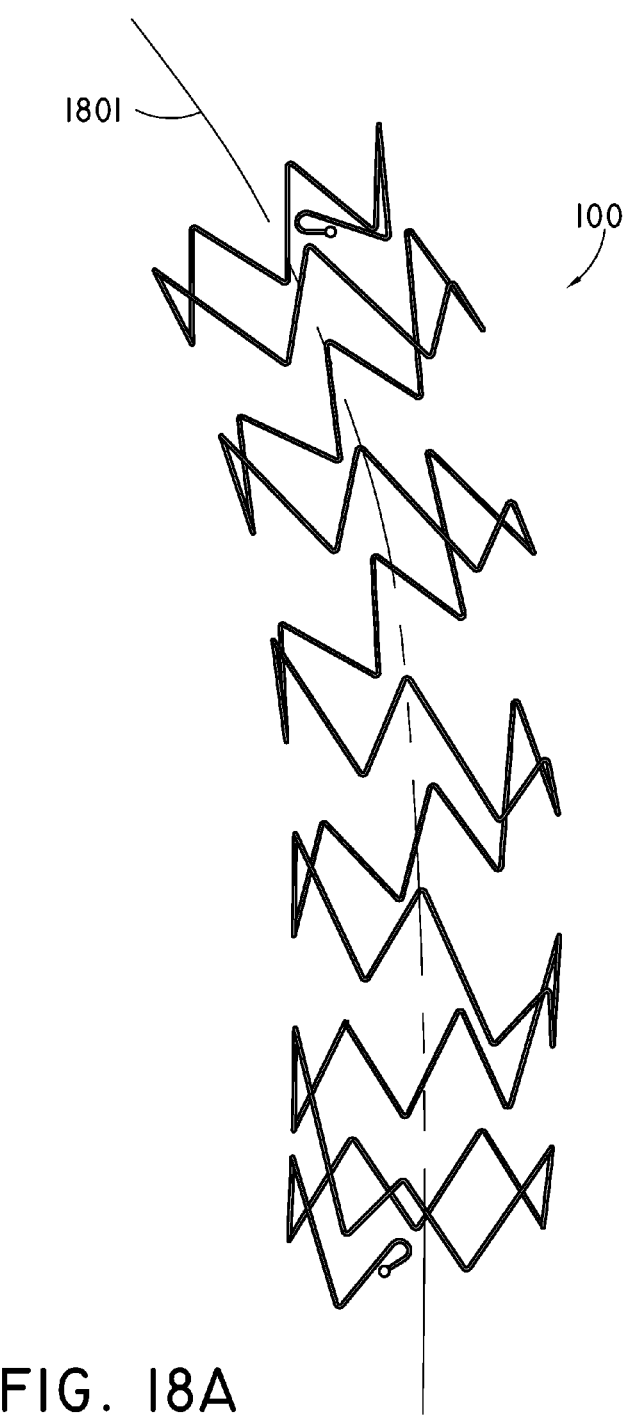
FIG. 18A is an orthogonal view of the elongate member of FIG. 16A formed in a helical, curved shape.

FIG. 18A illustrates the elongate member 100 of the preform 100A in FIG. 1A formed in a three-dimensional, helical shape formed about a central axis 1801. The central axis 1801 may have a preformed, curved shape as shown in FIGS. 18A and B, resulting in a curvedly extending helical preform. The central axis 1801 may extend along the entire length of the preform, or may be isolated to a portion thereof.

Figure 18B:
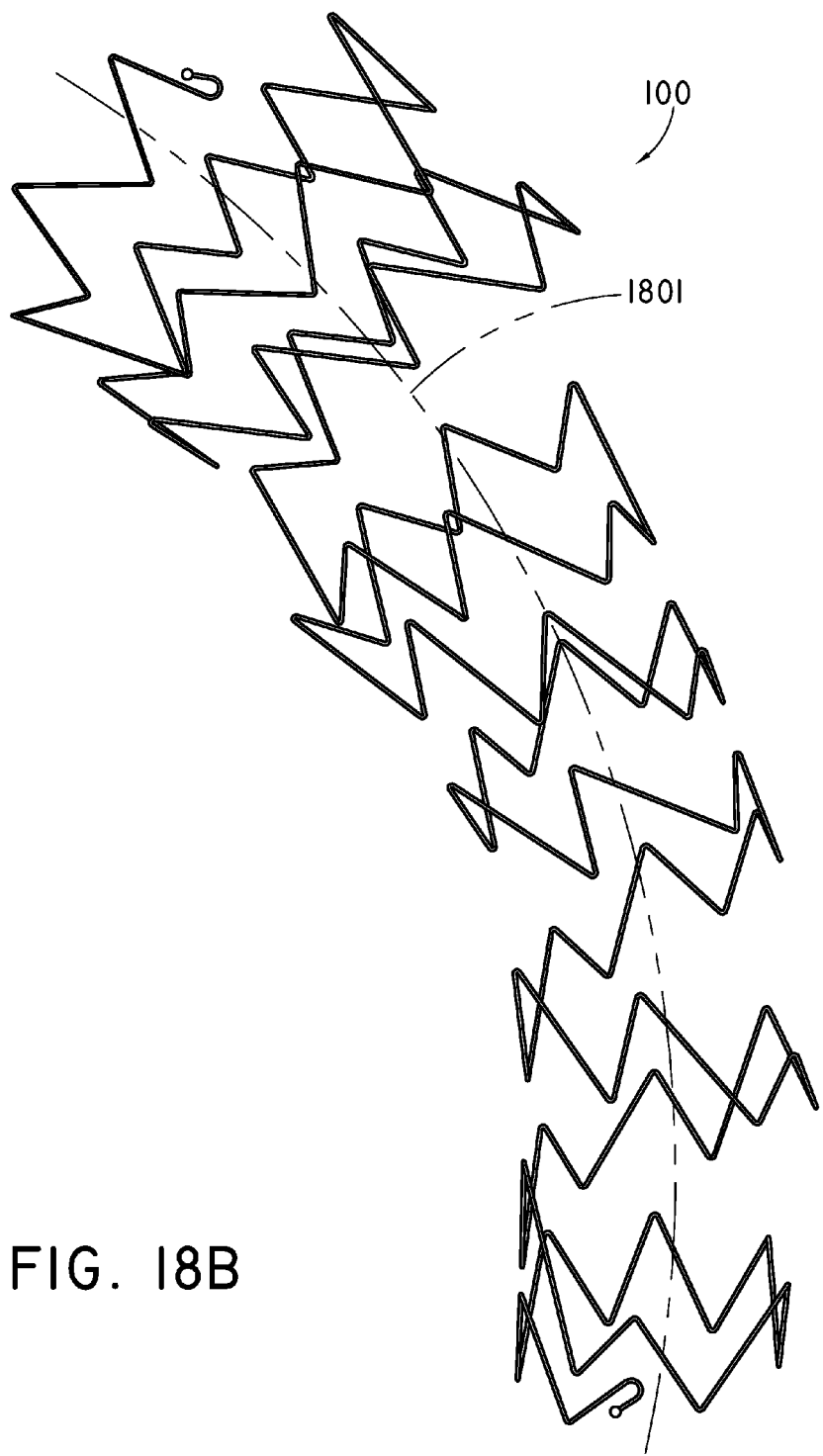
FIG. 18B is an orthogonal view of the helically shaped elongate member of FIG. 17A having a curved shape.

FIG. 18B illustrates the elongate member 100 of the preform in FIG. 17 having a helical shape winding about a predetermined curved central axis 1801. The predetermined curved shape may extend along the entirety of the central axis, or may be isolated to a portion thereof.

Figure 19A:
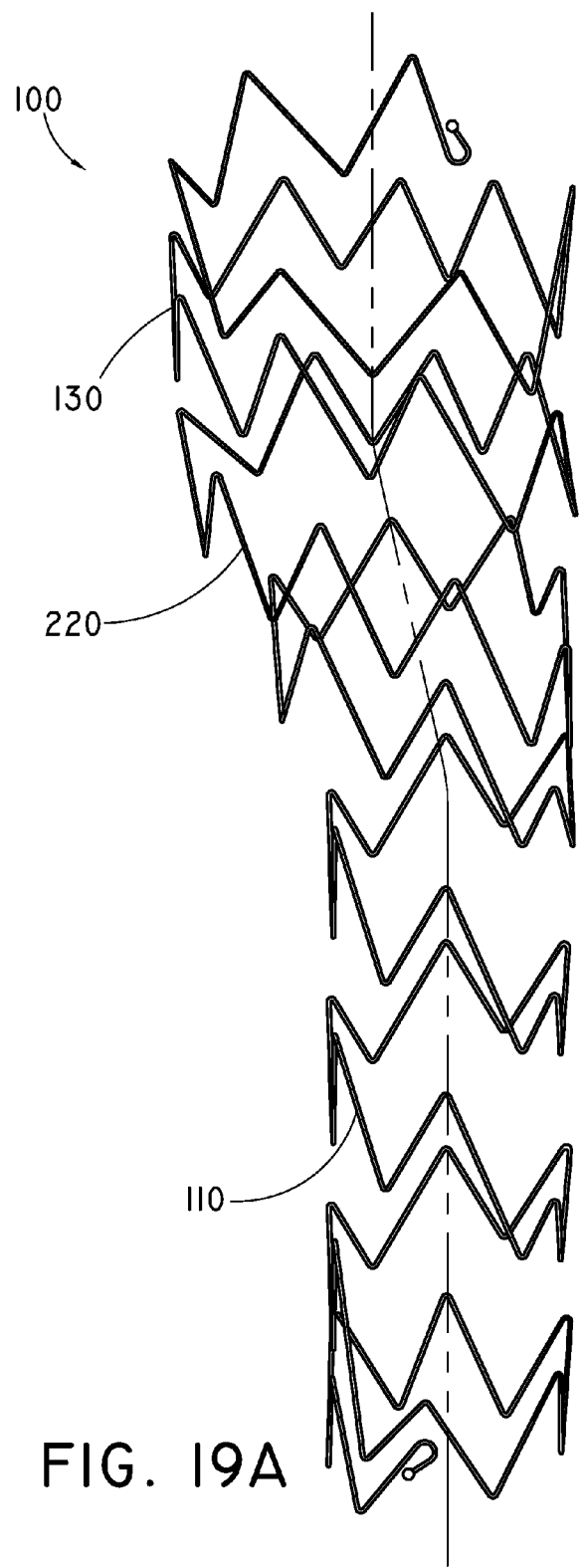
FIG. 19A is an orthogonal view of the elongate member of FIGS. 1D and E formed in a helical shape.

FIG. 19A illustrates the elongate member 100 of FIGS. 1D and 1E formed in a three-dimensional, helical shape disposed about a central axis 1901. The three-dimensional shape may have a first substantially cylindrical shape with a constant radius corresponding to the uniform section 110 and the end section 130, and a conic helical shape corresponding to the inverse-curved section 220. The conic helical shape may progressively extend radially inward from the diameter of the first substantially cylindrical portion to a diameter of a second substantially cylindrical portion corresponding to the second uniform section 210 and the end section 140. A radius of the first cylindrical portion may be larger than the radius of the second cylindrical portion. Alternatively, the length of the uniform sections 110, 210 may be increased to accommodate the widened angles.

Figure 19B:
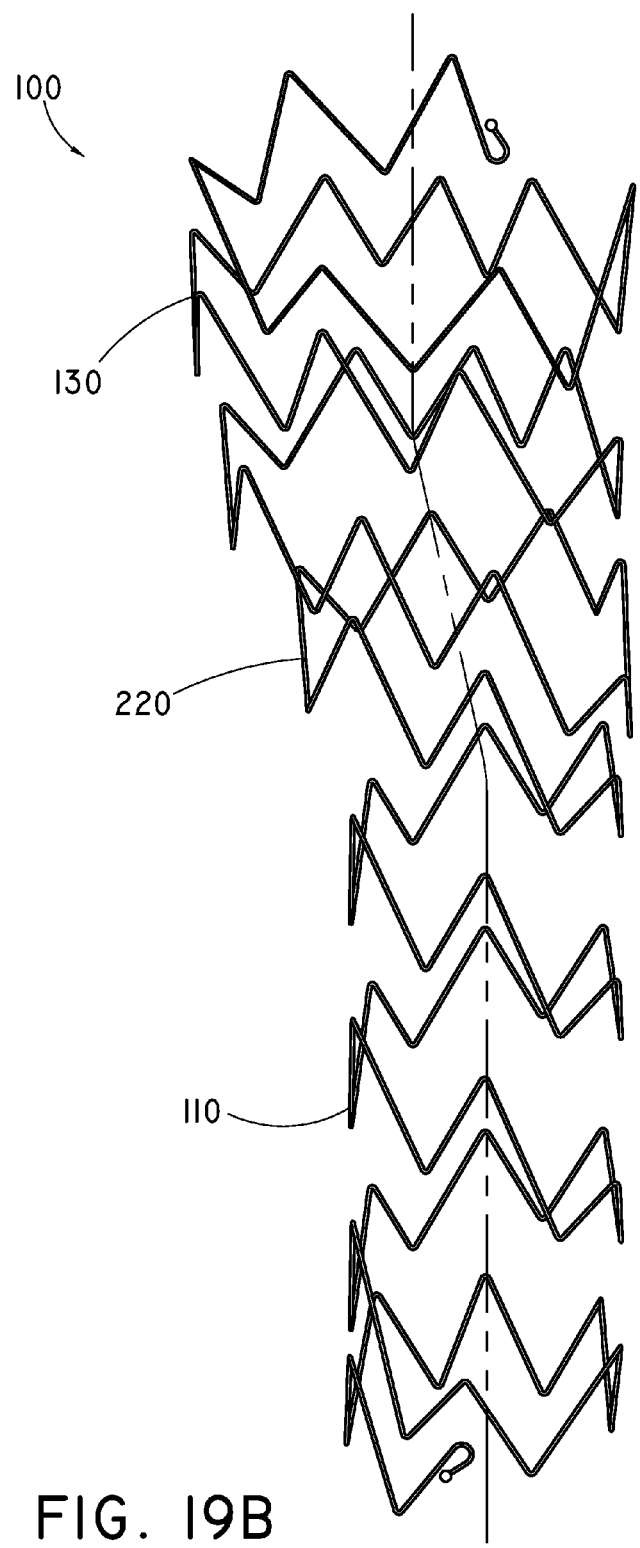
FIG. 19B is an orthogonal view of the helically shaped elongate member of FIG. 19A having increased angles between strut members in a section thereof.

As shown in FIG. 19B, in one embodiment, the cylindrical diameter of the first and second substantially cylindrical portions of the elongate member corresponding to the first uniform section 110 and the second uniform section 210, respectively, may have diameters that are larger than that of the end section 130 and the end section 140, respectively, to accommodate widened, or enlarged angles $A_p$, $A_v$ at some or all of the peak bends 113, 213 and valley bends 114, 214.

Pre-forming the elongate members 100 in a three-dimensional, cylindrical and/or conical shape that approximates the three-dimensional shape of the graft to which the elongate members 100 are to be affixed may result in reduced strain in the elongate members 100 when the preforms are attached to the graft. This reduced strain may increase the fatigue strength of the elongate members 100 as compared to the substantially planar preforms 100A-100D shown in FIGS. 1A-1E.

Any of the above described preformed elongate members 100 formed in a three-dimensional, substantially helical shape may be formed by wrapping the elongate member 100 around a mandrel having holes corresponding to the desired placement of the peak and valley bends using the pin insertion and tensioned wrapping, and heat-setting method described above in connection with FIGS. 21A-E. Other methods of three-dimensional forming are also contemplated, for example and without limitation, cold working or the like of the elongate member 100.

Figure 22:
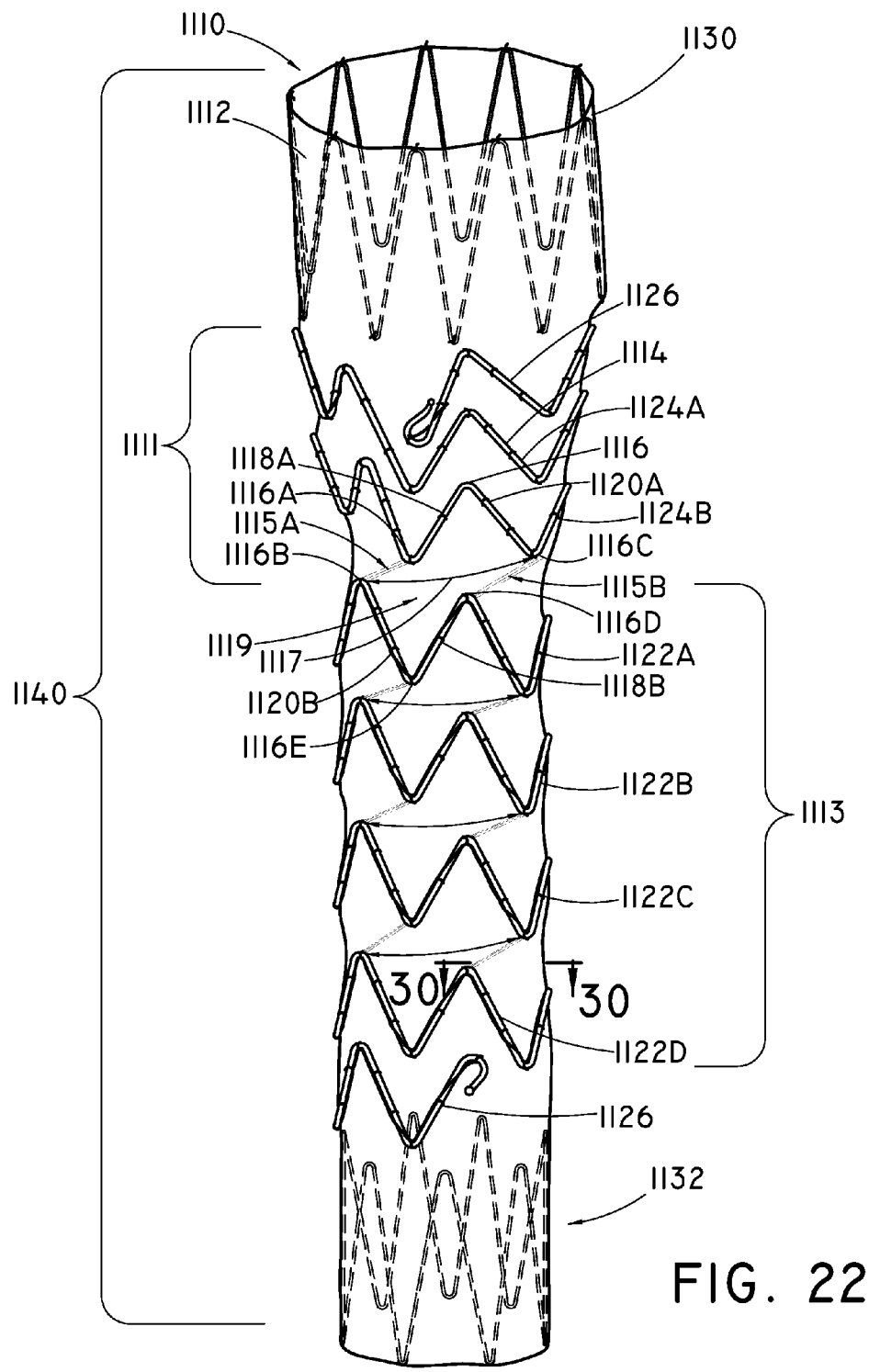
FIG. 22 illustrates an endoluminal prosthesis having a uniform section and a tapered section in a first condition.

FIG. 22 illustrates an embodiment of an endoluminal prosthesis 1110. The endoluminal prosthesis 1110 includes a graft 1112 and may be placed within a diseased vessel in a configuration 1140 in which the endoluminal prosthesis 1110 is substantially straight. The graft 1112 may have a generally tubular configuration defining a lumen disposed within and extending the length of the graft 1112. The tubular graft material may be constructed from a biocompatible material. The term "biocompatible" refers to a material that is substantially non-toxic in the in vivo environment of its intended use, and that is not substantially rejected by the patient's physiological system (i.e., is non-antigenic). Examples of biocompatible materials from which textile graft material can be formed include, without limitation, polyesters, such as polyethylene terephthalate; fluorinated polymers, such as polytetrafluoroethylene (PTFE) and fibers of expanded PTFE, and polyurethanes. In addition, materials that are not inherently biocompatible may be subjected to surface modifications in order to render the materials biocompatible. Examples of surface modifications include graft polymerization of biocompatible polymers on the materials surface, coating of the surface with a cross linked biocompatible polymer, chemical modification with biocompatible functional groups, and immobilization of a compatibilizing agent such as heparin or other biocompatible substances. Thus, any fibrous material having sufficient strength to survive in the in vivo environment may be used to form a textile graft, provided the final textile is biocompatible. Fibers suitable for making textile grafts include polyethylene, polypropylene, polyaramids, polyacrylonitrile, nylon, and cellulose, in addition to the polyesters, fluorinated polymers, and polyurethanes as listed above. Furthermore, bioremodelable materials may also be used singly or in combination with the aforementioned polymer materials. The textile may be made of one or more polymers that do not require treatment or modification to be biocompatible. The graft may be constructed from woven multifilament polyester, for example and without limitation, Dacron™, produced by DuPont. Dacron™ is known to be sufficiently biologically inert, non-biodegradable, and durable to permit safe insertion inside the human body.

Another example of suitable materials is Polyester, which is known to excite fibrous ingrowth that promotes secure attachment of the graft to the wall of the body lumen in which it is implanted within a few months of its insertion. A flat sheet of textile material may be formed into a tubular configuration by laser bonding.

Returning to FIG. 22, the endoluminal prosthesis 1110 has a tapered section 1111 with a diameter that increases throughout the length of the section. The endoluminal prosthesis 1110 also includes a uniform section 1113 with a generally constant diameter throughout the length of the section. In some embodiments, the uniform section 1113 may have a uniform diameter of about 13 mm and a length of about 56 mm. The tapered section 1111 may have a diameter that ranges from about 13 mm to about 24 mm. The tapered section may form a taper throughout the length of the section 1111 that is shaped to compliment and interface with the size and shape of the body vessel in which it is to be implanted. The tapered section 1111 may be either symmetrical or asymmetrical. The length of the uniform section 1113 may be about 17 mm. In another embodiment, the entire graft may include a generally uniform section with a generally constant diameter throughout its length (FIG. 5). The endoluminal prosthesis 1110 also includes a first end 1130 and a second end 1132. A sealing stent may be placed within the interior surface of the graft 1112 at the first and second ends 1130, 1132. The sealing stents may be attached to the first end 1130 and the second end 1132 of the graft 1112 by any attaching mechanism, for example and without limitation, suturing.

A preform comprising an elongate member 1114 is attached to the outer surface of the graft 1112. The elongate member 1114 may be wrapped around and attached to the graft in a longitudinally and circumferentially extending manner. The elongate member 1114 is wrapped around the graft 1112 such that it forms a plurality of turns 1122A-E, 1124A-B, with each turn extending substantially 360 degrees around the graft in a continuous manner. The plurality of turns 1122A-E, 1124A-B are disposed throughout both the first section of the graft and the second section of the graft. Each turn of the elongate member 1114 has a plurality of bends 1116 (e.g. peak bends, valley bends) forming apices (apexes) that connect a pair of circumferentially adjacent first 1118 and second struts 1120 in the same turn at an angle, as described above in connection with the preforms of FIGS. 1A-1E. Each of the first struts 1118 extends from each bend 1116 in a first direction and each of the second struts 1120 extends away from the same bend 1116 in a second direction, where the second direction is different than the first such that the ends of the first and second struts 1118, 1120 that are not attached together at the particular bend 1116 extend progressively away from each other in the circumferential direction moving in the direction away from the particular bend 1116. The elongate member 1114 may be attached to the graft 1112 by any means, including, for example and without limitation, sutures, adhesives, lamination between layers of polymers or the like.

In embodiments employing sutures, the elongate member 1114 is attached to the graft 1112 with sutures disposed only at the bends 1116. In other embodiments, the elongate member 1114 is attached to the graft 1112 with sutures disposed at the bends 1116 and along the first 1118 and second struts 1120 extending between the bends 116. While the embodiment shown in FIG. 22 is illustrated having turns 1122A-E, 1124A, 1124B, comprised of undulating struts and bends, it should be understood that preform including the elongate member 1114 is not limited thereto. For example, as shown in the embodiment of FIG. 35A, the preform 3500 may have an elongate member 3520 that is formed from a wire having a plurality of attachment members 3510 and a substantially straight shape therebetween. The attachment members 3510 may be formed in other shapes as shown in FIG. 35C, for example, a loop or eyelet 3510A or a "U" or "keyhole" shape 3510B. Further, it should be understood that a single preform 3500 may utilize a plurality of different shaped attachment members 3510 simultaneously in the same elongate member 3520. The attachment members 3510 may be formed as a single monolithic structure by bending a single wire, or may be made by attaching individual attachment members 3510 to a single wire 3500 by soldering, welding, adhesives, mechanical clamping mechanisms or the like. Like the embodiments of preforms described above, the preform 3500 may be formed in a substantially two-dimensional, mono-planar shape and may include end portions that are curved, as described above in connection with FIGS. 15A-15D. Alternatively, the preform 3520 may be formed in a three-dimensional, helically extending form that approximates the shape of the graft 3530 to which it is to be attached (see FIG. 35B). As shown in the embodiment of the endoluminal prosthesis of FIG. 35B the preform 3520 is attached to the graft 3530 in a circumferentially and longitudinally extending manner such that the elongate member 3520 forms a plurality of longitudinally spaced apart turns, where each turn extends substantially 360 degrees around the outer surface of the graft 3530. Like the bends 1116 of FIG. 22, the attachment members 3510 of each turn are circumferentially aligned with the attachment members 3510 on the longitudinally adjacent turn(s). The two or three-dimensionally formed preform 3520 may be attached to the graft 3530 by sutures 3540 at least at the attachment members 3510.

In embodiments in which the preform 3520 is formed in a two-dimensional, substantially mono-planer form (with or without the end portions 130, 140 being curved, as described above), when the preform 3520 is wrapped in a circumferentially and longitudinally extending helical configuration and attached to the graft 3520, as shown in FIG. 35B, the preform 3520 causes the graft 3530 to be torqued or twisted ("torsioned") in the circumferential and longitudinal directions. However, in some embodiments, the graft 3520 may be torsioned in only a circumferential direction. This twisting of the graft 3530 occurs due to the twisting force exerted on the graft 3530 by the preform 3520 as the preform 3520 attempts to return to its flat equilibrium state and "unwrap" from the graft 3530. That is, because the preform 3520 is constrained in an elastically torqued state, the graft is torqued (torsioned) by a twisting force exerted by the torsioned preform 3520. The torque applied to the graft 3530 creates a plurality of tension folds 3515 in the graft material. The tension folds 3515 extend both circumferentially and longitudinally about the outer surface of the graft 3530 between longitudinally adjacent turns of the preform 3520. For example, the tension folds 3515A and 3515B extend between turns 3522A and 3522B, with the tension fold 3515A extending between attachment members 3510A and 3510D, and the tension fold 3515B extending between bends 3510B and 3510C. A relaxed fold 3517 may be present between the two tension folds 3515A, 3515B. For example, as shown in FIG. 35B, the relaxed fold 3517A may extend from the attachment member 3510B to the attachment member 3510C. The tension folds 3515 (shown as lines) and the relaxed folds 3517 essentially divide the graft 3520 into a plurality of interconnected cells 3519, with each cell 3519 having a fraction of the surface area of the graft 3520 as a whole.

While the embodiment of FIGS. 35A and 35B illustrates an endoluminal prosthesis having a constant, uniform diameter along its length, it should be understood that it is not limited thereto, and embodiments incorporating non-uniform, tapered sections are also contemplated. In such embodiments, the spacing of the attachment members 3510 may be adjusted such that when the preform 3520 is attached to the graft 3530, the attachment members 3510 remain circumferentially aligned for adjacent turn(s).

As stated above, the materials used in the manufacture of the device may be selected from commercially available materials. Preferred materials include those materials that can provide the desired functional characteristics with respect to mechanical load bearing, biological compatibility, modulus of elasticity, or other desired properties. In various embodiments, the elongate member 1114 may be formed from a metallic material selected from stainless steel, silver, platinum, palladium, gold, titanium, tantalum, iridium, tungsten, cobalt, chromium, cobalt-chromium alloy 1058, cobalt-based 35N alloy, nickel-based alloy 625, a molybdenum alloy, a molybdenum alloy including about 0.4% to about 0.8% of lanthanum oxide ($Li_2O_3$), and a nickel-titanium alloy, such as Nitinol, or other suitable materials as known in the art.

Returning to FIG. 22, the uniform section 1113 of the graft 1112 includes five turns 1122A-E and the tapered section has two turns 1124A, 1124B. As stated above, the turns are positioned upon the outer surface of the graft 1112 both longitudinally and circumferentially. The elongate member 1114 also includes two partial turns 1126 disposed at the ends of the tapered and uniform sections 1111, 1113 to provide support in at the portions of the graft 1112 that would otherwise be unsupported due to the "gaps" described above in connection with FIG. 2.

As shown in the embodiment of FIG. 22, the elongate member 1114 is attached to the graft in a left-hand helical configuration. In other embodiments, the elongate member 1114 may be attached to the graft 1112 in other configurations, including a right hand helix, etc. The bends 1116 of the turns of the elongate member 1114 are in circumferential alignment about the circumference of the graft 1112. For example, as shown in the FIG. 22, the bends 1116 of the turn 1122A are substantially circumferentially aligned with one or more of the bends 1116 of the remaining turns 1122B-E, 1124A-B, and 1126. In some embodiments, every bend of every turn may be substantially circumferentially aligned with the bends of longitudinally adjacent turns. In other embodiments, ever other bend of every turn may be substantially circumferentially aligned with every other bend of longitudinally adjacent turns. Note that in embodiments having widened angles, the bends may or may not be laterally aligned on the two-dimensional graft layout described above in connection with, for example, FIGS. 2, 4, and 8, or when formed in a three-dimensional shape as described above in connection with, for example, FIGS. 17B, 18B, and 19B.

As shown in FIG. 22, at least one bend 1116, and in the shown embodiment, substantially all of the bends 1116 on the turns are aligned with each other. For example, bend 1116A on turn 1124B is substantially circumferentially aligned with bend 1116E on turn 1122A. As will be discussed in further detail later, the alignment of the bends 1116 on the turns 1122A-E of the elongate member may help contribute to the reduction of kinking of the graft 1112 and occlusion of the lumen when the endoluminal prosthesis 1110 is bent or curved.

As set forth above, the elongate member 1114 includes a plurality of first 1118 and second 1120 struts. As the first 1118 and second struts 1120 converge towards the bends 1116 of the elongate member 1114, an angle at the bend is formed. In one embodiment utilizing an elongate member 1114 having widened angles, as described above and shown in, for example, FIGS. 17B, 18B, 19B, and Tables 1-3, when the elongate member 1114 is attached to the outer surface of the graft 1112 the angle between the bends 1116 is compressed from its relaxed, as-formed state, from a first angle to a second, more acute angle, and then attached to the graft 1112. Because the angles are attached to the graft 1112 in a compressed configuration, the elongate member 1114 is attached in a constrained state and exerts a torsional force or torque on the graft 1112 in the circumferential and longitudinal direction (e.g. a helically oriented force) as the angles of the elongate member tend to return to their equilibrium, relaxed (as formed), and widened state. In embodiments in which the elongate member 1114 is formed in a two-dimensional, substantially mono-planer form (with or without the end portions 130, 140 being curved, as described above), the graft 1112 may be torqued or twisted by virtue of the longitudinal and circumferential force exerted on the graft 1112 by the elongate member 1114 as it attempts to return to its flat equilibrium state and "unwrap" from the graft 1112. Note that any of the flat, two-dimensional preforms discussed in this application may exert such circumferential, or circumferential and longitudinal, e.g. helical, force on the graft, regardless of whether the angles are compressed from the first angle to the second angle. It should be understood that in some embodiments utilizing a flat, two-dimensional preform having widened angles, the torsional forces exerted on the graft 1112 include both of the above described components of torsional force. Other embodiments may only have one component of torsional force.

In the case of elongate members 1114 employing widened angles, the first angle between the bends 1116 in the relaxed, equilibrium state may be about 0% to about 80% greater than the second angle in the compressed state as attached to the graft 1112. The compression of the angles at the bends 1116 between the bends of the elongate member 1114 may be advantageous in reducing the amount of kinking in the prosthesis 1110 upon deployment in a bent or curved configuration. It is believed that the degree to which the graft 1112 is torqued or twisted contributes the endoluminal prosthesis' resistance to occlusion of the lumen of the graft. Thus, generally speaking, the greater the torque exerted on the graft, the greater the kink resistance. The amount of torque placed upon the graft material by the elongate member 1114 may range from about 0.0319 Ncm to about 0.0383 Ncm.

In some embodiments, the luminal occlusion resistance of the endoluminal prosthesis 1110 may be maximized when the percentage difference between the first and second angles of the bends 1116 is increased to about 80%. More particularly, the first angle between the bends 1116 of the elongate member 1114 in the relaxed state may be about 20% to about 60% greater than the second angle between the bends 1116 when the elongate member 1114 is attached to the graft 1112. In some embodiments, the first angle between the bends 1116 of the elongate member 1114 in the relaxed state may about 40% greater than the second angle between the bends 1116 when the elongate member 1114 is attached to the graft 1112. However, it is believed that the percentage variation between the angles in the relaxed state and when attached to the graft 1112 contributes to the amount of strain experienced by the endoluminal prosthesis 1110. Thus, compressing the angles of the bends 1116 to the extent that it introduces a degree of strain/stress that exceeds a particular stress/strain in the elongate member 1114 may be counterproductive from a fatigue standpoint.

As set forth above, the elongate member 1114 may be at least partially torqued, or twisted, upon attachment to the graft. The torque applied to the graft 1112 creates a plurality of tension folds 1115 in the graft material. The tension folds 1115 extend both circumferentially and longitudinally about the outer surface of the graft 1112 between longitudinally adjacent turns of the elongate member. For example, tension folds 1115A, 1115B extended between turns 1122A, 1124B, with the tension fold 1115A extending between bends 1116A and 1116B. Tension fold 1115B extends between bends 1116C and 1116D. A relaxed fold 1117 may be present between the two tension folds 1115A, 1115B. For example, as shown in FIG. 22, the relaxed fold 1117 may extend from the bend 1116B to the bend 1116C. The tension folds 1115 and the relaxed folds 1117 essentially divide the graft 1112 into a plurality of interconnected cells 1119 having a fraction of the surface area of the graft 1112 as a whole.

As described above in connection with FIGS. 1A-E, throughout the uniform section 1113 of the graft 1112, the first struts 1118 are substantially the same length and the second struts 1120 are substantially the same length, with the length of the first struts 1118 being longer than the length of the second struts 1120. In alternative embodiments, the length of the second struts 1120 may be shorter than length of first struts 1118. The angle formed between the first 1118 and second 1120 struts at the bends may also be substantially uniform. The angle formed between the bends 1116 connecting first 1118 and second struts 1120 may be between about 20 and about 120 degrees, and may be between about 45 and about 90 degrees. In the embodiment of FIG. 22, the angle is about 50 degrees. The radius of curvature for the bends 1116 may be 0.019 inches (0.48 millimeters). Each turn of the elongate member 1114 has a predetermined number of bends extending 360 degrees around a central axis. The predetermined spacing may range from about 0 to about 8 millimeters. In some embodiments, the predetermined spacing between longitudinally adjacent turns of the elongate member 1114 may be about 4 mm, and may be oriented at a predetermined circumferentially and longitudinally extending pitch as described above. In addition, the predetermined number of bends 1116 on each turn may range from 2 and 9 bends 1116 depending on a number of different construction variables. The number of bends 1116 in each turn may be between 4 and 6 bends, and in the embodiment shown in FIG. 22, the number of bends 1116 in each helical turn of the elongate member 1114 is five.

The spacing (S) between each longitudinally adjacent turn 1122 is kept generally constant throughout the uniform section 1113 of the graft 1112. This uniform spacing may provide a sufficient surface area of graft material between the two aligned bends to fold or compress in a localized and controlled manner when the endoluminal prosthesis 1110 is bent or curved. As will be discussed in further detail below, this localized and controlled compression or folding of the graft 1112 helps maintain the lumen in a substantially open configuration even when the endoluminal prosthesis 1110 is bent. In the embodiment shown in FIG. 22, throughout the uniform section 1113, the length of the struts 1118, 1120 are generally the same for each turn 1122, where the first struts 1118 have a length of about 7.5 mm and the second struts have a length of about 9.5 mm. As stated above, the bends 1116 on the respective turns 1122 may all be aligned circumferentially.

Throughout the tapered section 1111 of the endoluminal prosthesis 1114, the first struts 1118 are longer in length than the second struts 1120. As described above in connection to the preform 100B, the angle between the converging struts may be progressively larger as the diameter of the tapered section 1111 increases. This may occur for each turn of the elongate member 1114 in the second section. Turn 1124B includes an angle between a pair of first and second struts 1118, 1120 of a first bend 1116, which is less than the angle between the pairs of first and second struts 1118, 1120 of the turns 1122A-E in the uniform section of the graft 1112. The first and second struts of this first bend are directly connected to turn 1122A in the uniform section 1111 of the graft 1112. In one embodiment, the ratio between the length of the first and second struts 1118, 1120 in the tapered section of the graft 1112 is substantially the same for each pair of first and second struts 1118, 1120. In another embodiment, the lengths of each successive first and second struts 1118, 1120 in the tapered section of the graft 1112 may be increased by a progressively smaller amount moving in the direction from a first end of the tapered section 1111, which is connected to the uniform section 1113, toward a second end. In still another embodiment the ratio between the length of the first and second struts 1118, 1120 in the tapered section 1111 of the graft 1112 may be the same for each pair of first and second struts 1118, 1120.

Figure 23:
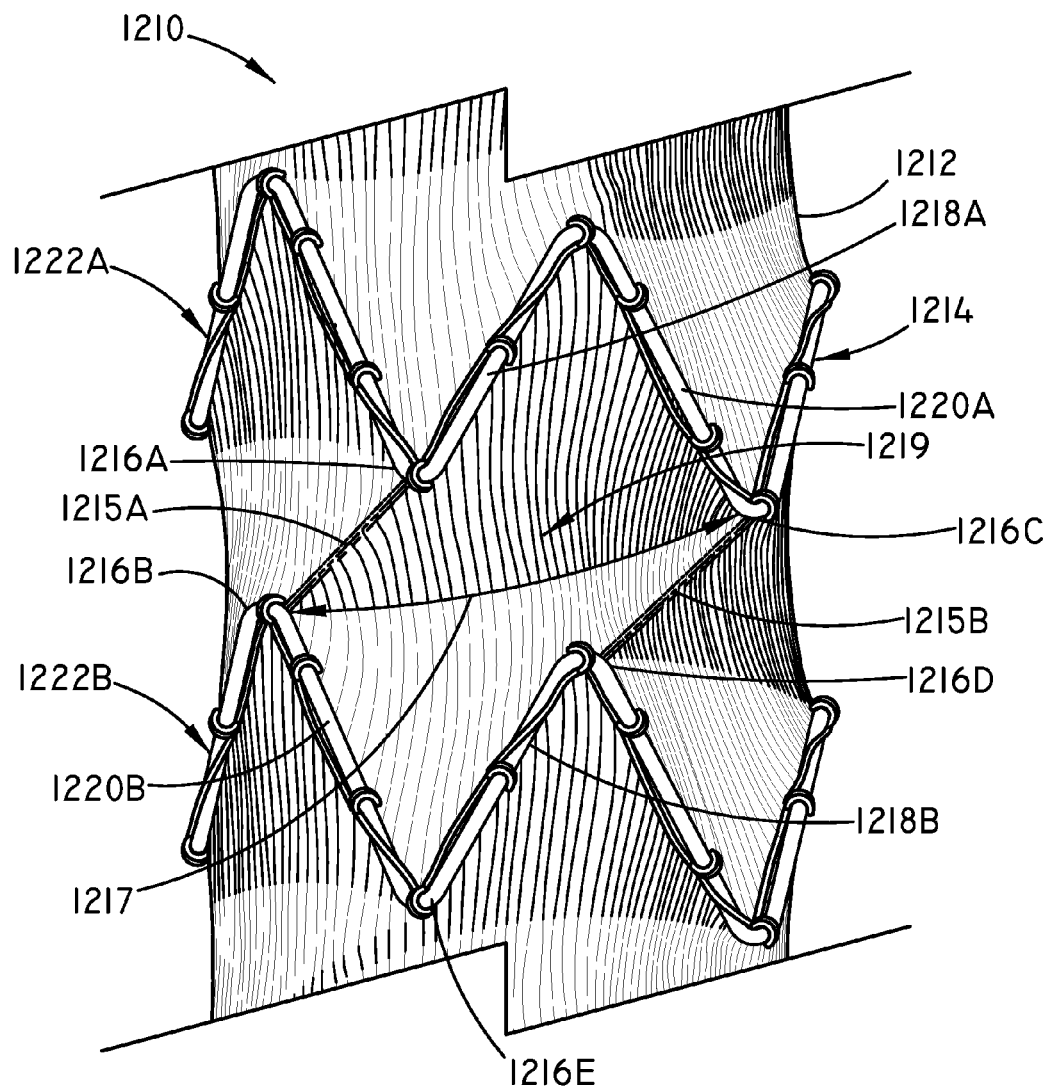
FIG. 23 illustrates a cell located on the outer surface of the endoluminal prosthesis of FIG. 22.

The endoluminal prosthesis 1110 also includes a plurality of interconnected cells 1119. FIG. 23 illustrates a cell 1219 in greater detail. The endoluminal prosthesis 1210 includes graft material 1212, and an elongate member 1214 attached to the graft 1212 forming a plurality of turns 1222A, 1222B. Tension folds 1215A, 1215B extend between the longitudinally adjacent turns 1222A, 1222B. The tension fold 1215A extends from the bend 1216A to the bend 1216B, while the tension fold 1215B extends from the bend 1216C and the bend 1216D. The cell 1219 is positioned in the space between the turns 1222A, 1222B. As shown in FIG. 23, each cell 1219 is bounded by four sides: a first end of the boundary that is defined by tension fold 1215A and the first strut 1218A; a second end of the boundary that is defined by second strut 1220A; a third end of the boundary is defined by the tension fold 1215B and the first strut 1218B; and a fourth end of the boundary is defined by second strut 1220B. Within the boundary of the cell 1219, a relaxed fold 1217 is present. The relaxed fold 1217 extends both circumferentially and longitudinally between bend 1216*b* and bend 1216*c*. The relaxed fold 1217 and tension folds 1215A, 1215B are created due to the torque placed upon the graft 1212 by the elongate member 1214, as the elongate member 1214 attempts to return to its relaxed state. The degree of torque exerted on the graft 1212 by the elongate member 1214 influences the degree to which the tension folds 1215 and the relaxed folds 1217 are present. That is, where the torque is high, the tension folds 1215 and the relaxed folds 1217 are more pronounced.

Figure 30:
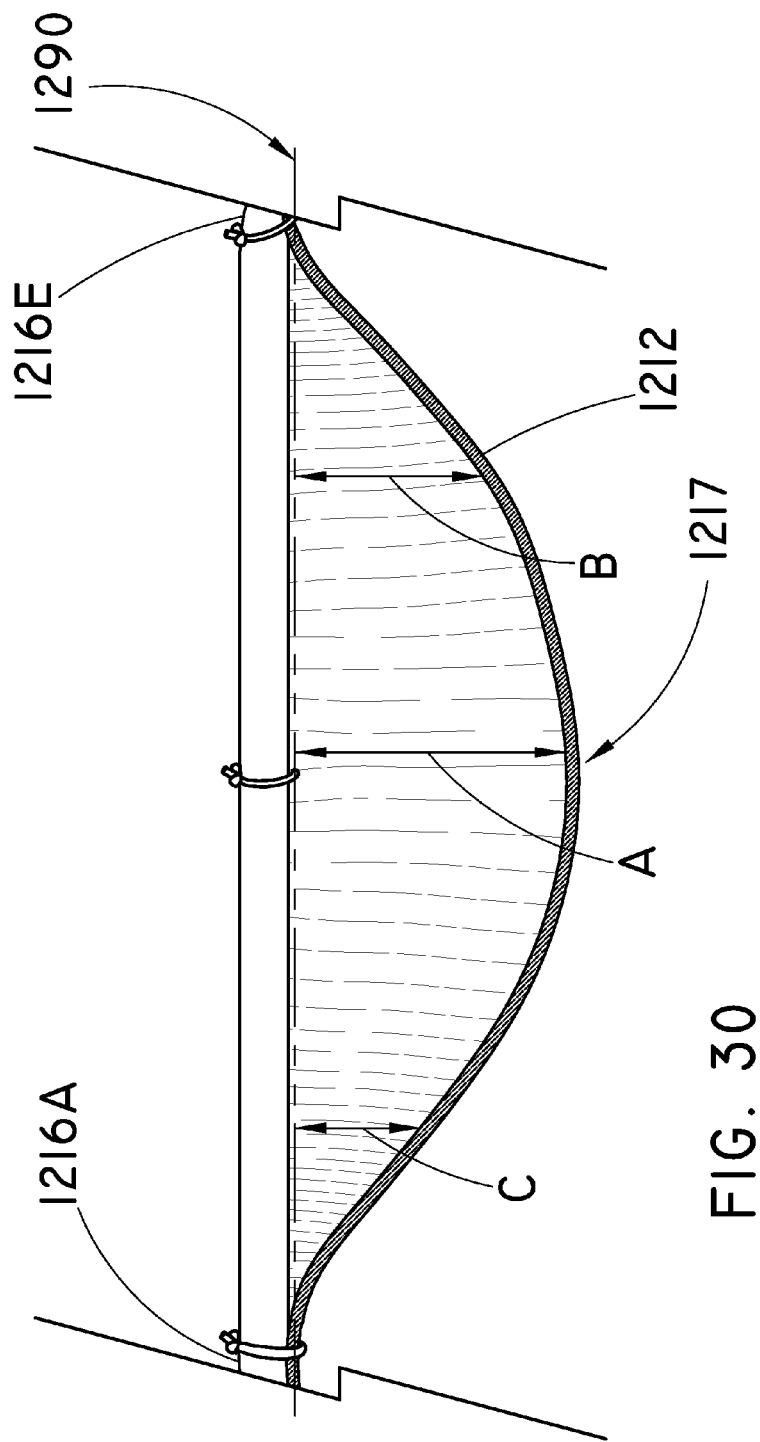
FIG. 30 illustrates a cross section of the endoluminal prosthesis of FIG. 23.

FIG. 30 illustrates a cross-section of the cell 1219 taken along a line extending from the bend 1216A and the bend 1216E of FIG. 23. As shown in FIG. 30, the relaxed fold 1217 causes the outer surface of the graft 1212 within the cell 1219 to have a generally concave configuration extending radially inwardly toward the center of the endoluminal prosthesis 1210. That is, the distance A between a longitudinally extending plane 1290 tangent to the surface of the graft 1212 and the relaxed fold 1217 is greater than a distance B or C between the graft 1212 and the same plane 1290. Concurrently, the tension folds 1215 may cause the outer surface of the graft material 1212 disposed about the tension fold 1215 to have a somewhat convex configuration. The contour of the graft 1212 within the cell(s) 1219 help ensure localized, uniform folding centered at the relaxed folds 1217 when the prosthesis 1210 is bent. As will be discussed below, this localized folding helps to ensure that no portion of the graft 1212 extends significantly radially inward to cause the graft 1212 to kink and occlude the lumen.

Figure 24:
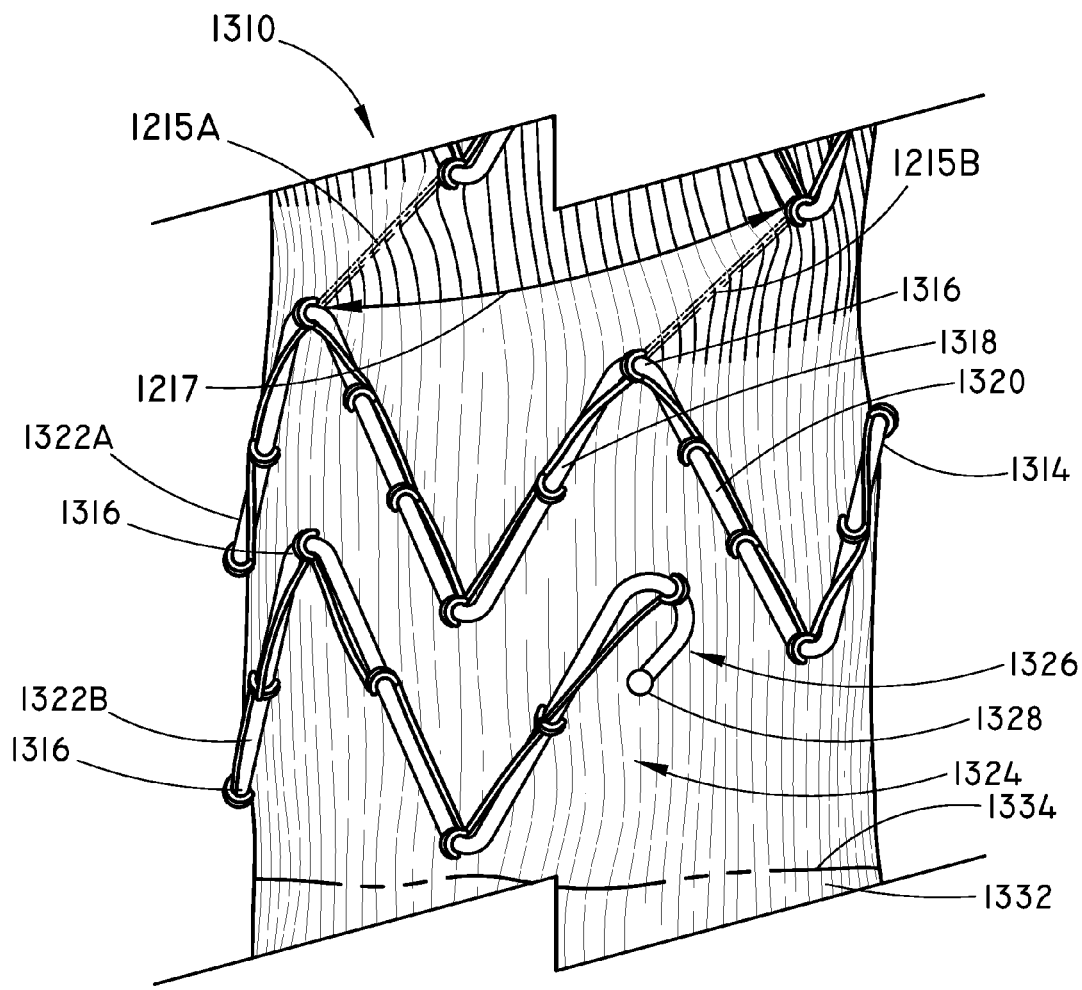
FIG. 24 illustrates an end portion of the endoluminal prosthesis of FIG. 22.

Turning to FIG. 24, an end portion 1324 of the elongate member 1314 is shown. The end portion 1324 is located near the final turn of the elongate member 1314. The final turn 1322B of the elongate member 1314 consists of a plurality of bends 1316 connecting a pair of first 1318 and second struts 1320, where the angle formed by the converging struts is substantially the same. In addition, the end turn 1322B may also be disposed such that it is longitudinally level with the longitudinally adjacent turn 1322A. As described above, this configuration ensures that the graft is supported below the "gap" formed below the last turn 1322 of the end sections of the endoluminal prosthesis 1310 (e.g. the uniform section(s) or tapered section, depending on the configuration). In other embodiments, the end portion 1326 of the member may have other suitable configurations. A transition line 1334, which identifies an end of the sealing stent disposed closest the end turn of the elongate member, is located between the end turn 1322B of the elongate member 1314 and the first end of the graft. The transition line 1334 and the end turn 1322B of the elongate member 1314 may be separated by a predetermined distance. This distance may range from about 1 mm to about 3 mm. In some embodiments, the distance between the end turn 1322B and the transition line is about 1 mm. This distance between the end turn 1322B and the transition line 1334 may allow for adequate spacing between the turn and the sealing stent within the interior surface of the graft to allow for flexibility of the graft between the elongate member and the sealing stent. As discussed above in connection with FIGS. 15A-15D, the end turn 1322B may be curved in a three dimensional shape prior to attachment to the graft 1312. This three-dimensional shape promotes both a circular lumen with the endoluminal prosthesis and prevents the end turn from protruding radially inward and partially occluding the lumen. The preformed, curved shape also ensures that the end point will not extend radially outward away from the graft 1312 to form a feature that could be potentially traumatic to the vessel in which the graft 1312 is placed.

Figure 25A:
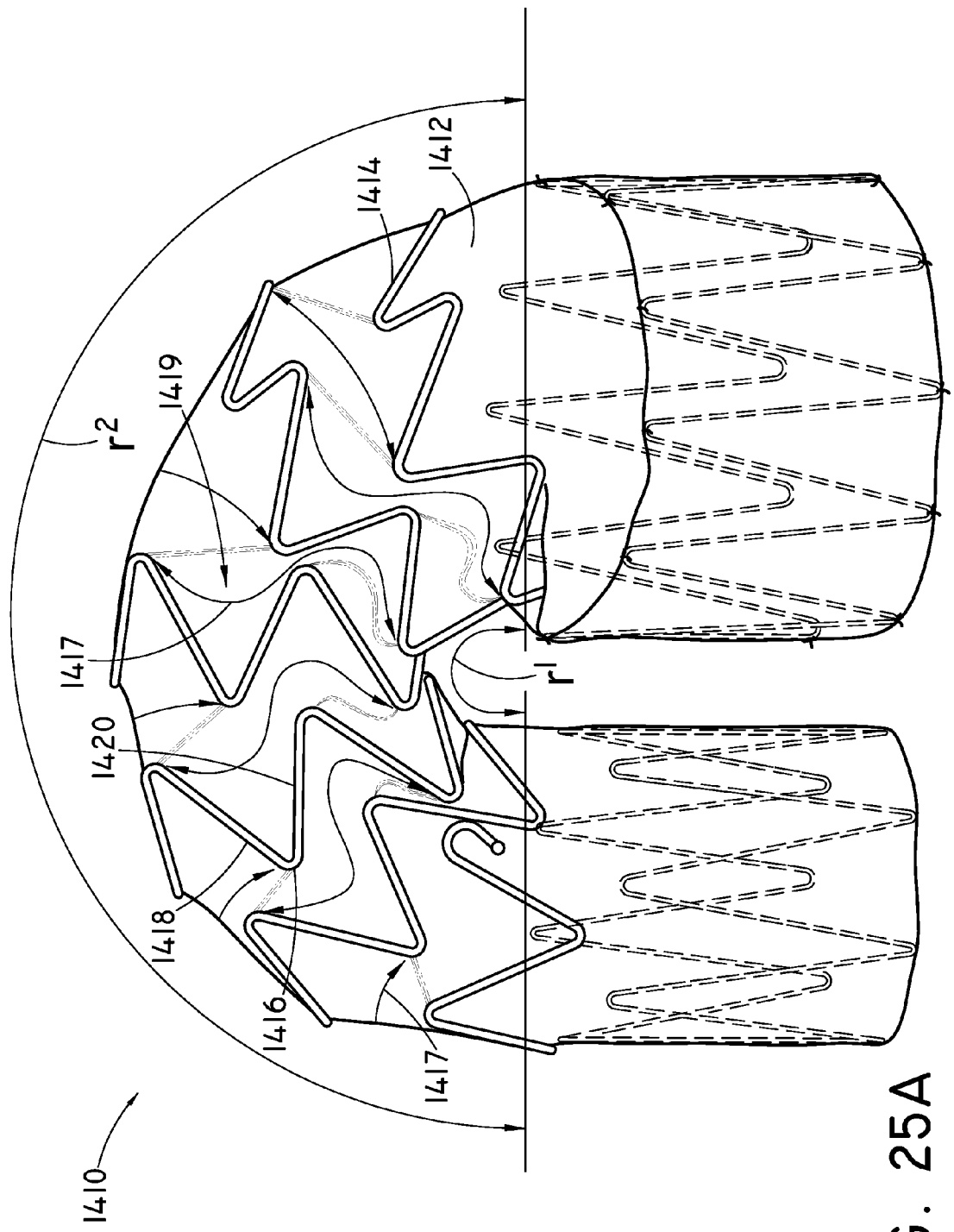
FIGS. 25A-B illustrate the endoluminal prosthesis of FIG. 22 in a second, bent condition.
Figure 25B:
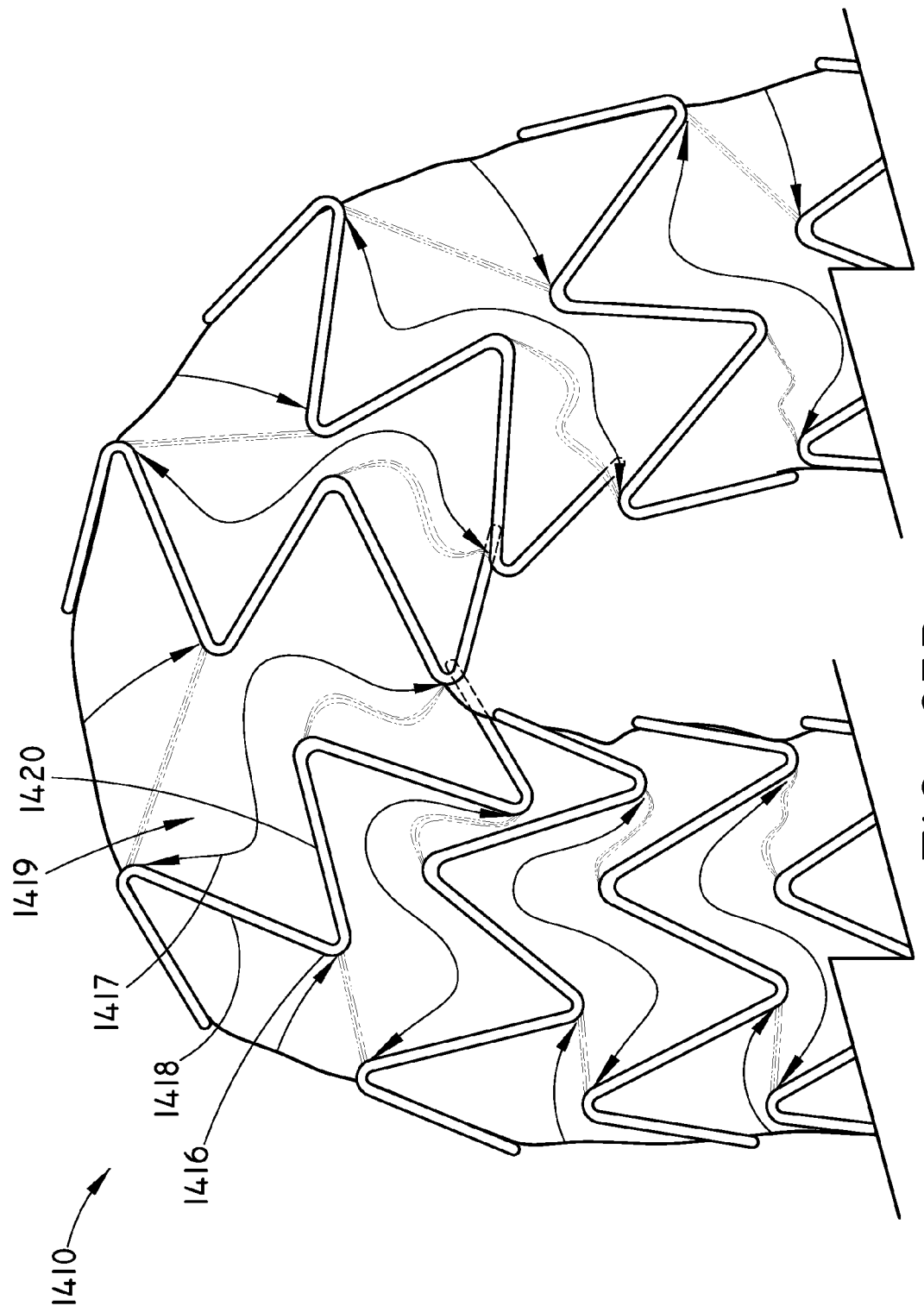
Figure 27:
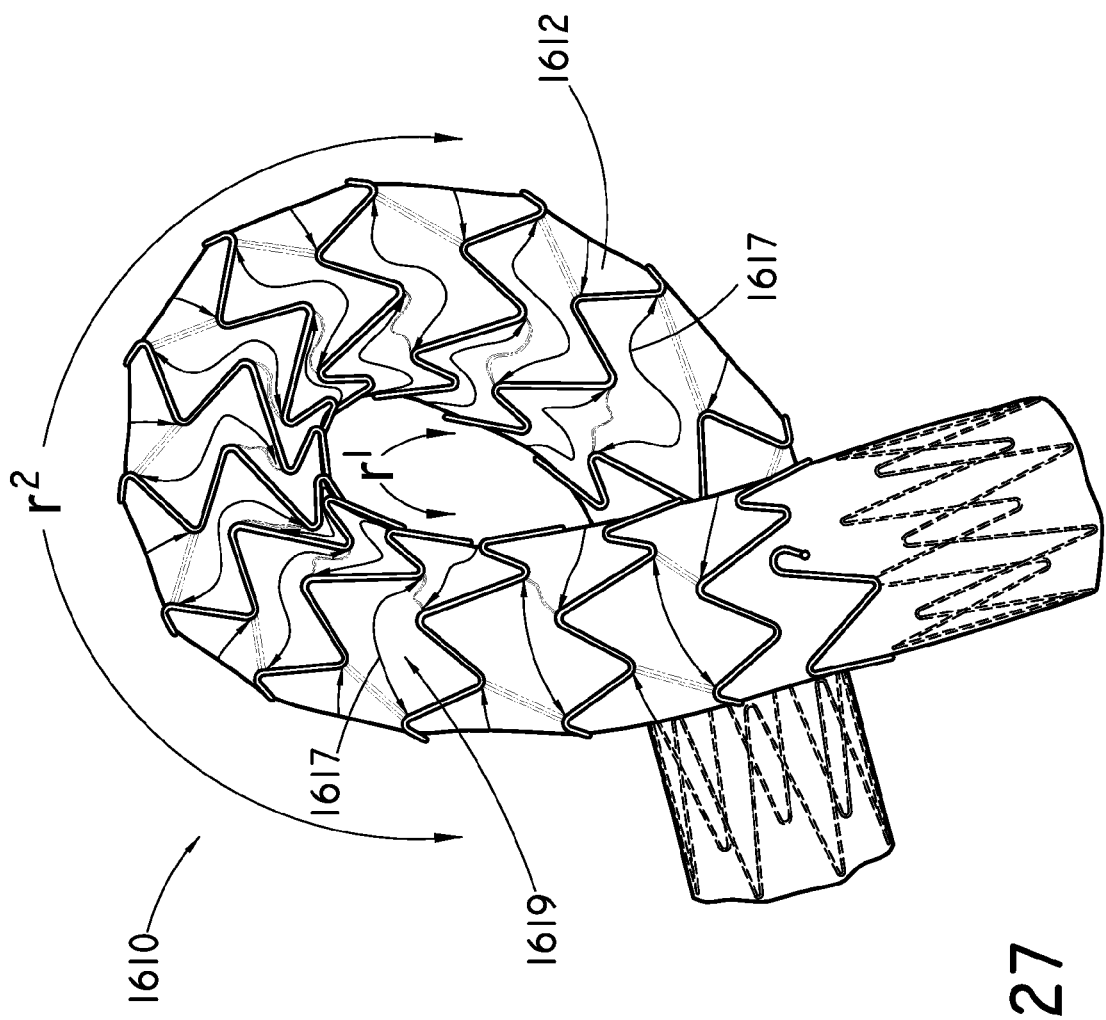
FIG. 27 illustrates the endoluminal prosthesis of FIG. 26 in a second, bent condition.

FIGS. 25A-25B and 27 show an embodiment of the present invention in a second configuration. As shown in FIG. 25A-25B, the endoluminal prosthesis 1410 is bent such that an interior radius and an exterior radius are present, where the interior radius $r_1$ is smaller than the exterior radius $r_2$ of the graft. The elongate member 1414 has a plurality of bends 1416, or apices, which connect a pair of first 1418 and second struts 1420 at an angle. A plurality of cells 1419 are formed along the graft 1412, including the interior radius $r_1$ and the exterior radius $r_2$. As described above in connection with FIG. 23, the tension folds 1415 form part of the boundary of the cell

1419. Within the boundary of the cell 1419, a relaxed fold 1417 is present. Referring now to FIG. 27, as the endoluminal prosthesis 1610 is placed into the second configuration, the cells 1619 along the interior radius $r_1$ begin to compress about the relaxed folds 1617. Concurrently, the tension folds 1615 and the relaxed folds 1617 on the exterior radius $r_2$ begin to expand and flatten. These concurrent actions allow for uniform folding about the length of the graft 1619. Because the cells 1619 divide the overall surface area of the graft 1612 into proportionately small areas that are relatively isolated from each other, only the portion of the graft 1612 disposed in each cell 1619 is able to fold. Moreover, because the cells are substantially isolated from each other, individual folds within even adjacent cells 1619 are substantially prevented from propagating into adjacent or nearby cells 1619. Thus, the compression force exerted on the portion of the graft 1612 corresponding to $r_1$ by the bending forces is not spread over a large area of the graft 1612, and a significant fold or kink that could occlude the lumen is prevented. Such kinking is undesirable as it may close the lumen of the graft 1612 and the endoluminal prosthesis 1610 may have to be repositioned by a later procedure. The localized, controlled folding of the graft 1612 within each of the cells 1619 along the interior radius allows the lumen to remain substantially open. This improvement is significant as it reduces possibility of kinking when the endoluminal prosthesis is deployed.

Figure 26:
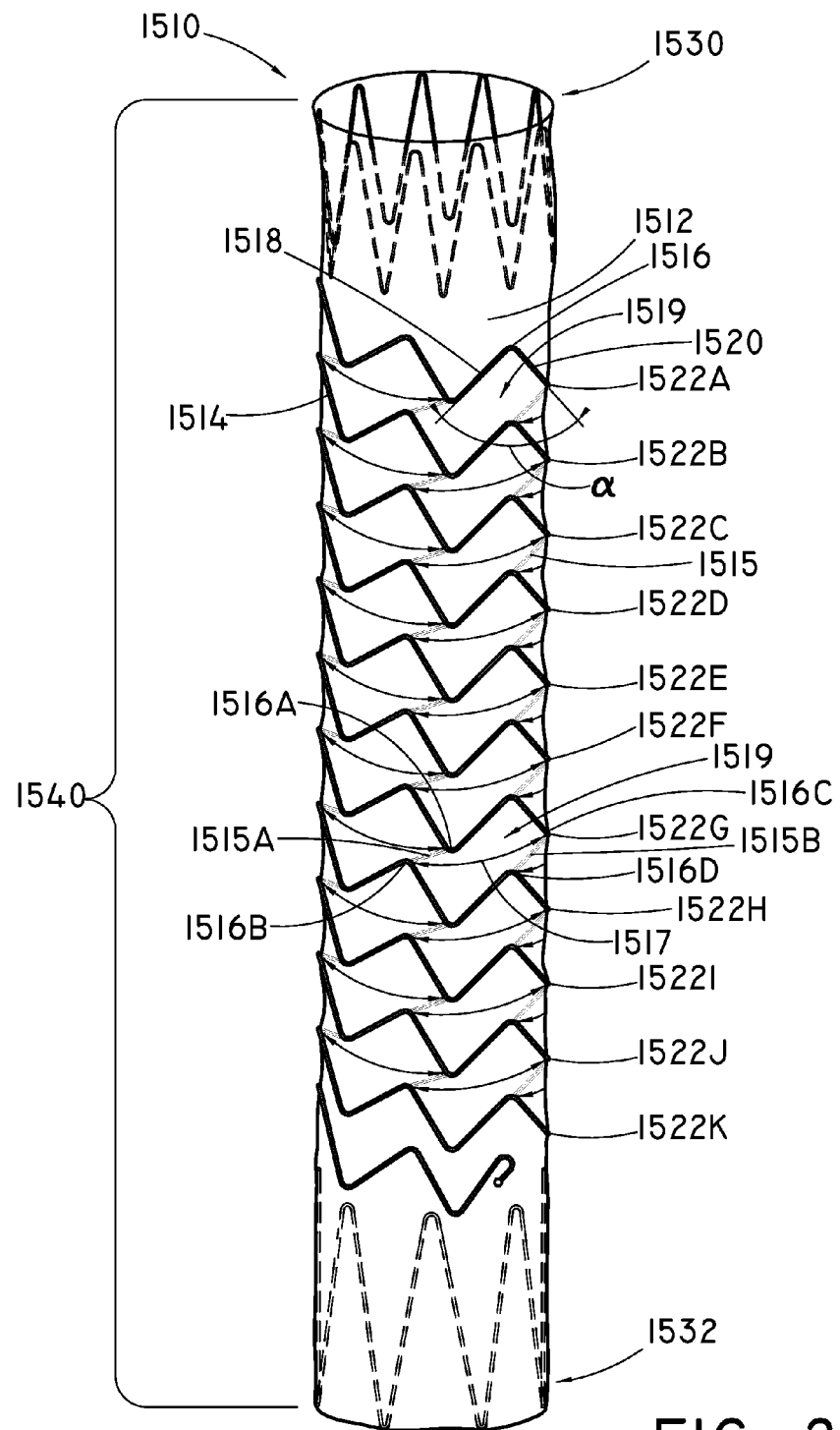
FIG. 26 illustrates an endoluminal prosthesis having a uniform section throughout the length of the prosthesis in a first condition.

FIG. 26 illustrates another embodiment of the endoluminal prosthesis 1510. The endoluminal prosthesis 1510 has a generally uniform diameter throughout the length of the graft 1512. As shown in FIG. 26, the endoluminal prosthesis 1510 is in a first condition where the endoluminal prosthesis is substantially straight. The elongate member 1514 is attached to the graft 1512 longitudinally and circumferentially. The elongate member 1514 has a plurality of bends 1516, or apices, which connect a pair of first and second struts 1518, 1520 at an angle. Each of the first struts 1518 extend from adjacent bends 1516 in a first direction. In addition, each of the second struts 1520 extends between adjacent bends in a second direction, where the second direction is different than the first. Each of the first struts 1518 have substantially the same length and each of the second struts substantially the same length, with the length of the first struts 1518 being longer than the length of the second struts 1520. In alternative embodiments, the length of the second struts 1520 may be shorter than length of first stent 1518. In addition, the angle formed between the first 1518 and second 1520 struts at the bends may be generally uniform. The angle between first 1518 and second struts 1520 and the bends 1516 bends may be between about 20 and about 120 degrees, and may be between 45 and 90 degrees.

The elongate member 1514 may be attached to the graft 1512 by sutures, or the like, as described above. In some embodiments, the sutures may only be applied at the bends 1516 of the elongate member 1514 to the graft 1512. In other embodiments, the sutures may be applied at the bends 1516, as well as along the first and second struts 1518, 1520 of the elongate member 1514. The endoluminal prosthesis 1510 may also include a first end 1530 and a second end 1532. Within each of these ends, a sealing stent may be placed within the interior surface of the graft 1512. The sealing stents may be attached to the first end 1530 and the second end 1532 of the graft 1512 by suturing or the like, as described above in connection with the elongate member.

The endoluminal prosthesis includes a plurality of turns 1522A-K. As stated above, the turns are positioned upon the outer surface of the graft both longitudinally and circumferentially. As shown in the embodiment of FIG. 26, the elongate member 1514 has the configuration of a left-hand helix. In other embodiments, the elongate member 1514 may be placed in other configurations upon the graft material, including a right hand helix. The turns in the first section of the endoluminal prosthesis 1510 are in alignment about the circumference of the graft 1512. As shown in the FIG. 22, at least one bend 1516 of turn 1522A is circumferentially aligned with a corresponding bend 1516 of turns 1522B. The endoluminal prosthesis 1510 also includes a plurality of cells 1519. Tension folds 1515A, 1515B extend between the longitudinally adjacent turns 1522G, 1522H. The tension fold 1515A is interconnected with bends 1516A and 1516B, while the tension fold 1515B is interconnected with bends 1516C and 1516D. As described above, the relaxed fold 1517 and tension folds 1515A, 1515B are created due to the torque placed upon the graft 1212 by the elongate member 1514 as it attempts to return to its relaxed state. The cell 1519, for example, is positioned in the space between the turns 1522g, 1522h. The cell 1519 includes a boundary formed by four ends as described above, and will therefore not be described again. In operation, the embodiment of FIG. 26 functions in essentially the same way as the embodiments described above to prevent kinking and will therefore not be described again.

Figure 28:
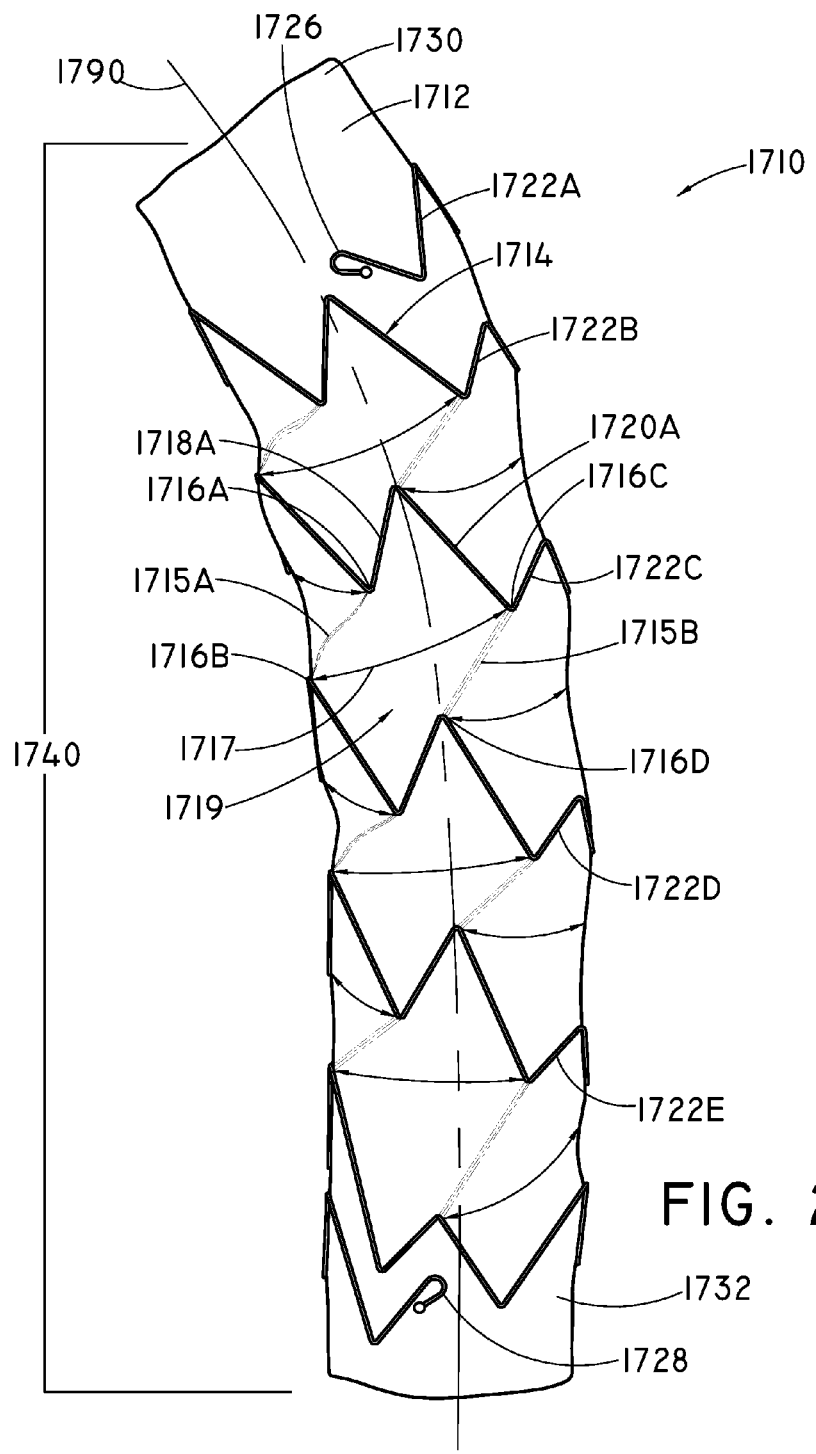
FIG. 28 illustrates an endoluminal prosthesis having a uniform section throughout its length, where the elongate member has a preformed curve.

FIG. 28 depicts another embodiment of the endoluminal prosthesis 1710. In this embodiment, the endoluminal prosthesis 1710 has a generally uniform diameter throughout the length of the graft 1712 in a first condition 1740. In other embodiments, the endoluminal prosthesis 1712 may form a taper throughout the length of the graft to conform to the anatomy of a desired body vessel. The elongate member 1714 in this embodiment includes a preformed curve about a central axis 1790. This curve in the elongate member 1714 may be accomplished by heat-setting the elongate member 1714 at a temperature suitable for the material of the elongate member 1714. In some embodiments, the curved elongate member 1714 applies a curve to the graft 1712 upon attachment to the graft 1712. In other embodiments, the graft 1712 may have a preformed curve prior to the attachment of the elongate member 1714, but the curve is dissipated once the elongate member 1714 is attached to the graft 1712. This preformed curve may be advantageous when the endoluminal prosthesis is placed in a curved vessel, such as the thoracic arch as the natural, unloaded position more closely approximates the shape of the target body vessel and exerts less force against the vessel as the elongate member 1714 tends to return to its equilibrium or relaxed configuration. Because less force is introduced into the elongate member 1714, the stress/strain experienced by the elongate member is also reduced, thereby increasing the fatigue life of the endoluminal prosthesis 1710.

Figure 29:
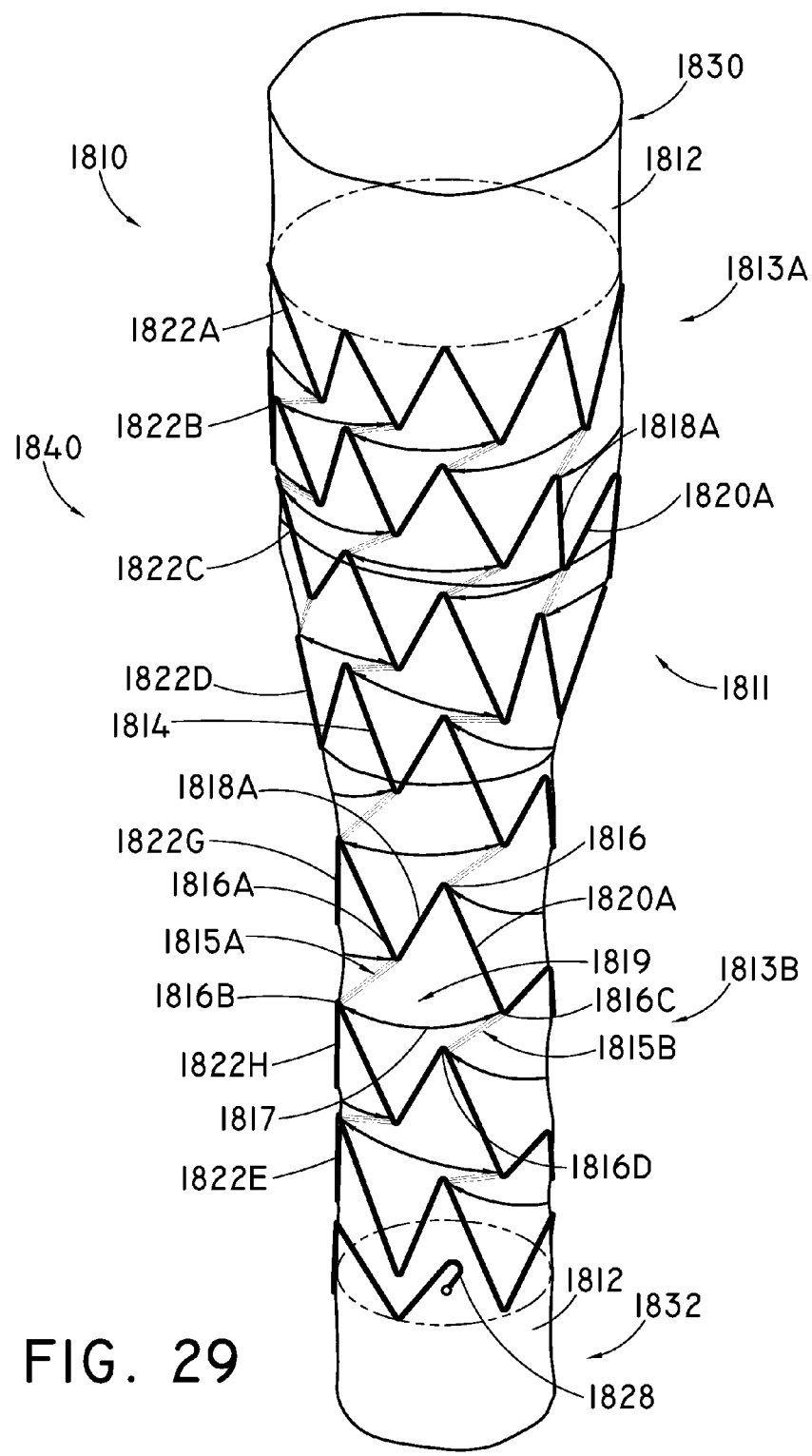
FIG. 29 illustrates an endoluminal prosthesis having two uniform sections and one tapered section in a first condition.

FIG. 29 depicts another embodiment of the endoluminal prosthesis 1810 having two uniform sections with two generally uniform diameters 1813A, 1813B, and a tapered section 1811 in which the diameter varies throughout the length of the section 1811. In some embodiments, the first uniform section 1813A has a diameter of about 11 mm and a length from about 34 to about 51 mm. In some embodiments, the second uniform section 1813B has a diameter of about 9 mm and a length of from about 34 to about 51 mm. The tapered section 1811 may have a diameter that ranges from about 9 mm at one end to about 13 mm at another end to conform to a desired body vessel in which the prosthesis 1810 is to be implanted. The length of the tapered section may be from about 3 to about 34 mm. The endoluminal prosthesis 1810 also includes a first end 1830 and a second end 1832. Within each of these ends, a sealing stent is placed within the interior surface of the graft 1812. The sealing stents may be attached to the first end 1830 and the second end 1832 of the graft 1812 by sutures or the like.

As shown, the endoluminal prosthesis 1810 is in a first condition 1840, where the endoluminal prosthesis is substantially straight. The endoluminal prosthesis 1840 may also have a second, curved condition having an interior radius and an exterior radius. The elongate member 1814 is attached to the graft longitudinally and circumferentially. The elongate member 1814 includes a plurality of turns throughout both the first section of the graft and the second section of the graft. The endoluminal prosthesis includes a plurality of turns 1822, with the turns being positioned upon the outer surface of the graft in a longitudinally and circumferentially extending manner. As shown in the embodiment of FIG. 29, the elongate member 1814 has the configuration of a left-hand helix. In other embodiments, the elongate member 1814 may be placed in other configurations upon the graft material, including a right hand helix. At least one bend 1816 of the turns 1822 in the first section of the endoluminal prosthesis 1810 are in circumferential alignment with at least one bend 1816 of adjacent turns, as described in the aforementioned embodiments. Like the embodiments described above, the elongate member 1814 has a plurality of bends 1816 connecting first and second struts 1818, 1820. The elongate member 1814 of FIG. 29 configured and attached to the graft 1812, and alleviates kinking of the graft 1812 using tension folds 1815 and relaxed folds 1817 within discreet cells 1819 in a similar manner to the embodiments described above, and will therefore not be described again.

Other embodiments of the endoluminal prosthesis may be manufactured having any combination of "straight" or "tapered" sections, depending on the vasculature of the recipient of the device.

Figure 31:
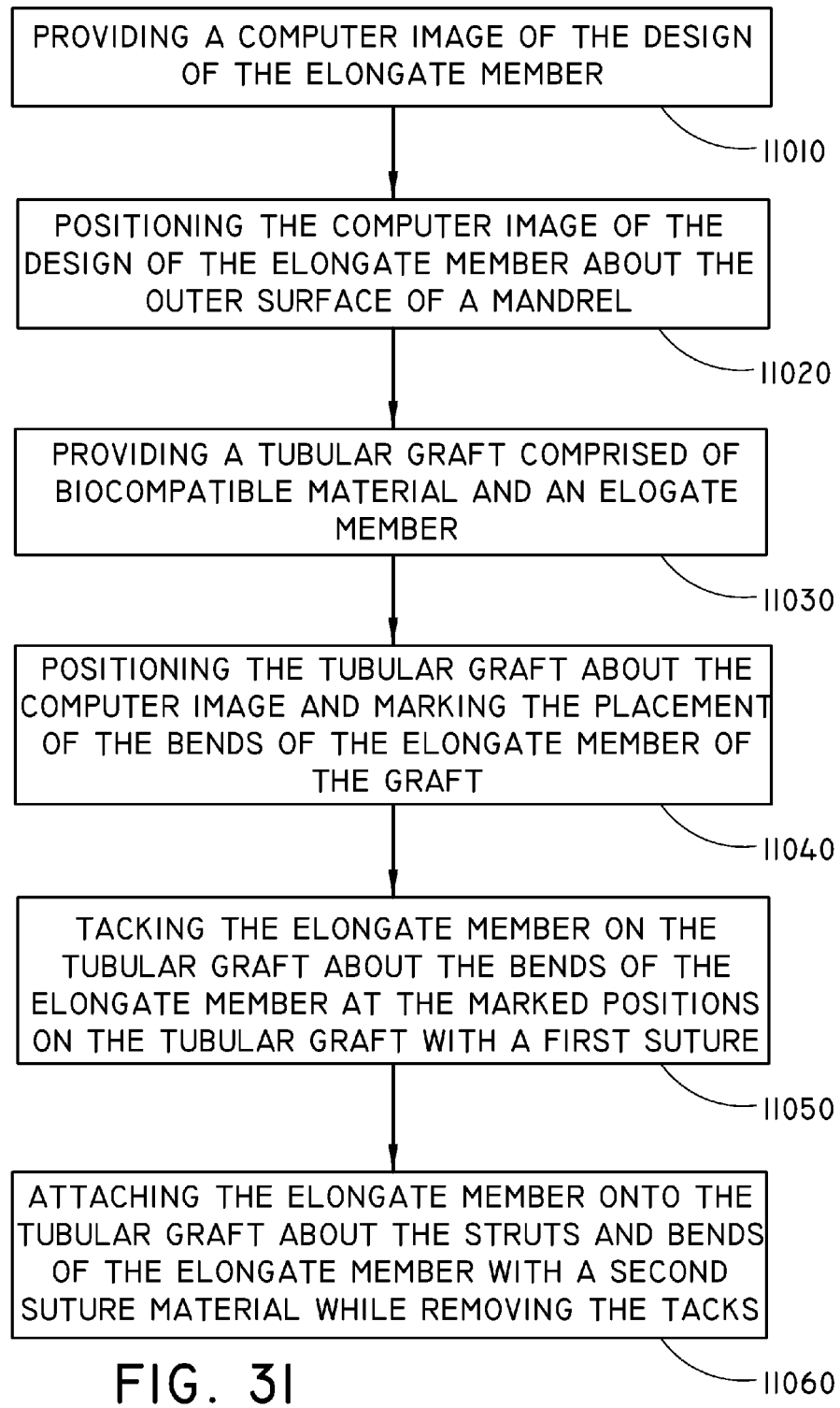
FIG. 31 is a flow chart of a method of making an endoluminal prosthesis.
Figure 32:
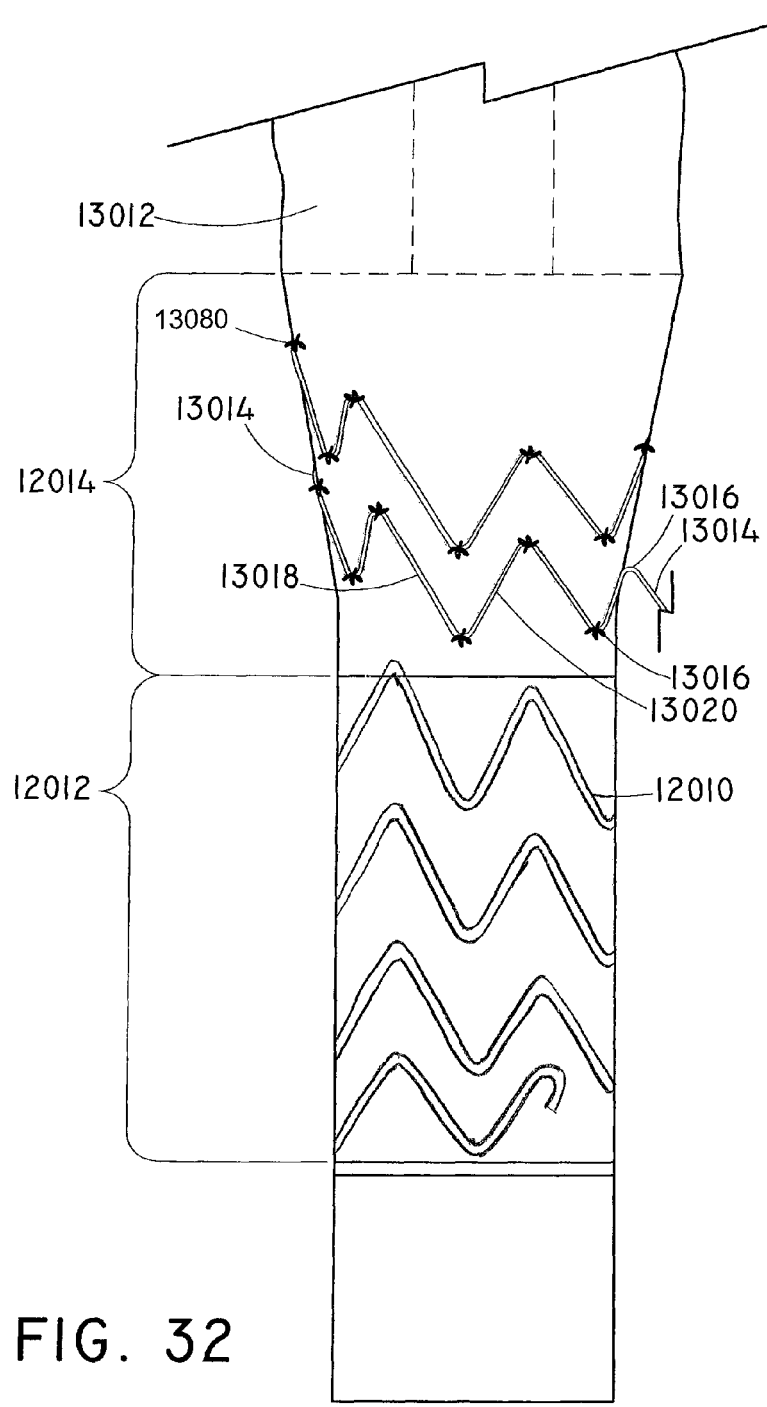
FIG. 32 illustrates a computer generated image of the elongate member used to manufacture the endoluminal prosthesis.

Referring now to FIGS. 31-34, an exemplary method for making the endoluminal prostheses of any of the above-described embodiments is shown. Referring to FIG. 31, a two-dimensional computer generated image of the design of the elongate member, such as those shown in, for example, FIGS. 2 and 5, is created using any suitable computer design software, such as AutoCAD® (Autodesk, Inc., San Rafael, Calif.) (Act 11010). Referring to FIG. 32, the computer generated image 12010 is printed out on a sheet of paper and has a plurality of sections corresponding to various portions of the elongate member 13014 of the graft and/or preform. For example, the computer generated image 12010 may have a section 12012 corresponding to a substantially uniform diameter section of the graft or preform and may have a section 12014 corresponding to a tapered section of the graft or preform. The computer generated image 12010 may be formed into a tubular shape. The tubular shape is representative of the type of endoluminal prosthesis to be manufactured, or stated differently, the shape is representative of the anatomy of a body vessel in which the device is to be implanted. In this particular embodiment, the tubular shape has a uniform section 12012 and a tapered section 12014. The computer generated image 12010 is created to be used as a guide in order to properly attach an elongate member to an actual graft.

Figure 33:
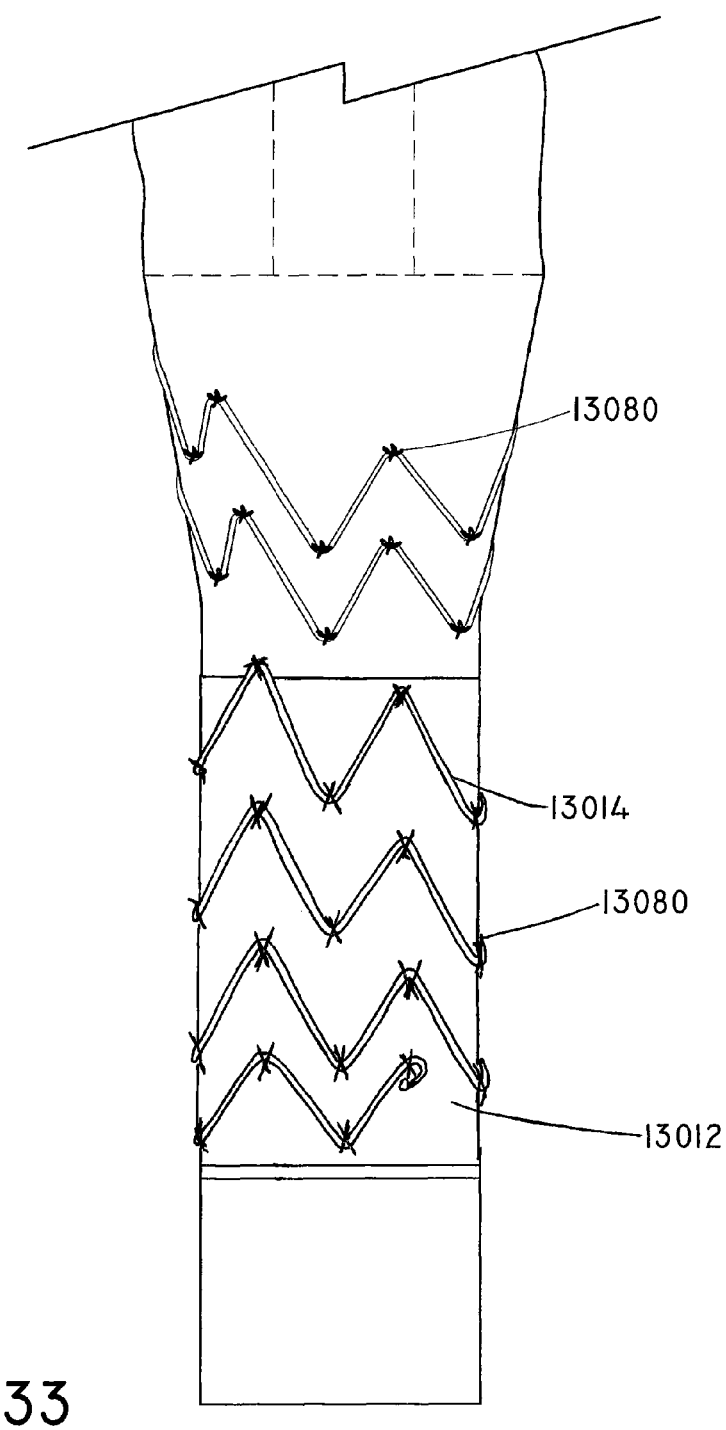
FIG. 33 illustrates the elongate member tacked onto the graft material during the making of the endoluminal prosthesis.

Referring back to FIG. 31, the next act 11020 involves placing the computer generated image of the design of the elongate member about the surface of a mandrel. The mandrel has a shape that substantially corresponds to the tubular shape of the desired three-dimensional graft and the two-dimensional computer generated image 12010, as shown in FIG. 32. The mandrel is sized to be slightly smaller than the tubular generated image 12010 such that it can fit easily within the interior surface of the tube. The position of the bends and struts of the elongate member in the computer generated image 12010 is set in the desired "attached" position such that the desired angle between the pairs of first and second struts is achieved. Thus, in the event that an elongate member having widened angles is to be used, the compressed, narrower, "as attached" angles are utilized in the computer generated image 12010. Next a tubular graft material is provided to the mandrel and the computer generated image 12010 is set upon the outer surface of the graft 13012 and the mandrel (acts 11030, 11040). Alternatively, the computer generated image can be applied on the mandrel first and the graft 13012 can be overlaid on the mandrel and the computer generated image 12010. As shown in FIG. 33, the tubular graft 13012 is configured such that the manufacturer of the endoluminal prosthesis can see the computer generated image 12010, either because it is disposed externally of the graft 13012, or because the manufacturer can see the markings of the computer generated image 12010 through the graft material. In this way, the manufacturer is able to identify and/or mark the desired locations of the bends 13016 of the elongate member 13014 for placement on the graft.

As shown in FIGS. 32 and 33, after the locations are marked/identified, the elongate member 13014 is "tacked" onto the tubular graft 13012 using one or more sutures 13080 or the like (act 11050). This tacking may be achieved by sewing a first suture material 13080 about the bends 13016 of the graft. The tacking of each bend 13016 is performed one at a time as the elongate member 13014 is wound about the tubular graft 13012. Each suture 13080 is placed at the marked location. The elongate member 13014 is in a relaxed state prior to being tacked to the graft. As stated above, the angles between the pairs of first 13018 and second 13020 struts in the relaxed state may be from about 0% to about 80% greater than that attachment angle, or between about 40% and about 60%. In one embodiment, the angle may be increased by about 40%. In the case that the angles have been formed to be wider than the desired "as attached" angle, the elongate member 13014 is partially compressed to the desired attachment configuration and angle during the tacking process. In addition, if the elongate member 13014 is a two-dimensional, flat preform, the elongate member 13014 may also be wrapped, or torsioned during the tacking process while placing the elongate member 13014 onto the graft. This torsion moves the elongate member 13014 out of its plane of formation and stores energy within the elongate member 13014.

Next, the sutures 13080 may be optionally removed from the graft material, and then (additional) sutures are added at the bends and in some embodiments, the struts to attach the elongate member 13014 to the graft 13012. As shown in FIG. 34, sutures may be sewn about the bends of the elongate member, as well as the pairs of first and second struts. The sewing of the sutures 13080 maintains the partial compression of the bends 13016 of the elongate member 13014 while the elongate member 13014 is attached to the graft 13012. While the elongate member 13014 is being sewn (attached) to the graft 13012, at least one of the bends 13016 on a selected turn 13022, and in some embodiments, all of the bends 13015 on all the turns, are aligned with the bends 13016 on the longitudinally adjacent turns 13022. The longitudinal and circumferential placement of the partially compressed elongate member 14014 creates the plurality of relaxed folds and tension folds discussed in connection with the embodiments of the endoluminal prosthesis described above.

An endoluminal prosthesis comprising:
a tubular graft comprising a first section, a second section, and a lumen defined therein, the first section having a uniform diameter and the second section having a diameter that increases throughout forming a taper;

an elongate member having a plurality of torqued turns circumferentially and longitudinally attached to the graft, the elongate member comprising a plurality of bends, each bend connecting a pair of first and second struts at a first angle, each of the first struts extending between adjacent bends in a first direction and each of the second struts extending between adjacent bends in a second direction, the second direction being different than the first direction; and wherein every other bend on a selected turn of the elongate member is circumferentially aligned with every other bend of a longitudinally adjacent turn and wherein the elongate member is attached to the graft such that the bends are at least partially compressed from the first angle in a relaxed state to a second angle, the second angle being less than the first, wherein the elongate member torsions the graft causes circumferential and longitudinal folds in the graft between opposing bends of longitudinally adjacent turns of the elongate member. The endoluminal prosthesis, wherein the elongate member is attached to the graft about the plurality of bends. The endoluminal prosthesis, wherein the elongate member is attached to the graft about the first and second struts of the plurality of bends. The endoluminal prosthesis, wherein each bend of the elongate member on a selected turn is circumferentially aligned with bends of a longitudinally adjacent turn. The endoluminal prosthesis, wherein the second angle is from about 0 to about 80% of the first angle. The endoluminal prosthesis wherein the second angle is from about 20 to about 60% of the first angle. The endoluminal prosthesis, wherein the second angle is about 40% of the first angle. The endoluminal prosthesis, wherein the length of the first and second struts in the second section of the graft are progressively increased moving in a direction from a first end of the second section toward a second end of the second section. The endoluminal prosthesis, wherein the length of the first and second struts in the second section of the graft is increased by a progressively smaller amount moving in a direction from the first end toward the second end. The endoluminal prosthesis, wherein an increase in the length of the first and second struts in the second section is substantially the same. The endoluminal prosthesis, wherein the length of the first and second struts in the second section is increased by a progressively larger amount moving in a direction from the first end toward the second end. The endoluminal prosthesis, wherein the elongate support member is attached in the first section of the graft in a helix. The endoluminal prosthesis, wherein the elongate support member is attached in the second section of the graft in a conical helix. The endoluminal prosthesis, wherein the spacing between the turns of the elongate member on the graft is from about 0 millimeters to about 8 millimeters. The endoluminal prosthesis, wherein the spacing between the turns of the elongate member is about 4 millimeters. The endoluminal prosthesis, wherein the elongate member has a predetermined number of bends extending 360 degrees around a central axis. The endoluminal prosthesis, wherein the predetermined number of bends is from 2 to 9 bends. The endoluminal prosthesis, wherein the predetermined number of bends is from 4 to 6 bends. The endoluminal prosthesis, wherein the predetermined number of bends is 5 bends. The endoluminal prosthesis, wherein the graft further comprises a third section having a uniform diameter, the third section being in mechanical communication with the second section of the graft.

An endoluminal prosthesis comprising:

a tubular graft having a lumen defined therein;

an elongate member having a plurality of turns circumferentially and longitudinally attached to the graft, the elongate member comprising a plurality of bends, each bend connecting a pair of first and second struts at a first angle, each of the first struts extending between adjacent bends in a first direction and each of the second struts extending between adjacent bends in a second direction, the second direction being different than the first direction; and wherein every other bend on a selected turn of the elongate member is circumferentially aligned with every other bend of a longitudinally adjacent turn and wherein the elongate member is attached to the graft such that the bends are at least partially compressed from the first angle in a relaxed state to a second angle, the second angle being less than the first, wherein the elongate member torsions the graft and cause circumferential and longitudinal folds in the graft between opposing bends of longitudinally adjacent turns of the elongate member.

The endoluminal prosthesis, wherein the elongate member is attached to the graft about the plurality of bends. The endoluminal prosthesis, wherein the elongate member is attached to the graft about the first and second struts of the plurality of bends. The endoluminal prosthesis, wherein the second angle is from about 0 to about 80% of the first angle. The endoluminal prosthesis, wherein the second angle is from about 20 to about 60% of the first angle. The endoluminal prosthesis, wherein the second angle is about 40% of the first angle. The endoluminal prosthesis, wherein the spacing between the turns of the elongate member on the graft is from about 0 millimeters to about 8 millimeters. The endoluminal prosthesis, wherein the spacing between the turns of the elongate member is about 4 millimeters. The endoluminal prosthesis, wherein the elongate member has a predetermined number of bends extending 360 degrees around a central axis. The endoluminal prosthesis, wherein the predetermined number of bends is from 2 to 9 bends. The endoluminal prosthesis, wherein the predetermined number of bends is from 4 to 6 bends. The endoluminal prosthesis, wherein the predetermined number of bends is 5 bends. The endoluminal prosthesis, wherein the elongate support member is attached to the graft in a helix.

An endoluminal prosthesis comprising:

a tubular graft having a lumen defined therein;

an elongate member having a plurality of torqued turns circumferentially and longitudinally attached to the graft, wherein the elongate member torsions the graft and causes circumferential and longitudinal folds in the graft between opposing bends of longitudinally adjacent turns of the elongate member.

The endoluminal prosthesis, wherein the elongate member comprises a plurality of first and second struts and a plurality of bends joining the plurality of first and second struts. The endoluminal prosthesis, wherein the elongate member is attached to the graft such that the bends are at least partially compressed from a first angle in a relaxed state to a second angle. The endoluminal prosthesis, wherein the elongate member is attached to the graft about the plurality of bends. The endoluminal prosthesis, wherein the elongate member is attached to the graft about the first and second struts of the plurality of bends. The endoluminal prosthesis, wherein the spacing between the turns of the elongate member on the graft is from about 0 millimeters to about 8 millimeters. The endoluminal prosthesis, wherein the spacing between the turns of the elongate member is about 4 millimeters. The endoluminal prosthesis, wherein the elongate member has a predetermined number of bends extending 360 degrees around a central axis. The endoluminal prosthesis, wherein the predetermined number of bends is from 2 to 9 bends. The endoluminal prosthesis, wherein the predetermined number of bends is from 4 to 6 bends. The endoluminal prosthesis, wherein the predetermined number of bends is 5 bends. The endoluminal prosthesis, wherein each bend of the elongate member on a selected turn is circumferentially aligned with bends of a longitudinally adjacent turn. The endoluminal prosthesis, wherein the second angle is from about 0 to about 80% of the first angle. The endoluminal prosthesis, wherein the second angle is from about 20 to about 60% of the first angle. The endoluminal prosthesis, wherein the second angle is about 40% of the first angle. The endoluminal prosthesis, wherein the elongate member is attached to the graft in a helix.

An endoluminal prosthesis comprising:
a tubular graft having a lumen defined therein;
an elongate member having a plurality of torqued turns circumferentially and longitudinally attached to the graft, the elongate member comprising a plurality of bends, each bend connecting a pair of first and second struts at a first angle, each of the first struts extending between adjacent bends in a first direction and each of the second struts extending between adjacent bends in a second direction, the second direction being different than the first direction; and
wherein the elongate member is attached to the graft such that the bends are at least partially compressed from the first angle in a relaxed state to a second angle, the second angle being less than the first, and wherein the elongate member torsions the graft and creates a plurality of cells, each cell having a boundary comprising a pair of first and second struts of a first turn and a second turn, the second turn being longitudinally adjacent to the first turn, and tensioned folds extending longitudinally and circumferentially between the first and second turns, and relaxed folds are disposed within the boundary of the plurality cells.

The endoluminal prosthesis, wherein the elongate member is attached to the graft about the plurality of bends. The endoluminal prosthesis, wherein the elongate member is attached to the graft about the first and second struts of the plurality of bends. The endoluminal prosthesis, wherein each bend of the elongate member on a selected turn is circumferentially aligned with bends of a longitudinally adjacent turn. The endoluminal prosthesis, wherein the second angle is from about 0 to about 80% of the first angle. The endoluminal prosthesis, wherein the second angle is from about 20 to about 60% of the first angle. The endoluminal prosthesis, wherein the second angle is about 40% of the first angle. The endoluminal prosthesis, wherein the spacing between the turns of the elongate member on the graft is from about 0 millimeters to about 8 millimeters. The endoluminal prosthesis, wherein the spacing between the turns of the elongate member is about 4 millimeters. The endoluminal prosthesis, wherein the elongate member has a predetermined number of bends extending 360 degrees around a central axis. The endoluminal prosthesis, wherein the predetermined number of bends is from 2 to 9 bends. The endoluminal prosthesis, wherein the predetermined number of bends is from 4 to 6 bends. The endoluminal prosthesis, wherein the predetermined number of bends is 5 bends. The endoluminal prosthesis, wherein the elongate support member is attached in the first section of the graft in a helix.

An endoluminal prosthesis comprising:
a tubular graft having a lumen defined therein, the graft having a first condition and a second condition, the first condition comprising a substantially straightened portion and the second condition comprising a curvature having an interior radius and an exterior radius, the inner radius being less than the outer radius; and
an elongate member having a plurality of torqued turns circumferentially and longitudinally attached to the graft, the elongate member comprising a plurality of bends, each bend connecting a pair of first and second struts at a first angle, each of the first struts extending between adjacent bends in a first direction and each of the second struts extending between adjacent bends in a second direction, the second direction being different than the first direction;
wherein the elongate member is attached to the graft such that the bends are at least partially compressed from the first angle in a relaxed state to a second angle, the second angle being less than the first,
wherein the elongate member torsions the graft and creates a plurality of cells, each cell having a boundary comprising a pair of first and second struts of a first turn and a second turn, the second turn being longitudinally adjacent to the first turn, and tensioned folds extending longitudinally and circumferentially between the first and second turns, and relaxed folds are disposed within the boundary of the plurality cells; and
wherein when the graft is in the first condition, the lumen has a substantially circular cross sectional area, and wherein when the graft is in the second condition, the plurality of cells about the interior radius at least partially compress inwardly along the relaxed folds such that the lumen remains substantially open.

An endoluminal prosthesis comprising:
a tubular graft having a lumen defined therein;
an elongate member having a plurality of turns with a predetermined curve about a central axis circumferentially and longitudinally attached to the graft, the elongate member comprising a plurality of bends, each bend connecting a pair of first and second struts at a first angle, each of the first struts extending between adjacent bends in a first direction and each of the second struts extending between adjacent bends in a second direction, the second direction being different than the first direction; and
wherein every other bend on a selected turn of the elongate member is circumferentially aligned with every other bend of a longitudinally adjacent turn and wherein the elongate member is attached to the graft such that the bends are at least partially compressed from the first angle in a relaxed state to a second angle, the second angle being less than the first, wherein the elongate member torsions the graft and cause circumferential and longitudinal folds in the graft between opposing bends of longitudinally adjacent turns of the elongate member.

The endoluminal prosthesis, wherein the preformed curve of the elongate member is heat set.

A method of making an endoluminal prosthesis, the method comprising:
providing a tubular graft formed of biocompatible material having a proximal end, a distal end, and a lumen disposed therethrough;
providing an elongate member comprising a plurality of bends, each bend connecting a pair of first and second struts at a first angle, each of the first struts extending between adjacent bends in a first direction and each of the second struts extending between adjacent bends in a second direction, the second direction being different than the first direction;
positioning the elongate member longitudinally and circumferentially about an outer surface of the graft forming a plurality of torqued turns, wherein every other bend of the elongate member is circumferentially aligned with longitudinally adjacent bends; and attaching the elongate member upon the graft in a partially compressed form under tension, such that first angle is compressed to a second angle, the second angle being less than the second angle.

A method of treating a diseased body lumen, the method comprising:

providing an endoluminal prosthesis comprising a tubular graft extending in a longitudinal direction, the graft having an inner surface forming a lumen extending a length of the graft; and an elongate member attached to the graft in a circumferentially and longitudinally extending manner such that the elongate member forms a series of longitudinally spaced apart turns, each turn extending substantially around a circumference of the graft, wherein the elongate member is attached to the graft such that the elongate member torsions the graft in at least the circumferential direction and causes the graft to form circumferentially and longitudinally extending folds in the portions of the graft disposed between longitudinally adjacent turns of the elongate member, and wherein the circumferentially and longitudinally extending folds create a plurality of cells, each cell having a boundary comprising 1) a portion of the elongate member disposed on each of a first and a second turn, the first turn being longitudinally adjacent the second turn, and 2) two tensioned folds extending longitudinally and circumferentially between the first and second turns, wherein each cell comprises a relaxed fold disposed within the boundary when the graft is in a first condition having a substantially straight shape;

advancing the endoluminal prosthesis to a body lumen having a curved shape;

moving the endoluminal prosthesis from the first configuration in which the endoluminal prosthesis is substantially straight to a second condition in which the endoluminal is curved to approximate the curved shape of the body lumen, the endoluminal prosthesis having an interior radius and an exterior radius, the inner radius being less than the outer radius, and wherein when the endoluminal prosthesis is in the first condition, the lumen has a substantially circular open cross sectional area, and wherein when the graft is in the second condition the portion of the graft disposed in each of the plurality of cells disposed about at least the interior radius at least partially compress inwardly along the relaxed folds, thereby creating a plurality of discrete, localized folds in the graft that substantially maintain the patency of the lumen; and implanting the endoluminal prosthesis in the body lumen having a curved shape.

A preform of a medical device, comprising:

an elongate member comprising a plurality of bends, each bend connecting a pair of first and second struts at an, each of the first struts extending between adjacent bends in a first direction and each of the second struts extending between adjacent bends in a second direction, the second direction being different than the first direction;

a first section of the elongate member having first and second ends, wherein a length of the first struts is shorter than a length of the second struts, and the angle between pairs of first and second struts in the relaxed state is progressively larger for each successive bend moving in a direction from the first end toward the second end.

The preform, wherein the lengths of the first and second struts are progressively increased moving in a direction from the first end toward the second end. The preform wherein the lengths of the first and second struts are increased by a progressively smaller amount moving in a direction from the first end toward the second end. The preform, wherein every other bend of the first section is circumferentially aligned with longitudinally adjacent bends when the elongate member is in a helical shape. The preform, wherein each bend of the first section is circumferentially aligned with longitudinally adjacent bends when the elongate member is in a helical form. The preform, wherein when the angles between the first and second struts of the first section are compressed between about 0% to about 80%, each of the bends of the first section are circumferentially aligned with longitudinally adjacent bends. The preform, wherein when the angles between the first and second struts of the first section are compressed between about 40% to about 60%, each of the bends of the first section are circumferentially aligned with longitudinally adjacent bends. The preform, wherein when the angles between the first and second struts of the first section are compressed between about 0% to about 80%, every other bend of the first section is circumferentially aligned with longitudinally adjacent bends. The preform, wherein when the angles between the first and second struts of the first section are compressed between about 40% to about 60%, every other bend of the first section are circumferentially aligned with longitudinally adjacent bends. The preform, further comprising a second section of the elongate member having a first end and a second end, the second end being connected to the first end of the first section, wherein, in the second section, a length of the first struts is shorter than a length of the second struts and the angles between the first and second struts at each bend are substantially uniform throughout the second section in a relaxed state. The preform, wherein when the elongate member is in a helical shape, the second section has a substantially cylindrical shape having a substantially constant diameter, and the first section has a substantially conical tapered shape that extends in a radially outward direction from the diameter of the second section. The preform, wherein every other bend of the first and second sections are circumferentially aligned with longitudinally adjacent bends when the elongate member is in a helical shape. The preform, wherein each bend of the first and second sections are circumferentially aligned with longitudinally adjacent bends when the elongate member is in a helical shape. The preform, wherein an angle between a pair of first and second struts connected by a first bend disposed at the first end of the first section is less than the angle between the pairs of first and second struts of the second section in a relaxed state, wherein bends of longitudinally adjacent turns of the elongate member are aligned through the transition between the substantially cylindrical portion of the second section and the substantially conical section of the first section when the elongate member is in a helical shape. The preform, wherein when the angle between the first and second struts of the second section is compressed between about 0% to about 80%, each of the bends of the first and second sections are circumferentially aligned with longitudinally adjacent bends. The preform, wherein when the angle between the first and second struts of the second section is compressed between about 40% to about 60%, each of the bends of the first and second sections are circumferentially aligned with longitudinally adjacent bends. The preform, wherein when the angle between the first and second struts of the second section is compressed between about 0% to about 80%, every other bend of the first and second sections are circumferentially aligned with longitudinally adjacent bends. The preform, wherein when the angle between the first and second struts of the second section is compressed between about 40% to about 60%, every other bend of the first and second sections are circumferentially aligned with longitudinally adjacent bends. The preform, wherein when the angles between the first and second struts of the first and second sections are compressed between about 0% to about 80%, each of the bends of the first and second sections are circumferentially aligned with longitudinally adjacent bends. The preform, wherein when the angles between the first and second struts of the first and second sections are compressed between about 40% to about 60%, each of the bends of the first and second sections are circumferentially aligned with longitudinally adjacent bends. The preform, wherein when the angles between the first and second struts of the first and second sections are compressed between about 0% to about 80%, every other bend of the first and second sections are circumferentially aligned with longitudinally adjacent bends. The preform, wherein when the angles between the first and second struts of the first and second sections are compressed between about 40% to about 60%, every other bend of the first and second sections are circumferentially aligned with longitudinally adjacent bends. The preform, wherein a portion of the central axis has a curved predetermined shape. The preform, wherein the predetermined number of bends is half of the total number of bends in each turn of the elongate member. The preform, wherein the total number of bends in each turn of the elongate member is between about eight and about twenty-four. The preform, wherein the total number of bends in each turn of the elongate member is about ten. The preform, wherein a predetermined spacing between turns is between about zero and about twelve millimeters. The preform, wherein a predetermined spacing between turns is about four millimeters. The preform, further comprising: a third section of the elongate member connected to the second end of the first section, wherein, in the third section, a length of the first and second struts is substantially the same and the angles between pairs of first and second struts are substantially uniform; and a fourth section of the elongate member connected to the first end of the second section, wherein, in the fourth section, a length of the first and second struts is substantially the same and the angles between pairs of first and second struts are substantially uniform, the angles of the fourth section being less than the angles of the third section. The preform, wherein the first and second struts of the third section are longer than the first and second struts of the third section. The preform, wherein each of the first through fourth sections are directly connected to each other. The preform, wherein the bends and the first and second struts of the first through fourth sections lie in the same plane when the elongate member is in a relaxed state. The preform, wherein the bends and first and second struts of the first and second sections lie in the same plane, and the bends and first and second struts disposed at end portions of the third and fourth sections curve away from the plane. The preform, wherein end portions of the third and fourth sections curve away from the plane in a cylindrical shape such that when the elongate member is in a helical shape, the third and fourth sections have a substantially non-helical cylindrical portion. The preform, wherein the angle between the pairs of first and second struts of the third section substantially approximate the angles between pairs of first and second struts of the first section that are longitudinally adjacent to and substantially circumferentially aligned with the pairs of first and second struts of the third section. The preform, wherein the third section comprises less than a predetermined number of bends in each turn of the elongate member when the elongate member is in a helical shape, the turns of the elongate member extending 360 degrees around a central axis of a helix, wherein the bends and first and second struts of the third section are positioned to fill a gap disposed at the second end of the first section when the first section is in a helical shape. The preform, wherein the first and second struts of the third section are spaced away from longitudinally adjacent first and second struts of the first section. The preform, wherein, when the elongate member is in a helical shape, the angle between the pairs of first and second struts of the fourth section substantially approximate the angles between pairs of first and second struts of the second section that are longitudinally adjacent to and substantially circumferentially aligned with the pairs of first and second struts of the fourth section. The preform, wherein the fourth section comprises less than a predetermined number of bends in each turn of the elongate member when the elongate member is in a helical shape, the turns of the elongate member extending 360 degrees around a central axis of a helix, wherein the bends and first and second struts of the third section are positioned to fill a gap disposed at the first end of the second section when the second section is in a helical shape. The preform, wherein the first and second struts of the fourth section are spaced away from longitudinally adjacent first and second struts of the second section.

A preform of a medical device, comprising:

an elongate member comprising a plurality of bends, each bend connecting a pair of first and second struts at an angle, each of the first struts extending between adjacent bends in a first direction and each of the second struts extending between adjacent bends in a second direction, the second direction being different than the first direction;

a first section of the elongate member having a first end and a second end, wherein, in the first section, a length of the first struts is shorter than a length of the second struts and the angles between the first and second struts at each bend are substantially uniform throughout the second section in a relaxed state;

a second section of the elongate member connected to the first end of the first section, wherein, in the second section, a length of the first and second struts is substantially the same and the angles between pairs of first and second struts are substantially uniform; and a third section of the elongate member connected to the second end of the first section, wherein, in the third section, a length of the first and second struts is substantially the same and the angles between pairs of first and second struts are substantially uniform, wherein the bends and first and second struts of the first section lie in the same plane, and the bends and first and second struts disposed at end portions of the second and third sections curve away from the plane when the elongate member is in a relaxed state.

The preform, wherein every other bend of the first section is circumferentially aligned with longitudinally adjacent bends when the elongate member is in a helical shape. The preform, wherein each bend of the first section is circumferentially aligned with longitudinally adjacent bends when the elongate member is in a helical form. The preform, wherein when the angles between the first and second struts of the first section are compressed between about 0% to about 80%, each of the bends of the first section are circumferentially aligned with longitudinally adjacent bends. The preform, wherein when the angles between the first and second struts of the first section are compressed between about 40% to about 60%, each of the bends of the first section are circumferentially aligned with longitudinally adjacent bends. The preform, wherein when the angles between the first and second struts of the first section are compressed between about 0% to about 80%, every other bend of the first section is circumferentially aligned with longitudinally adjacent bends. The preform, wherein when the angles between the first and second struts of the first section are compressed between about 40% to about 60%, every other bend of the first section are circumferentially aligned with longitudinally adjacent bends. The preform, wherein end portions of the second and third sections curve away from the plane in a cylindrical shape such that when the elongate member is in a helical shape, the second and third sections have a substantially non-helical cylindrical portion. The preform, wherein the angle between the pairs of first and second struts of the second section substantially approximate the angles between pairs of first and second struts of the first section that are longitudinally adjacent to and substantially circumferentially aligned with the pairs of first and second struts of the second section. The preform, wherein the second section comprises less than a predetermined number of bends in each turn of the elongate member when the elongate member is in a helical shape, the turns of the elongate member extending 360 degrees around a central axis of a helix, wherein the bends and first and second struts of the second section are positioned to fill a gap disposed at the first end of the first section when the first section is in a helical shape. The preform, wherein the first and second struts of the second section are spaced away from longitudinally adjacent first and second struts of the first section. The preform, wherein, when the elongate member is in a helical shape, the angle between the pairs of first and second struts of the third section substantially approximate the angles between pairs of first and second struts of the first section that are longitudinally adjacent to and substantially circumferentially aligned with the pairs of first and second struts of the third section. The preform, wherein the third section comprises less than a predetermined number of bends in each turn of the elongate member when the elongate member is in a helical shape, the turns of the elongate member extending 360 degrees around a central axis of a helix, wherein the bends and first and second struts of the third section are positioned to fill a gap disposed at the second end of the first section when the first section is in a helical shape. The preform, wherein the first and second struts of the third section are spaced away from longitudinally adjacent first and second struts of the first section. The preform, wherein the second and third sections curve away from the plane in a cylindrical shape such that when the elongate member is wound such that the first section is in a helical shape, the second and third sections form a substantially non-helical cylindrical portion. The preform, wherein the second and third sections are positioned to fill gaps disposed at the first and second ends of the first section, respectively, when the first section has the helical shape. The preform, wherein a portion of the central axis has a curved predetermined shape.

A support member of a medical device, comprising:
an elongate member comprising a plurality of bends, each bend connecting a pair of first and second struts at an angle, each of the first struts extending between adjacent bends in a first direction and each of the second struts extending between adjacent bends in a second direction, the second direction being different than the first direction,
a first section of the elongate member having first and second ends, wherein, a length of the first struts is shorter than a length of the second struts, and the angle between pairs of first and second struts in the relaxed state is progressively larger for each successive bend moving in a direction from the first end toward the second end;
a second section of the elongate member having a first end and a second end, the second end being connected to the first end of the first section, wherein, in the second section, a length of the first struts is shorter than a length of the second struts and the angles between the first and second struts at each bend are substantially uniform throughout the second section in a relaxed state,
wherein the bends and first and second struts of the first and second sections are arranged in an undulating pattern about a central axis in a helical shape having a substantially cylindrical shape with a substantially constant diameter in the second section, and a substantially conical tapered shape in the first section that extends in a radially outward direction from the diameter of the second section when the elongate member is in a relaxed state,
and wherein each of the bends of the first and second sections is circumferentially aligned with longitudinally adjacent bends in the relaxed state.
The support device, wherein the lengths of the first and second struts are progressively increased moving in a direction from the first end toward the second end. The support device, wherein an angle between a pair of first and second struts connected by a first bend disposed at the first end of the first section is less than the angle between the pairs of first and second struts of the second section in a relaxed state, wherein bends of longitudinally adjacent turns of the elongate member are aligned through the transition between the substantially cylindrical portion of the second section and the substantially conical section of the first section when the elongate member is in a helical shape. The support device, further comprising: a third section of the elongate member connected to the second end of the first section, wherein, in the third section, a length of the first and second struts is substantially the same and the angles between pairs of first and second struts are substantially uniform; and a fourth section of the elongate member connected to the first end of the second section, wherein, in the fourth section, a length of the first and second struts is substantially the same and the angles between pairs of first and second struts are substantially uniform, the angles of the fourth section being less than the angles of the third section. The support device, wherein the first and second struts of the third section are longer than the first and second struts of the third section. The support device, wherein each of the first through fourth sections are directly connected to each other. The support device, wherein a portion of the central axis has a curved predetermined shape.

A support member of a medical device, comprising:
an elongate member comprising a plurality of bends, each bend connecting a pair of first and second struts at an angle, each of the first struts extending between adjacent bends in a first direction and each of the second struts extending between adjacent bends in a second direction, the second direction being different than the first direction,
wherein the elongate member has first and second ends, and a length of the first struts is shorter than a length of the second struts, and the angle between pairs of first and second struts in the relaxed state is progressively larger for each successive bend moving in a direction from the first end toward the second end,
wherein the bends and first and second struts are arranged in an undulating pattern about a central axis in a helical shape having a substantially conical tapered shape that extends in a radially outward direction moving from the first end toward the second end when the elongate member is in a relaxed state,
and wherein each of the bends is circumferentially aligned with longitudinally adjacent bends in the relaxed state.
The support member, wherein a portion of the central axis has a curved predetermined shape.

A support member of a medical device, comprising:
an elongate member comprising a plurality of bends, each bend connecting a pair of first and second struts at an angle, each of the first struts extending between adjacent bends in a first direction and each of the second struts extending between adjacent bends in a second direction, the second direction being different than the first direction, a first section of the elongate member having a first end and a second end, wherein, in the first section, a length of the first struts is shorter than a length of the second struts and the angles between the first and second struts at each bend are substantially uniform throughout the second section in a relaxed state, and wherein the bends and first and second struts of the first section are arranged in an undulating pattern about a central axis in a helical form having a substantially cylindrical shape, and wherein each of the bends of the first section is circumferentially aligned with longitudinally adjacent bends, when the elongate member is in a relaxed state;

a second section of the elongate member connected to the first end of the first section, wherein, in the second section, a length of the first and second struts is substantially the same and the angles between pairs of first and second struts are substantially uniform; and a third section of the elongate member connected to the second end of the first section, wherein, in the third section, a length of the first and second struts is substantially the same and the angles between pairs of first and second struts are substantially uniform, wherein the second and third sections of the elongate member have a substantially non-helical cylindrical shape in a relaxed state.

The support member, wherein the bends and first and second struts of the second and third sections are positioned to fill gaps disposed at the first and second ends of the first section, respectively, the gaps being formed by the helical shape of the first section. The support member, wherein a portion of the central axis has a curved predetermined shape.

A preform of a medical device, comprising:

an elongate member comprising first and second ends and a plurality of attachment members spaced therebetween, wherein portions of the elongate member extending between adjacent attachment members are substantially straight.

The preform, wherein the attachment members are eyelets.

The preform, wherein the eyelets are integrally formed with the elongate member.

An endoluminal prosthesis comprising:

a tubular graft comprising a first section, a second section, and a lumen defined therein;

an elongate member having a plurality of torqued turns circumferentially and longitudinally attached to the graft at a plurality of attachment members disposed along a length thereof, each attachment member of a selected turn of the elongate member being circumferentially aligned with each attachment member of a longitudinally adjacent turn, wherein the elongate member torsions the graft and creates longitudinal and circumferential folds in the graft between adjacent turns of the elongate member, and wherein at least one portion of the elongate member extending between two circumferentially and longitudinally adjacent attachment members is characterized by the lack of circumferentially compressible members.

While presently preferred embodiments have been described, it should be understood that modifications may be made without departing from the invention. The scope of the invention is defined by the appended claims, and all devices that come within the meaning of the claims, either literally or by equivalence, are intended to be embraced therein. Furthermore, the advantages of the embodiments described above are not necessarily the only advantages of the embodiments, and it is not necessarily expected that all of the described advantages will be achieved with every embodiment.

The invention claimed is:

1. An endoluminal prosthesis comprising:
   a tubular graft extending in a longitudinal direction, the graft having an inner surface forming a lumen extending a length of the graft; and
   an elongate member attached to the graft in a circumferentially and longitudinally extending manner and having a series of longitudinally spaced apart turns, each turn extending substantially around a circumference of the graft,
   wherein the elongate member is attached to and torsions the graft in at least the circumferential direction, the graft having circumferentially and longitudinally extending folds in the portions of the graft disposed between longitudinally adjacent turns of the elongate member.

2. The prosthesis of claim 1, wherein the graft comprises a first section having a uniform diameter.

3. The prosthesis of claim 2, further comprising a second section having a first opening at a first end and a second opening at a second end with the second opening being larger than the first, the graft increasing in size moving from the first opening to the second opening, the first and second sections being in mechanical communication with each other.

4. The prosthesis of claim 3, wherein the elongate member comprises a plurality of first and second struts connected by bends at an angle, each of the first struts extending between adjacent bends disposed on the same turn in a first direction and each of the second struts extending between adjacent bends disposed on the same turn in a second direction, the second direction being different than the first direction.

5. The prosthesis of claim 4, wherein the elongate member comprises a first section corresponding to the first section of the graft and a second section corresponding to the second section of the graft, wherein the first struts are longer than the second struts in the first and second sections of the elongate member.

6. The prosthesis of claim 5, wherein in the first section of the elongate member, each angle between pairs of first and second struts is substantially the same.

7. The prosthesis of claim 6, wherein, in the second section, the length of the first strut and a length of the second strut progressively increases moving from the first end of the second section toward the second end, and the angle at each bend progressively increases for each successive bend moving in a direction from the first end toward the second end of the second section.

8. The prosthesis of claim 7, wherein at least one bend on a selected turn of the elongate member is circumferentially aligned with at least one bend on a longitudinally adjacent turn and wherein the elongate member is attached to the graft such that at least one of the angles of at least one of the bends is at least partially compressed from a first angle when the elongate body is in a relaxed and unattached state to a second angle when the elongate member is attached to the graft, the second angle being less than the first.

9. The prosthesis of claim 8, wherein each of the bends on each of the turns of the elongate member is circumferentially aligned with each other.

10. The prosthesis of claim 9, wherein the circumferentially and longitudinally extending folds extend between opposing bends of longitudinally adjacent turns of the elongate member.

11. The prosthesis of claim 10, wherein the circumferentially and longitudinally extending folds create a plurality of cells, each cell having a boundary comprising a pair of first and second struts of a first turn and a second turn, the second turn being longitudinally adjacent to the first turn, wherein each cell comprises and relaxed fold disposed within the boundary when the graft is in a first condition having a substantially straight shape.

12. The prosthesis of claim 11, wherein the graft is movable between the substantially straight first condition to a second condition in which the graft is curved, the graft having an interior radius and an exterior radius, the inner radius being less than the outer radius, and wherein when the graft is in the first condition, the lumen has a substantially circular open cross sectional area, and wherein when the graft is in the second condition the portion of the graft disposed in each of the plurality of cells disposed about at least the interior radius at least partially compress inwardly along the relaxed folds, thereby creating a plurality of discrete, localized folds in the graft that substantially maintain the patency of the lumen.

13. The prosthesis of claim 1, wherein the elongate member comprises a plurality of discrete attachment members disposed at predetermined intervals along at least a portion of the elongate member.

14. The prosthesis of any of claim 13, wherein the circumferentially and longitudinally extending folds extend between opposing attachment members of longitudinally adjacent turns of the elongate member.

15. The prosthesis of claim 14, wherein the circumferentially and longitudinally extending folds create a plurality of cells, each cell having a boundary comprising a portion of the elongate member extending between first and second attachment members disposed on each of a first and a second turn, the first turn being longitudinally adjacent the second turn, and two tensioned folds extending longitudinally and circumferentially between the first and second turns, wherein each cell comprises a relaxed fold disposed within the boundary when the graft is in a first condition having a substantially straight shape.

16. An endoluminal prosthesis preform, comprising:
an elongate member comprising a plurality of bends, each bend connecting a pair of first and second struts at an angle, each of the first struts extending between adjacent bends in a first direction and each of the second struts extending between adjacent bends in a second direction, the second direction being different than the first direction;
a first section of the elongate member having first and second ends, wherein a length of the first struts is shorter than a length of the second struts, and the angle between pairs of first and second struts in the relaxed state is progressively larger for each successive bend moving in a direction from the first end toward the second end.

17. The preform of claim 16, wherein the lengths of the first and second struts progressively increase moving in a direction from the first end toward the second end.

18. The preform of claim 17, wherein every other bend of the first section is circumferentially aligned with longitudinally adjacent bends when the elongate member is in a helical shape.

19. The preform of claim 17, wherein the lengths of the first and second struts increases by a progressively smaller amount moving in a direction from the first end toward the second end.

* * * * *